(12) United States Patent
Barlow et al.

(10) Patent No.: US 7,678,363 B2
(45) Date of Patent: Mar. 16, 2010

(54) METHODS OF TREATING PSYCHIATRIC CONDITIONS COMPRISING ADMINISTRATION OF MUSCARINIC AGENTS IN COMBINATION WITH SSRIS

(75) Inventors: Carrolee Barlow, Del Mar, CA (US); Todd A. Carter, San Diego, CA (US); Kym I. Lorrain, San Diego, CA (US); Jammieson C. Pires, San Diego, CA (US); Andrew Morse, San Diego, CA (US); Dana Gitnick, San Marcos, CA (US); Kai Treuner, San Diego, CA (US); Alex Broadhead, San Diego, CA (US)

(73) Assignee: BrainCells Inc, San Diego, CA (US)

( * ) Notice: Subject to any disclaimer, the term of this patent is extended or adjusted under 35 U.S.C. 154(b) by 409 days.

(21) Appl. No.: 11/467,527

(22) Filed: Aug. 25, 2006

(65) Prior Publication Data

US 2007/0049576 A1    Mar. 1, 2007

Related U.S. Application Data

(60) Provisional application No. 60/711,846, filed on Aug. 26, 2005, provisional application No. 60/727,127, filed on Oct. 14, 2005, provisional application No. 60/738,133, filed on Nov. 17, 2005, provisional application No. 60/803,826, filed on Jun. 2, 2006.

(51) Int. Cl.
*A61K 49/00* (2006.01)
*A61K 43/00* (2006.01)
*A01N 43/00* (2006.01)
*C07C 213/00* (2006.01)

(52) U.S. Cl. .................. 424/9.1; 514/183; 514/214.03; 564/347

(58) Field of Classification Search .................. None
See application file for complete search history.

(56) References Cited

U.S. PATENT DOCUMENTS

| | | |
|---|---|---|
| 4,067,971 A | 1/1978 | Francis et al. |
| 4,710,508 A | 12/1987 | Bergmeier et al. |
| 4,786,648 A | 11/1988 | Bergmeier et al. |
| 4,855,290 A | 8/1989 | Fisher et al. |
| 4,866,077 A | 9/1989 | Bogeso et al. |
| 4,870,081 A | 9/1989 | Orlek et al. |
| 4,925,858 A | 5/1990 | Bogeso et al. |
| 4,940,795 A | 7/1990 | Tsukamoto et al. |
| 4,968,691 A | 11/1990 | Orlek et al. |
| 4,971,975 A | 11/1990 | Hadley et al. |
| 4,981,858 A | 1/1991 | Fisher et al. |
| 4,992,457 A | 2/1991 | Schulman et al. |
| 4,996,210 A | 2/1991 | Tsukamoto et al. |
| 5,041,455 A | 8/1991 | Sauerberg et al. |
| 5,041,549 A | 8/1991 | Tsukamoto et al. |
| 5,043,345 A | 8/1991 | Sauerberg et al. |
| 5,093,333 A | 3/1992 | Saab |
| 5,110,828 A | 5/1992 | Bromidge et al. |
| 5,124,460 A | 6/1992 | Humphrey |
| 5,132,316 A | 7/1992 | Hadley et al. |
| 5,137,895 A | 8/1992 | Munson, Jr. et al. |
| 5,166,357 A | 11/1992 | Orlek et al. |
| 5,229,382 A | 7/1993 | Chakrabarti et al. |
| 5,260,314 A | 11/1993 | Sauerberg et al. |
| 5,262,427 A | 11/1993 | Nielson et al. |
| 5,278,170 A | 1/1994 | Orlek et al. |
| 5,286,864 A | 2/1994 | Walther et al. |
| 5,314,901 A | 5/1994 | Bromidge et al. |
| 5,324,724 A | 6/1994 | Orlek et al. |
| RE34,653 E | 7/1994 | Tsukamoto et al. |
| 5,340,821 A | 8/1994 | Abe et al. |
| 5,356,912 A | 10/1994 | Nielsen et al. |
| 5,356,914 A | 10/1994 | Bromidge et al. |
| 5,362,739 A | 11/1994 | Orlek et al. |
| 5,362,860 A | 11/1994 | Huang et al. |
| 5,384,408 A | 1/1995 | Baker et al. |
| 5,403,931 A | 4/1995 | Tsukamoto et al. |
| 5,407,938 A | 4/1995 | Fisher et al. |
| 5,412,096 A | 5/1995 | Tsukamoto et al. |
| 5,424,301 A | 6/1995 | Huang et al. |
| 5,451,587 A | 9/1995 | Walther et al. |
| 5,468,875 A | 11/1995 | Sabb et al. |
| 5,508,405 A | 4/1996 | Walther et al. |
| 5,510,478 A | 4/1996 | Sabb |
| 5,512,574 A | 4/1996 | Husbands et al. |
| 5,527,813 A | 6/1996 | Sauerberg et al. |
| 5,534,520 A | 7/1996 | Fisher et al. |
| 5,534,522 A | 7/1996 | Ando et al. |
| 5,541,194 A | 7/1996 | Orlek et al. |
| 5,545,740 A | 8/1996 | Hughes et al. |
| 5,571,819 A | 11/1996 | Sabb |
| 5,571,826 A | 11/1996 | Sauerberg et al. |
| 5,574,043 A | 11/1996 | Sauerberg et al. |
| 5,578,602 A | 11/1996 | Sauerberg et al. |
| 5,580,880 A | 12/1996 | Handa et al. |
| 5,599,937 A | 2/1997 | Glas et al. |
| 5,605,908 A | 2/1997 | Merritt et al. |

(Continued)

FOREIGN PATENT DOCUMENTS

EP            032325 A1      7/1989

(Continued)

OTHER PUBLICATIONS

Drugbank accession No. DB00472.*

(Continued)

*Primary Examiner*—John D. Ulm
*Assistant Examiner*—Stacey MacFarlane
(74) *Attorney, Agent, or Firm*—Sughrue Mion, PLLC

(57) ABSTRACT

The instant disclosure describes methods for treating diseases and conditions of the central and peripheral nervous system by stimulating or increasing neurogenesis. The disclosure includes compositions and methods based on muscarinic receptor modulation, such as via inhibition of acetylcholine esterase (AChE) activity, alone or in combination with another neurogenic agent to stimulate or activate the formation of new nerve cells.

2 Claims, 15 Drawing Sheets

U.S. PATENT DOCUMENTS

| | | | |
|---|---|---|---|
| 5,641,791 A | 6/1997 | Sauerberg et al. |
| 5,646,289 A | 7/1997 | Alt et al. |
| 5,650,174 A | 7/1997 | Muhammad et al. |
| RE35,593 E | 8/1997 | Orlek et al. |
| 5,665,745 A | 9/1997 | Alt et al. |
| 5,668,174 A | 9/1997 | Kawagishi et al. |
| 5,672,709 A | 9/1997 | Alt et al. |
| 5,675,007 A | 10/1997 | Keogh et al. |
| 5,756,501 A | 5/1998 | Sabb |
| 5,773,458 A | 6/1998 | Sabb et al. |
| 5,773,619 A | 6/1998 | Bromidge et al. |
| 5,808,075 A | 9/1998 | Bromidge et al. |
| 5,834,458 A | 11/1998 | Mitch |
| 5,852,029 A | 12/1998 | Fisher et al. |
| 5,902,814 A | 5/1999 | Gordon et al. |
| RE36,374 E | 11/1999 | Bogeso et al. |
| 5,981,545 A | 11/1999 | Jenkins et al. |
| 6,051,581 A | 4/2000 | Gordon et al. |
| 6,103,734 A | 8/2000 | Ibanez |
| 6,174,886 B1 | 1/2001 | Pineiro et al. |
| 6,235,745 B1 | 5/2001 | Megens |
| 6,237,645 B1 | 5/2001 | Pountey |
| 6,297,262 B1 | 10/2001 | Sams-Dodd et al. |
| 6,468,560 B2 | 10/2002 | Sauer et al. |
| 6,528,529 B1 | 3/2003 | Brann et al. |
| 6,596,869 B2 | 7/2003 | Hughes et al. |
| 6,911,452 B2 | 6/2005 | Schlienger |
| 6,911,477 B2 | 6/2005 | Villalobos et al. |
| 6,951,849 B2 | 10/2005 | Kelly et al. |
| 2001/0003588 A1 | 6/2001 | Sauer et al. |
| 2001/0018074 A1 | 8/2001 | Napper et al. |
| 2001/0036949 A1 | 11/2001 | Coe et al. |
| 2002/0127271 A1 | 9/2002 | Van-Schie |
| 2002/0150618 A1 | 10/2002 | Napper et al. |
| 2003/0100545 A1 | 5/2003 | Kelly et al. |
| 2003/0129246 A1 | 7/2003 | Napper et al. |
| 2003/0144285 A1 | 7/2003 | Brann et al. |
| 2003/0157169 A1 | 8/2003 | Sauer et al. |
| 2003/0176418 A1 | 9/2003 | Skjaerbaek et al. |
| 2005/0113357 A1 | 5/2005 | Anderson et al. |
| 2005/0130961 A1 | 6/2005 | Davis et al. |
| 2005/0209226 A1 | 9/2005 | Skjaerbaek et al. |
| 2007/0099947 A1 | 5/2007 | Dean et al. |

FOREIGN PATENT DOCUMENTS

| | | | |
|---|---|---|---|
| EP | 311313 A2 | 12/1989 |
| EP | 370415 A1 | 5/1990 |
| EP | 384285 A2 | 8/1990 |
| EP | 384288 A2 | 8/1990 |
| EP | 429344 A1 | 5/1991 |
| EP | 723781 A2 | 7/1996 |
| EP | 727208 A1 | 8/1996 |
| EP | 727209 A2 | 8/1996 |
| EP | 805153 A1 | 11/1997 |
| JP | 61280497 A | 12/1986 |
| JP | 6298732 A | 10/1994 |
| JP | 6305967 A | 11/1994 |
| WO | WO93/14089 A1 | 7/1993 |
| WO | WO94/22861 A1 | 10/1994 |
| WO | WO95/31547 A1 | 11/1995 |
| WO | WO96/03377 A1 | 2/1996 |
| WO | WO96/26196 A2 | 8/1996 |
| WO | WO96/40687 A1 | 12/1996 |
| WO | WO97/00894 A1 | 1/1997 |
| WO | WO97/17074 A1 | 5/1997 |
| WO | WO97/40044 A1 | 10/1997 |
| WO | WO98/00412 A1 | 1/1998 |
| WO | WO98/46226 A | 10/1998 |
| WO | WO98/47900 A1 | 10/1998 |
| WO | WO99/04778 A1 | 2/1999 |
| WO | WO99/17771 A1 | 4/1999 |
| WO | WO99/50247 A1 | 10/1999 |
| WO | WO01/05763 A2 | 1/2001 |
| WO | WO01/76571 A2 | 10/2001 |
| WO | WO01/83472 A1 | 11/2001 |
| WO | WO 02/003684 | * 10/2002 |
| WO | WO02/078629 A2 | 10/2002 |
| WO | WO03/028650 A2 | 4/2003 |
| WO | WO03/031412 A1 | 4/2003 |
| WO | WO03/057672 A2 | 7/2003 |
| WO | WO03/057698 A2 | 7/2003 |
| WO | WO03/059882 A1 | 7/2003 |
| WO | WO03/091220 A1 | 11/2003 |
| WO | WO2004/034963 A2 | 4/2004 |
| WO | WO2004/087158 A2 | 10/2004 |
| WO | WO2004/089942 A2 | 10/2004 |
| WO | WO2004/101603 A2 | 11/2004 |
| WO | WO2005/041979 A1 | 5/2005 |
| WO | WO2005/072713 A | 8/2005 |
| WO | WO2006/067494 A | 6/2006 |
| WO | WO2006/067496 A | 6/2006 |

OTHER PUBLICATIONS

Bromidge, Steven M., et al. "Design of [R-(Z)]-(+)-α-(Methoxyimino)-1-azabicyclo [2.2.2]octane-3-acetonitrile (SB 202026), a Functionally Selective Azabicyclic Muscarinic M1 Agonist Incorporating the N-Methoxy Imidoyl Nitrile Group as a Novel Ester Bioisostere", J. Med. Chem. (1997) 19;40(26):4268-4280.

Brown, Jason, et al. "Enriched environment and physical activity stimulate hippocampal but not olfactory bulb neurogenesis", Eur J Neurosci. (2003) 17(10):2042-2046.

Cameron, H.A., et al. "Adult neurogenesis is regulated by adrenal steroids in the dentate gyrus", Neuroscience (1994) 61 (2):203-209.

Cao, Y, et al. "Synthesis and biological characterization of 1-methyl-1,2,5,6-tetrahydropyridyl-1,2,5-thiadiazole derivatives as muscarinic agonists for the treatment of neurological disorders", J. Med. Chem (2003) 46(20):4273-4286.

Camps, P., et al. "Cholinergic Drugs in Pharmacotherapy of Alzheimer's Disease", Minireviews in Medicinal Chemistry (2002) 2:11-25.

Eglen, Richard M., et al. "Selective Muscarinic Receptor Agonist and Antagonists", Pharmacol. Toxicol. (1996) 78:59-68.

Eisch, Amelia, J., et al. "Drug dependence and addiction II: Adult neurogenesis and drug addiction", Am J Psychiatry (2004) 161(3):426.

Fisher, Abraham "Muscarinic Receptor Agonists in Alzheimer's Disease—More Than Just Symptomatic Treatment?", CNS Drugs (1999) 12(3): 197-214.

Fujimoto, J.M., et al. Intracerebroventricular Physostigmine-Induced Analgesia: Enhancement by Naloxone, β-Funaltrexamine and Nor-Binaltorphimine and Antagonism by Dynorphin A (1-17)[1], Journal of Pharmacology and Experimental Therapeutics (1989) 251(3):1045-1052.

Fujimoto, J.M., et al. "Spinal Dynorphin A (1-17): Possible Mediator of Antianalgesic Action", Neuropharmacology (1990) 29(7):609-617.

Gage, F.H., et al. "Adult brain neurogenesis and psychiatry: a novel theory of depression", Molecular Psychiatry. (2000) 5(3):262-269.

Gould, Elizabeth, et al. "Neurogenesis in the neocortex of adult primates", Science. (1999) 286(5439):548-552.

Harries, M.H., et al. "The profile of sabcomeline (SB 202026), a functionally selective $M_1$ receptor partial agonist, in the marmoset", British J. Pharm. (1998) 124:409-415.

Hetzler, Bruce E., et al. "Effects of Ketamine, Naloxone, and POhysostigmine on Flash Evoked Potentials in Rat Superior Colliculus", Pharmacology Biochemistry & Behavior (1989) 32(2):511-518.

Jones, Carrie K., et al. "Pharmacologic Interactions between the Muscarinic Cholinergic and Dopaminergic Systems in the Modulation of Prepulse Inhibition in Rats", The Journal of Pharmacology and Experimental Therapeutics (2005) 312(3):1055-1063.

Kotani, S., et al. "Pharmacological Evidence of Cholinergic Involvement in Adult Hippocampal Neurogenesis in Rats", *Neuroscience* (2006), doi: 10.1016/j.neuroscience.2006.06.035, pp. 1-10.

Kokoeva, Maia V., et al. "Neurogenesis in the Hypothalamus of Adult Mice: Potential Role in Energy Balance", *Science* (2005) 310:679-683.

Kuhn, H. George, et al. "Neurogenesis in the gentate gyrus of the adult rat: Age-related decrease neuronal progenitor proliferation", *Neurosci.* (1996) 16(6):2027-2033.

Li, Z., et al. "Reversal of morphine-induced memory impairment in mice by withdrawal in Morris water maze: Possible involvement of cholinergic system", *Pharmacology, Biochemistry and Behavior* (2001) 68(3):507-513.

Malberg, Jessica E., et al. "Chronic antidepressant increases neurogenesis in adult rat hippocampus", *J Neurosci.* (2000) 20(24):9104-9110.

McEwen, Bruce S., et al. "Hippocampal remodeling and damage by corticosteroids: Implications for mood disorders", *Neuropsychopharmacology.* (1999) 21(4):474-84.

Mohapel, Paul, et al. "Forebrain acetylcholine regulates adult hippocampal neurogenesis and learning", *Neurobiology of Aging* (2005) 26:939-946.

Moltzen, Ejner K., et al. "Bioisosteres of Arecoline: 1,2,3,6-Tetrahydro-5-pyridyl-Substituted and 3-Piperidyl-Substituted Derivatives of Tetrazoles and 1,2,3-Triazoles. Synthesis and Muscarinic Activity", *J. Med Chem.* (1994) 37(24):4085-4099s.

Nordvall, Gunnar, et al. "Analogues of the Muscarinic Agent 2'-Methylspiro[1-azabicyclo[2.2.2]octane-3,4'-[1,3]dioxolane]: Synthesis and Pharmacology", *J. Med. Chem.* (1992) 35:1541.

Santarelli, Luca, et al. "Requirement of hippocampal neurogenesis for the behavioral effects of antidepressants", *Science.* (2003) 301(5634):805-809.

Sarlis, N.J., et al. "The potency of antagonistic effects of physostigmine and naloxone, but not flumazenil, on midazolam-induced sleep are dependent upon administration timing", *European Journal of Pharmacology* (1990) 183(6):2356-2357.

van Praag, Henriette, et al. "Running enhances neurogenesis, learning and long-term potentiation in mice", *Proc Natl Acad Sci U S A.* (1999) 96(23):13427-13431.

Vogel, Gretchen "Does Brain Cell Growth Drive Weight Loss?", *Science* (2005) 310:602.

Walker, David L., et al. "Naloxone modulates the behavioral effects of cholinergic agonists and agntagonists", *Psychopharmacology* (1991) 105(1):57-62.

Wanibuchi, Fumikazu, et al. "Pharmacological studies on novel muscarinic agonist, 1-oxa-8-azaspiro[4.5]decane derivatives, YM796 and YM954", *Eur. J. Pharmacol.* (1990) 187:479- 486.

Ward, John S., et al. "Functionally Selective $M_1$ Muscarinic Agonists. 3. Side Chains and Azacycles Contributing to Functional Muscarinic Selectivity Among Pyrazinylazacycles", *J. med. Chem.* (1995) 38:3469.

Wermuth, Camille G., et al. "SR 46559 A and Related Aminoopyridazines are Potent Muscarinic Agonists With No Cholinergic Syndrome", *Bioorg. Med. Chem. Lett.* (1992) 2:833-838.

Wermuth, Camille G., et al. "Aminopyridazines—An Alternative Route to Potent Muscarinic Agonists With No Cholinergic Syndrome", *II Farmaco* (1993) 48(2):253-274.

Yamato, Shigeru, et al. "Itopride enhances distention-induced colonic peristalsis in guinea-pig: Simultaneous measurement of wall movement and intraluminal flow", *Gastroenterology* (2005) 128(4), Suppl2, p. A277.

Yehuda, Rachel, et al. "Enhanced brain cell proliferation following early adrenalectomy in rats", *J Neurochem.* (1989) 53(1):241-248.

\* cited by examiner

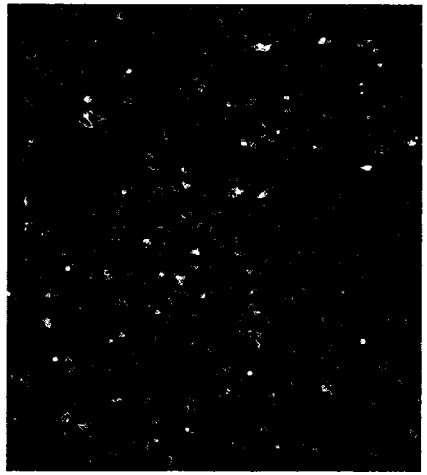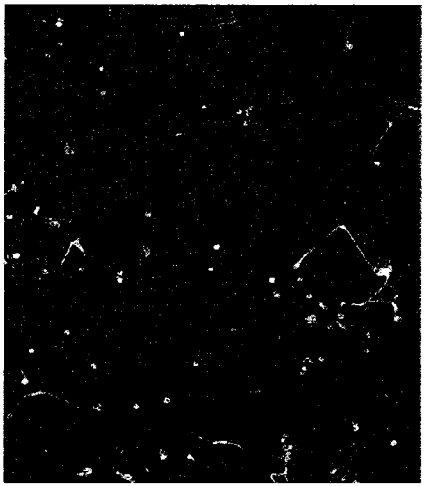
Figure 5

Figure 12

| Dose | New Neurons % vs. Vehicle |
|---|---|
| .01 mg/kg | +20% |
| .05 mg/kg | +18% |

Figure 13
A
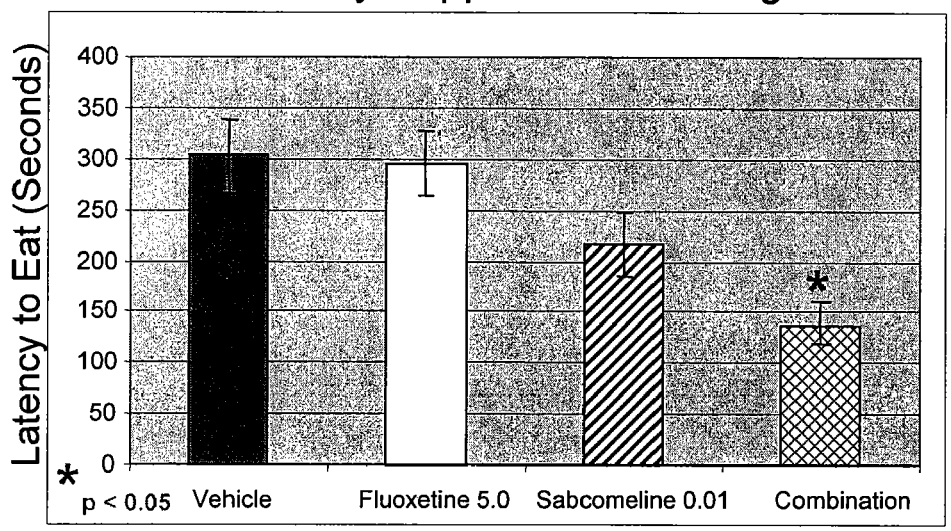
B
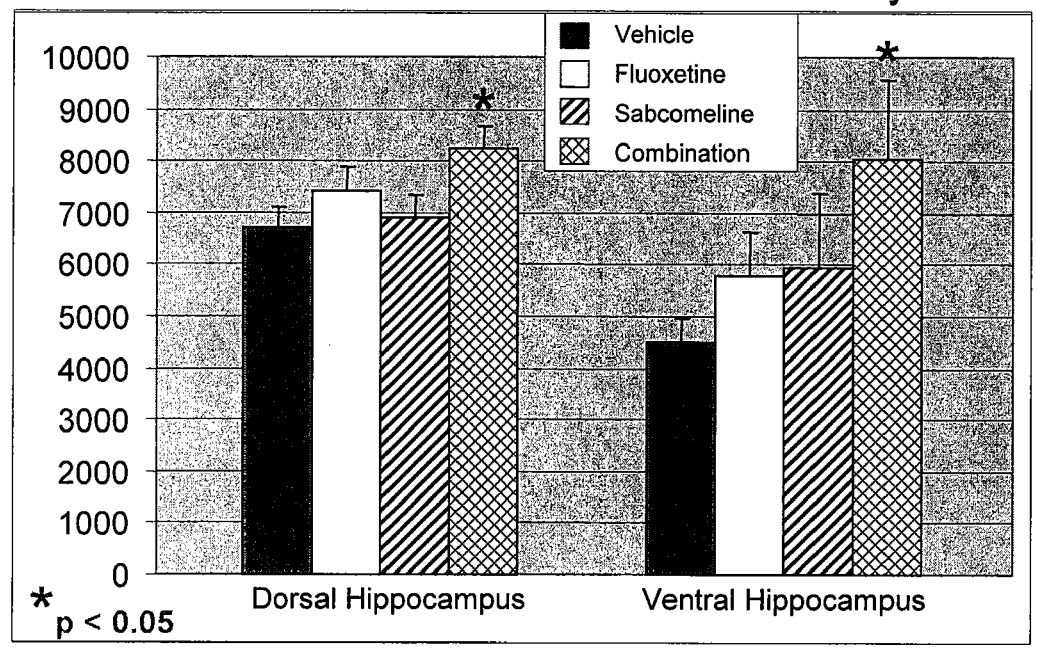

METHODS OF TREATING PSYCHIATRIC CONDITIONS COMPRISING ADMINISTRATION OF MUSCARINIC AGENTS IN COMBINATION WITH SSRIS

CROSS-REFERENCES TO RELATED APPLICATIONS

This application claims benefit of priority under 35 U.S.C. §119(e) from U.S. Provisional Patent Applications 60/711,846, filed Aug. 26, 2005; 60/727,127, filed Oct. 14, 2005; 60/738,133, filed Nov. 17, 2005; and 60/803,826, filed Jun. 2, 2006; all four of which are hereby incorporated by reference as if fully set forth.

FIELD OF THE DISCLOSURE

The instant disclosure relates to methods for treating diseases and conditions of the central and peripheral nervous system by stimulating or increasing neurogenesis via modulation of muscarinic receptor activity, including via inhibition of acetylcholine esterase (AChE) activity in combination with another neurogenic agent. The disclosure includes methods based on the application of a neurogenesis modulating agent having activity against muscarinic receptors and/or an AChE inhibitor with another neurogenic agent to stimulate or activate the formation of new nerve cells.

BACKGROUND OF THE DISCLOSURE

Neurogenesis is a vital process in the brains of animals and humans, whereby new nerve cells are continuously generated throughout the life span of the organism. The newly born cells are able to differentiate into functional cells of the central nervous system and integrate into existing neural circuits in the brain. Neurogenesis is known to persist throughout adulthood in two regions of the mammalian brain: the subventricular zone (SVZ) of the lateral ventricles and the dentate gyrus of the hippocampus. In these regions, multipotent neural progenitor cells (NPCs) continue to divide and give rise to new functional neurons and glial cells (for review Gage 2000). It has been shown that a variety of factors can stimulate adult hippocampal neurogenesis, e.g., adrenalectomy, voluntary exercise, enriched environment, hippocampus dependent learning and anti-depressants (Yehuda 1989, van Praag 1999, Brown J 2003, Gould 1999, Malberg 2000, Santarelli 2003). Other factors, such as adrenal hormones, stress, age and drugs of abuse negatively influence neurogenesis (Cameron 1994, McEwen 1999, Kuhn 1996, Eisch 2004).

Muscarinic cholinergic receptors mediate the effects of the neurotransmitter acetylcholine in the central and peripheral nervous systems. In the CNS, muscarinic receptors play a central role in mediating cognitive function and are abundant in the forebrain, including the dentate gyrus of the hippocampus and the cerebral cortex. In the PNS, muscarinic receptors mediate parasympathetic activity. Muscarinic receptors are also involved in mediating the actions of acetylcholine on certain organs that are responsive to parasympathetic cholinergic stimulation; for example, they affect the contractibility of smooth muscle in the gastrointestinal tract, the secretion of gastric acid, the force and rate of heart muscle contraction, the secretory activity of exocrine glands that receive parasympathetic innervation, such as the salivary glands, and the constriction of bronchial tissue.

Five sub-types of muscarinic receptors have been characterized, and are designated m1, m2, m3, m4, and m5. m1 receptors are found in the CNS and peripheral ganglia, m2 receptors are found on cardiac cells and in the brainstem, m3 receptors are found in smooth muscle, endocrine (e.g., the pancreas) and exocrine glands (e.g., the lacrimal glands), and the cerebral cortex, m4 receptors are found primarily in the neostriatum, and m5 receptors are found primarily in the substantia nigra. Muscarinic receptors are G-protein coupled receptors (GPCRs), with the activity of the m1, m3 and m5 receptors mediated by the phosphoinositide second-messenger system, and the m2 and m4 receptors linked to the adenylate cyclase second messenger system.

Compounds with activity against muscarinic receptors have been studied for the treatment of conditions linked to cholinergic dysfunction, such as Alzheimer's Disease, which is associated with the degeneration of cholinergic neurons in the forebrain. Clinical testing has revealed a high degree of debilitating, dose-limiting side effects associated with compounds active against the m2 and m3 receptor subtypes, including cardiovascular and gastrointestinal side effects. In contrast, compounds that are selective for m1 receptors, or m1 and m4 receptors have generally been found to have better clinical profiles, with enhanced efficacy and decreased side effects. To date, there is has been little research regarding the use of muscarinic compounds to treat diseases not characterized by or substantially resulting from cholinergic dysfunction.

Acetylcholinesterase, or AChE, is also known as erythrocyte (or RBC) cholinesterase and acetylcholine acetylhydrolase. It is classified at EC 3.1.1.7 and is found in various locations, including the blood and neural synapses. AChE catalyzes hydrolysis of the neurotransmitter acetylcholine into choline and acetic acid where acetylcholine is a pan-muscarinic and pan-nicotinic receptor ligand. The hydrolysis reaction reaction permits an activated cholinergic neuron to return to a resting state.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

BRIEF SUMMARY OF THE DISCLOSURE

Disclosed herein are compositions and methods for the prophylaxis and treatment of diseases, conditions and injuries of the central and peripheral nervous systems by modulating neurogenesis, including stimulating or increasing the generation of neurons. Aspects of the methods, and activities of the compositions, include modulating neurogenesis in cases of a disease, disorder, or condition of the nervous system. Embodiments of the disclosure include methods of treating a neurodegenerative disorder, neurological trauma including brain or central nervous system trauma and/or recovery therefrom, depression, anxiety, psychosis, learning and memory disorders, and ischemia of the central and/or peripheral nervous systems.

In one aspect, methods of modulating, such as by stimulating or increasing, neurogenesis are disclosed. The neurogenesis may be at the level of a cell or tissue. The cell or tissue may be present in an animal subject or a human being, or alternatively be in an in vitro or ex vivo setting. In some embodiments, neurogenesis is stimulated or increased in a neural cell or tissue, such as that of the central or peripheral nervous system of an animal or human being. In cases of an animal or human, the methods may be practiced in connection with one or more disease, disorder, or condition of the nervous system as present in the animal or human subject. Thus, embodiments disclosed herein include methods of treating a disease, disorder, or condition by administering at least one neurogenesis modulating agent having activity against muscarinic receptors (hereinafter referred to as a "muscarinic agent"). The muscarinic agent may be used alone or in combination with one or more additional neurogenic agents.

While a muscarinic agent may be considered a "direct" agent in that it has direct activity against a muscarinic receptor by interactions therewith, the disclosure includes a muscarinic agent that may be considered an "indirect" agent in that it does not directly interact with a muscarinic receptor. Thus, an indirect agent acts on a muscarinic receptor indirectly, or via production, generation, stability, or retention of an intermediate agent which directly interacts with a muscarinic receptor. In other embodiments, an indirect agent may be one that increases the amount of choline or available choline, such as by increasing choline synthesis as a non-limiting example.

In some embodiments, an indirect agent is an inhibitor of AChE activity. Like a direct muscarinic agent, an indirect agent may be used alone or in combination with one or more additional neurogenic agents, as described herein. An AChE inhibitor may be a cholinergic agonist, such as an inhibitor that suppresses the enzymatic activity of AChE. In some embodiments, an AChE inhibitor binds an AChE active site.

An additional neurogenic agent as described herein may be another direct muscarinic agent, another indirect muscarinic agent (such as AChE inhibitor), or a neurogenic agent that does not act, directly or indirectly, through a muscarinic receptor. Thus in some embodiments, an additional neurogenic agent is one that acts, directly or indirectly, through a mechanism other than a muscarinic receptor.

In one aspect, methods of modulating, such as by stimulating or increasing, neurogenesis are disclosed. The neurogenesis may be at the level of a cell or tissue. The cell or tissue may be present in an animal subject or a human being, or alternatively be in an in vitro or ex vivo setting. In some embodiments, neurogenesis is stimulated or increased in a neural cell or tissue, such as that of the central or peripheral nervous system of an animal or human being. In cases of an animal or human, the methods may be practiced in connection with one or more disease, disorder, or condition of the nervous system as present in the animal or human subject. Thus, embodiments disclosed herein include methods of treating a disease, disorder, or condition by administering a muscarinic agent alone or in combination with another neurogenic agent, as described herein. The additional neurogenic agent may be another muscarinic agent (direct or indirect) or a neurogenic agent that acts through a mechanism independent from a muscarinic receptor.

In another aspect, methods of using chemical entities as muscarinic agents to modulate, such as by increasing, neurogenesis are disclosed. In some embodiments, a chemical entity used as a muscarinic agent is a therapeutically or pharmaceutically acceptable reversible AChE inhibitor. Alternatively, an acceptable irreversible AChE inhibitor may also be used in some embodiments of the disclosure. Additional embodiments comprise an inhibitor that is a tertiary amine which crosses the blood brain barrier.

Non-limiting examples of AChE inhibitors as a muscarinic agent include an organophosphate (such as metrifonate or echothiophate), an aminoacridine (such as tacrine), a carbamate (such as physostigmine or neostigmine or rivastigmine) a phenanthrine derivative (such as galantamine), or a piperidine derivative (such as donepezil) that has neurogenic activity. In other embodiments, a carbamate, such as a quaternary amine (and pyridostigmine, ambenonium and demarcarium as non-limiting examples) are disclosed for use in the practice of the invention. Other non-limiting examples of an AChE inhibitor with neurogenic activity include itopride, (−)-huperzine A, and phenserine. A yet additional embodiment of an AChE inhibitor is edrophonium.

Embodiments described herein include a combination of more than one of the muscarinic agents disclosed herein or known to the skilled person. Of course a neurogenic muscarinic agent may be used, either alone or in combination with one or more additional muscarinic agents or other neurogenic agents. Compositions disclosed herein include such combinations of muscarinic agents, including AChE inhibitor(s) as a non-limiting embodiment, and other neurogenic agent(s).

In another aspect, the disclosed methods include identifying a patient suffering from one or more diseases, disorders, or conditions, or a symptom thereof, and administering to the patient a muscarinic agent, alone or in combination with another neurogenic agent, as described herein. In some embodiments, a method including identification of a subject as in need of an increase in neurogenesis, and administering to the subject one or more muscarinic agents is disclosed herein. In other embodiments, the subject is a patient, such as a human patient.

Additional embodiments describe a method including administering a muscarinic agent, alone or in combination with another neurogenic agent, to a subject exhibiting the effects of insufficient amounts of, or inadequate levels of, neurogenesis. In some embodiments, the subject may be one that has been subjected to an agent that decreases or inhibits neurogenesis. Non-limiting examples of an inhibitor of neurogenesis include opioid receptor agonists, such as a mu receptor subtype agonist like morphine. In a related manner, a method provides for administering a muscarinic agent, alone or in combination with another neurogenic agent, to a subject or person that will be subjected to an agent that decreases or inhibits neurogenesis. Non-limiting embodiments include those where the subject or person is about to be administered morphine or another opioid receptor agonist, like another opiate, and so about to be subject to a decrease or inhibition of neurogenesis. Non-limiting examples include administering a muscarinic agent, alone or in combination with another neurogenic agent, to a subject before, simultaneously with, or after the subject is administered morphine or other opiate in connection with a surgical procedure.

Also disclosed are methods for preparing a population of neural stem cells suitable for transplantation, comprising culturing a population of neural stem cells (NSCs) in vitro, and contacting the cultured neural stem cells with at least one muscarinic agent, optionally in combination with another muscarinic agent, such as an AChE inhibitor, and/or another neurogenic agent. In some embodiments, the stem cells are prepared and then transferred to a recipient host animal or human. Non-limiting examples of preparation include 1) contact with a muscarinic agent, optionally in combination with another muscarinic agent, such as an AChE inhibitor, and/or another neurogenic agent, until the cells have undergone neurogenesis, such as that which is detectable by visual inspection or cell counting, or 2) contact with a muscarinic agent, such as an AChE inhibitor, optionally in combination with another muscarinic agent and/or another neurogenic agent, until the cells have been sufficiently stimulated or induced toward or into neurogenesis. The cells prepared in such a non-limiting manner may be transplanted to a subject, optionally with simultaneous, nearly simultaneous, or subsequent administration of a neurogenic agent, or a muscarinic agent, such as an AChE inhibitor, to the subject. While the neural stem cells may be in the form of an in vitro culture or cell line, in other embodiments, the cells may be part of a tissue which is subsequently transplanted into a subject.

In yet another aspect, the disclosure includes methods of modulating, such as by stimulating or increasing, neurogenesis in a subject by administering a muscarinic agent, optionally in combination with another muscarinic agent, such as an AChE inhibitor, and/or another neurogenic agent. In some embodiments, the neurogenesis occurs in combination with the stimulation of angiogenesis which provides new cells with access to the circulatory system.

The details of additional embodiments are set forth in the accompanying drawings and the description below. Other features, objects, and advantages of the embodiments will be apparent from the drawings and detailed description, and from the claims.

BRIEF DESCRIPTION OF THE DRAWINGS

FIG. 5 is a series of immunofluorescent microscopic images of monolayers of human neural stem cells (hNSC) after immunohistochemistry staining with the neuronal marker TUJ-1 (blue), the astrocyte marker GFAP (red), and a nuclear cell marker (Hoechst 33342) (example 5). The upper left image is a negative control (basal media), the upper middle image is a neuronal positive control (basal media plus a known promoter of neuronal differentiation), and the upper right image is an astrocyte positive control (basal media plus a known promoter of astrocyte differentiation). The lower image shows the effect of sabcomeline on hNSC differentiation.

FIG. 12 shows the effect of chronic dosing of rats with Sabcomeline on the differentiation of neural progenitor cells into mature neuron within the subgranular zone of the dentate gyrus. Chronic Sabcomeline treatment resulted in a 20 and 18 percent increase at 0.01 and 0.05 mg/kg/day, respectively.

FIG. 13A shows the effect of chronic dosing of rats with sabcomeline, fluoxetine, or a combination of both agents in the novelty suppressed feeding depression model (gray: vehicle; white: 5.0 mg/kg fluoxetine; hatched: 0.01 mg/kg sabcomeline; cross-hatched: 5.0 mg/kg Fluoxetine and 0.01 mg/kg sabcomeline). The combination of fluoxetine with sabcomeline resulted in significantly enhanced performance in the assay relative to vehicle or either agent alone. FIG. 13B shows the effect of acute dosing of rats (injection once daily for five days) with sabcomeline, fluoxetine, or a combination of both agents on neural cell proliferation within the dentate gyrus (gray: vehicle; white: 5.0 mg/kg fluoxetine; hatched: 0.01 mg/kg sabcomeline; cross-hatched: 5.0 mg/kg Fluoxetine and 0.01 mg/kg sabcomeline) in the dorsal hippocampus and the ventral hippocampus. Results are presented as the mean number of Brdu-positive cells per cubic mm. The combination of sabcomeline and fluoxetine resulted in a significant increase in proliferation indicating increased neurogenesis.

DETAILED DESCRIPTION OF MODES OF PRACTICE

Figure 1:
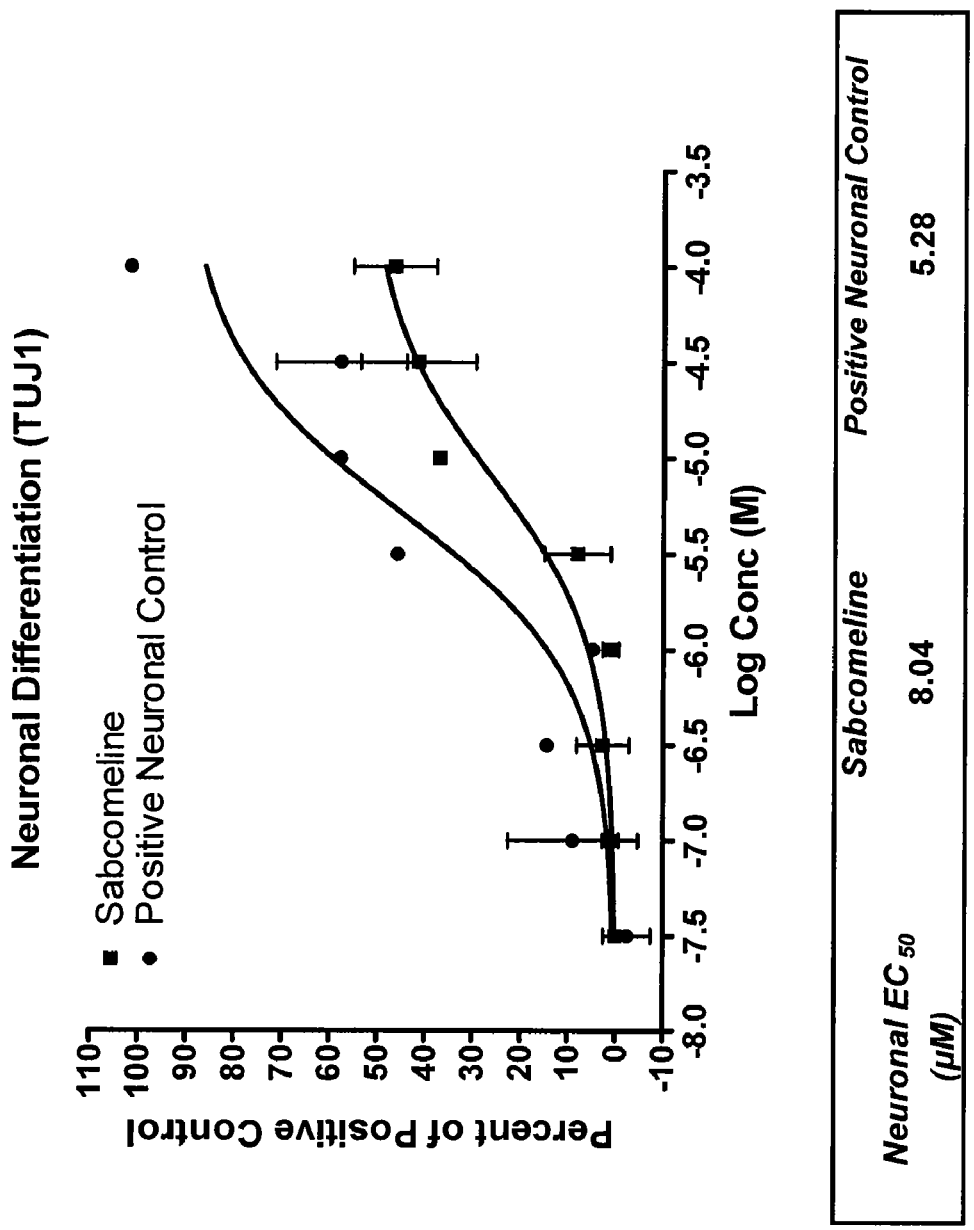
FIG. 1 is a dose-response curve showing effect of the muscarinic agent sabcomeline on neuronal differentiation. Data is presented as the percentage of the neuronal positive control, with basal media values subtracted. $EC_{50}$ was observed at a sabcomeline concentration of 8.04 µM, compared to 5.28 µM for the positive control.

"Neurogenesis" is defined herein as proliferation, differentiation, migration and/or survival of a neural cell in vivo or in vitro. In various embodiments, the neural cell is an adult, fetal, or embryonic neural stem cell or population of cells. The cells may be located in the central nervous system or elsewhere in an animal or human being. The cells may also be in a tissue, such as neural tissue. In some embodiments, the neural cell is an adult, fetal, or embryonic progenitor cell or population of cells, or a population of cells comprising a mixture of stem cells and progenitor cells. Neural cells include all brain stem cells, all brain progenitor cells, and all brain precursor cells. Neurogenesis includes neurogenesis as it occurs during normal development, as well as neural regeneration that occurs following disease, damage or therapeutic intervention, such as by the treatment described herein.

A "neurogenic agent" is defined as a chemical agent or reagent that can promote, stimulate, or otherwise increase the amount or degree or nature of neurogenesis in vivo or ex vivo or in vitro relative to the amount, degree, or nature of neurogenesis in the absence of the agent or reagent. In some embodiments, treatment with a neurogenic agent increases neurogenesis if it promotes neurogenesis by at least about 5%, at least about 10%, at least about 25%, at least about 50%, at least about 100%, at least about 500%, or more in comparison to the amount, degree, and/or nature of neurogenesis in the absence of the agent, under the conditions of the method used to detect or determine neurogenesis. As described herein, a muscarinic agent, such as an AChE inhibitor, that promotes, stimulates, or otherwise increases the amount or degree or nature of neurogenesis is a neurogenic agent.

The term "astrogenic" is defined in relation to "astrogenesis" which refers to the activation, proliferation, differentiation, migration and/or survival of an astrocytic cell in vivo or in vitro. Non-limiting examples of astrocytic cells include astrocytes, activated microglial cells, astrocyte precursors and potentiated cells, and astrocyte progenitor and derived cells. In some embodiments, the astrocyte is an adult, fetal, or embryonic astrocyte or population of astrocytes. The astrocytes may be located in the central nervous system or elsewhere in an animal or human being. The astrocytes may also be in a tissue, such as neural tissue. In some embodiments, the astrocyte is an adult, fetal, or embryonic progenitor cell or population of cells, or a population of cells comprising a mixture of stem and/or progenitor cells, that is/are capable of developing into astrocytes. Astrogenesis includes the proliferation and/or differentiation of astrocytes as it occurs during normal development, as well as astrogenesis that occurs following disease, damage or therapeutic intervention.

The term "stem cell" (or neural stem cell (NSC)), as used herein, refers to an undifferentiated cell that is capable of self-renewal and differentiation into neurons, astrocytes, and/or oligodendrocytes.

The term "progenitor cell" (e.g., neural progenitor cell), as used herein, refers to a cell derived from a stem cell that is not itself a stem cell. Some progenitor cells can produce progeny that are capable of differentiating into more than one cell type.

The term "muscarinic agent" as used herein includes a neurogenic agent, as defined herein, that elicits an observable response upon contacting a muscarinic receptor. "Muscarinic agents" useful in the methods described herein include compounds or agents that, under certain conditions, may act as: agonists (i.e., agents able to elicit one or more biological responses of a muscarinic receptor); partial agonists (i.e., agents able to elicit one or more biological responses of a receptor to a less than maximal extent, e.g., as defined by the response of the receptor to an agonist); antagonists (agents able to inhibit one or more characteristic responses of a muscarinic receptor, for example, by competitively or non-competitively binding to the muscarinic receptor, a ligand of the receptor, and/or a downstream signaling molecule); and/or inverse agonists (agents able to block or inhibit a constitutive activity of a muscarinic receptor) of one or more subtypes of muscarinic receptors. For example, the muscarinic agent alvameline, described in more detail below, is known to have agonist properties with respect to $m_1$ receptors and antagonist properties with respect to m2 and/or $m_3$ receptors under certain conditions.

In some embodiments, the muscarinic agent(s) used in the methods described herein has "selective" activity under certain conditions against one or more muscarinic receptor subtypes with respect to the degree and/or nature of activity against one or more other muscarinic receptor subtypes. For example, in some embodiments, the muscarinic agent has an agonist effect against one or more subtypes, and a much weaker effect or substantially no effect against other subtypes. As another example, a muscarinic agent used in the methods described herein may act as an agonist at one or more muscarinic receptor subtypes and as antagonist at one or more other muscarinic receptor subtypes. In some embodiments, muscarinic agents have activity against $m_1$ muscarinic receptors, while having substantially lesser activity against one or more other muscarinic receptor subtypes. In certain embodiments, selective activity of one or more muscarinic agonists results in enhanced efficacy, fewer side effects, lower effective dosages, less frequent dosing, or other desirable attributes.

In some embodiments, the muscarinic agent(s) used in the methods described herein are substantially inactive with respect to other receptors (i.e., non-muscarinic receptors), such as 5-HT receptors, dopamine receptors, epinephrine receptors, histamine receptors, glutamate receptors, and the like. However, in some embodiments, muscarinic agent(s) are active against one or more additional receptor subtypes.

In other embodiments, a muscarinic agent as used herein includes a neurogenesis modulating agent, as defined herein, that elicits an observable neurogenic response by producing, generating, stabilizing, or increasing the retention of an intermediate agent which, when contacted with a muscarinic receptor, results in the neurogenic response. As used herein, "increasing the retention of" or variants of that phrase or the term "retention" refer to decreasing the degradation of, or increasing the stability of, an intermediate agent. As a non-limiting example, and where acetylcholine is the intermediate agent, an AChE inhibitor increases the retention of acetylcholine by decreasing its degradation by AChE.

An "AChE inhibitor" is a ligand that binds AChE and has (acetylcholine, or ACh, receptor stimulating) activity. An AChE inhibitor may be a cholinergic agonist or otherwise contribute to cholinergic tone by allowing more ACh to be present to stimulate receptor activity. In some embodiments, an AChE inhibitor may act by inhibiting AChE enzymatic activity.

In some embodiments, an AChE inhibitor or cholinergic agonist stimulates ACh receptor activity by an increase of at least about 5%, at least about 10%, at least about 15%, at least about 20%, at least about 30%, at least about 50%, at least about 75%, at least about 100%, at least about 200%, at least about 300%, at least about 400%, or at least about 500% or more than the amount of receptor activity in the absence of the AChE inhibitor. AChE inhibitors that lack ACh receptor antagonist may be advantageously used in the disclosed.

The disclosed embodiments include methods of modulating, such as by increasing, neurogenesis by contacting one or more neural cells with a muscarinic agent, such as an AChE inhibitor, optionally in combination with another muscarinic agent and/or another neurogenic agent. The amount of a muscarinic agent, such as an AChE inhibitor, optionally in combination with another muscarinic agent and/or another neurogenic agent, may be selected to be effective to produce an improvement in a treated subject, or detectable neurogenesis in vitro. In some embodiments, the amount is one that also minimizes clinical side effects seen with administration of the inhibitor to a subject. The amount of a muscarinic agent, such as an AChE inhibitor, used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less of the maximum tolerated dose for a subject, such as where another muscarinic agent and/or another neurogenic agent is used in combination. This is readily determined for each muscarinic agent that has been in clinical use or testing, such as in humans.

In some cases, where an amount or concentration of a muscarinic agent, optionally in combination with another neurogenic agent, results in an undesirable level of astrogenic activity, the invention includes methods of using a muscarinic agent at a sub-astrogenic amount or concentration so as to reduce or avoid the inhibition of beneficial neurogenesis induced by the agent. In some embodiments, the sub-astrogenic amount of a muscarinic agent is used in combination with an amount of a neurogenic sensitizing agent, such as one which has no detectable or measurable astrogenic activity. As a non-limiting example, a subject in need of the combination is administered a sub-astrogenic amount of a muscarinic agent and an amount of a neurogenic sensitizing agent.

A sub-astrogenic amount or concentration of a muscarinic agent is an effective one which does not induce an unacceptable level or degree of astrogenesis. A sub-astrogenic amount is thus less than the maximum level of astrogenesis that can be induced or stimulated by a chemical agent. In some embodiments, the sub-astrogenic amount may range from a partially astrogenic amount of a muscarinic agent to an amount wherein no measurable or detectable level of astrogenesis occurs in an assay like those described herein.

Non-limiting examples of sub-astrogenic levels include amounts which decrease the level of astrogenesis, relative to the amount of the muscarinic agent that produces the highest levels of astrogenesis in vitro, or the maximum tolerated amount in vivo, by at least about 5%, at least about 10%, at least about 25%, at least about 50%, at least about 70%, at least about 75%, at least about 80%, at least about 82%, at least about 84%, at least about 86%, at least about 88%, at least about 90%, at least about 92%, at least about 94%, at least about 96%, at least about 98%, or at least about 99%.

The use of a reduced amount of muscarinic agent may also decrease the level of neurogenic activity provided by the agent.

The sub-astrogenic amount of a muscarinic agent may be an amount that also potentiates or sensitizes, such as by activating or inducing cells to proliferate and/or differentiate, a population of neural cells for neurogenesis when the amount of agent is used in combination with a neurogenic sensitizing agent. The degree of potentiation or sensitization for neurogenesis may be determined with use of the combination in any appropriate neurogenesis assay, including, but not limited to, the neuronal differentiation assay described herein. In some embodiments, the amount of muscarinic agent is the highest amount which produces no detectable neurogenesis in vitro but yet produces neurogenesis, or a measurable shift in efficacy in promoting neurogenesis in vitro, when used in combination with a neurogenic sensitizing agent. In other embodiments, the amount used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less of the maximum tolerated dose for a subject. Non-limiting examples of subjects include both human beings and animals in assays for behavior linked to neurogenesis. Exemplary animal assays include those described herein.

Furthermore, the sub-astrogenic amount may also be an amount that decreases or minimizes clinical side effects seen with administration of a muscarinic agent in a subject. Non-limiting examples of such side effects include headache, nervousness, light headedness, nausea, excitement, dizziness, sweating/clamminess, insomnia, vertigo, somnolence, and stomach upset.

The amount of a neurogenic sensitizing agent may be an amount selected to be effective to produce an improvement in a treated subject, or detectable neurogenesis in vitro, when used in combination with a muscarinic agent. In some embodiments, such as in the case of known neurogenic agents, the amount is one that minimizes clinical side effects seen with administration of the agent to a subject. The amount of neurogenic sensitizing agent used in vivo may be about 50%, about 45%, about 40%, about 35%, about 30%, about 25%, about 20%, about 18%, about 16%, about 14%, about 12%, about 10%, about 8%, about 6%, about 4%, about 2%, or about 1% or less of the maximum tolerated dose for a subject. This is readily determined for each neurogenic sensitizing agent that has been in clinical use or testing, such as in humans.

In other embodiments, the amount of neurogenic sensitizing agent is the highest amount which produces no detectable neurogenesis in vitro, including in animal (or non-human) models for behavior linked to neurogenesis, but yet produces neurogenesis, or a measurable shift in efficacy in promoting neurogenesis in the in vitro assay, when used in combination with a muscarinic agent. Alternative embodiments include amounts which produce about 1%, about 2%, about 4%, about 6%, about 8%, about 10%, about 12%, about 14%, about 16%, about 18%, about 20%, about 25%, about 30%, about 35%, or about 40% or more of the neurogenesis seen with the amount that produces the highest level of neurogenesis in an in vitro assay.

In another aspect, the disclosed embodiments include methods of using a muscarinic agent, such as an AChE inhibitor, optionally in combination with another muscarinic agent and/or another neurogenic agent, at a level at which neurogenesis occurs. The amount of a muscarinic agent, such as an AChE inhibitor, optionally in combination with another muscarinic agent and/or another neurogenic agent, may be any that is effective to produce neurogenesis, optionally with reduced or minimized amounts of astrogenesis. In some embodiments, the amount may be the lowest needed to produce a desired, or minimum, level of detectable neurogenesis or beneficial effect.

In methods of increasing neurogenesis by contacting cells with a muscarinic agent, such as an AChE inhibitor, optionally in combination with another muscarinic agent and/or another neurogenic agent, the cells may be in vitro or in vivo. In some embodiments, the cells are present in a tissue or organ of a subject animal or human being. In embodiments featuring use of an AChE inhibitor, it may be any that has ACh receptor stimulating activity, such as a cholinergic agonist, as described herein.

The cells are those capable of neurogenesis, such as to result, whether by direct differentiation or by proliferation and differentiation, in differentiated neuronal or glial cells. Representative, and non-limiting examples of non-muscarinic agents, such as non-AChE inhibitor, neurogenic agents for use in the disclosed embodiments are provided below.

In applications to an animal or human being, the embodiments relate to a method of bringing cells into contact with a muscarinic agent, such as an AChE inhibitor, optionally in combination with another muscarinic agent and/or another neurogenic agent, in effective amounts to result in an increase in neurogenesis in comparison to the absence of the muscarinic agent or combination. A non-limiting example is in the administration of the muscarinic agent to the animal or human being. Such contacting or administration may also be described as exogenously supplying the muscarinic agent to a cell or tissue.

In some embodiments, the term "animal" or "animal subject" refers to a non-human mammal, such as a primate, canine, or feline. In other embodiments, the terms refer to an animal that is domesticated (e.g. livestock) or otherwise subject to human care and/or maintenance (e.g. zoo animals and other animals for exhibition). In other non-limiting examples, the terms refer to ruminants or carnivores, such as dogs, cats, birds, horses, cattle, sheep, goats, marine animals and mammals, penguins, deer, elk, and foxes.

The disclosed embodiments also relate to methods of treating diseases, disorders, and conditions of the central and/or peripheral nervous systems (CNS and PNS, respectively) by administering a muscarinic agent, such as an AChE inhibitor, optionally in combination with another muscarinic agent and/ or another neurogenic agent. As used herein, "treating" includes prevention, amelioration, alleviation, and/or elimination of the disease, disorder, or condition being treated or one or more symptoms of the disease, disorder, or condition being treated, as well as improvement in the overall well being of a patient, as measured by objective and/or subjective criteria. In some embodiments, treating is used for reversing, attenuating, minimizing, suppressing, or halting undesirable or deleterious effects of, or effects from the progression of, a disease, disorder, or condition of the central and/or peripheral nervous systems. In other embodiments, the method of treating may be advantageously used in cases where additional neurogenesis would replace, replenish, or increase the numbers of cells lost due to injury or disease as non-limiting examples.

The amount of a muscarinic agent, such as an AChE inhibitor, optionally in combination with another muscarinic agent and/or another neurogenic agent, may be any that results in a measurable relief of a disease condition like those described herein. As a non-limiting example, an improvement in the Hamilton depression scale (HAM-D) score for depression may be used to determine (such as quantitatively) or detect (such as qualitatively) a measurable level of improvement in the depression of a subject.

Non-limiting examples of symptoms that may be treated with the methods described herein include abnormal behavior, abnormal movement, hyperactivity, hallucinations, acute delusions, combativeness, hostility, negativism, withdrawal, seclusion, memory defects, sensory defects, cognitive defects, and tension. Non-limiting examples of abnormal behavior include irritability, poor impulse control, distractibility, and aggressiveness.

In some embodiments, the muscarinic agonist is milameline (CI-979), or a compound that is structurally or functionally related to milameline. Structures, biological activity data, methods for obtaining biological activity data, methods of synthesis, modes of administration and pharmaceutical formulations for milameline and related compounds are disclosed in U.S. Pat. Nos. 4,786,648, 5,362,860, 5,424,301, 5,650,174, 4,710,508, 5,314,901, 5,356,914, and 5,356,912, all of which are herein incorporated by reference in their entirety.

In other embodiments, the muscarinic agonist is xanomeline, or a compound that is structurally or functionally related to xanomeline. Structures, biological activity data, methods for obtaining biological activity data, methods of synthesis, modes of administration and pharmaceutical formulations for xanomeline and related compounds are disclosed in U.S. Pat. Nos. 5,041,455, 5,043,345, and 5,260,314, all of which are herein incorporated by reference in their entirety.

In further embodiments, the muscarinic agent is alvameline (LU 25-109), or a compound that is functionally or structurally related to alvameline. Structures, biological activity data, methods for obtaining biological activity data, methods of synthesis, modes of administration and pharmaceutical formulations for alvameline and related compounds are disclosed in U.S. Pat. Nos. 6,297,262, 4,866,077, RE 36,374, 4,925,858, PCT Publication No. WO 97/17074, and in Moltzen et al., J Med Chem. 1994 Nov. 25;37(24):4085-99, all of which are herein incorporated by reference in their entirety.

In additional embodiments, the muscarinic agent is 2,8-dimethyl-3-methylene-1-oxa-8-azaspiro[4.5]decane (YM-796) or YM-954, or a functionally or structurally related compound. Structures, biological activity data, methods for obtaining biological activity data, methods of synthesis, modes of administration and pharmaceutical formulations for YM-796, YM-954, and related compounds are disclosed in U.S. Pat. Nos. 4,940,795, RE 34,653, 4,996,210, 5,041,549, 5,403,931, and 5,412,096, and in Wanibuchi et al., Eur. J. Pharmacol., 187, 479-486 (1990), all of which are herein incorporated by reference in their entirety.

In yet further embodiments, the muscarinic agent is cevimeline (AF102B) or a compound that is functionally or structurally related to cevimeline. Cevimeline is approved by the FDA for the treatment of symptoms of dry mouth in patients with Sjorgren's Syndrome. Structures, biological activity data, methods for obtaining biological activity data, methods of synthesis, modes of administration and pharmaceutical formulations for cevimeline and related compounds are disclosed in U.S. Pat. Nos. 4,855,290, 5,340,821, 5,580, 880 (American Home Products), and U.S. Pat. No. 4,981,858 (optical isomers of AF102B), all of which are herein incorporated by reference in their entirety.

Figure 9:
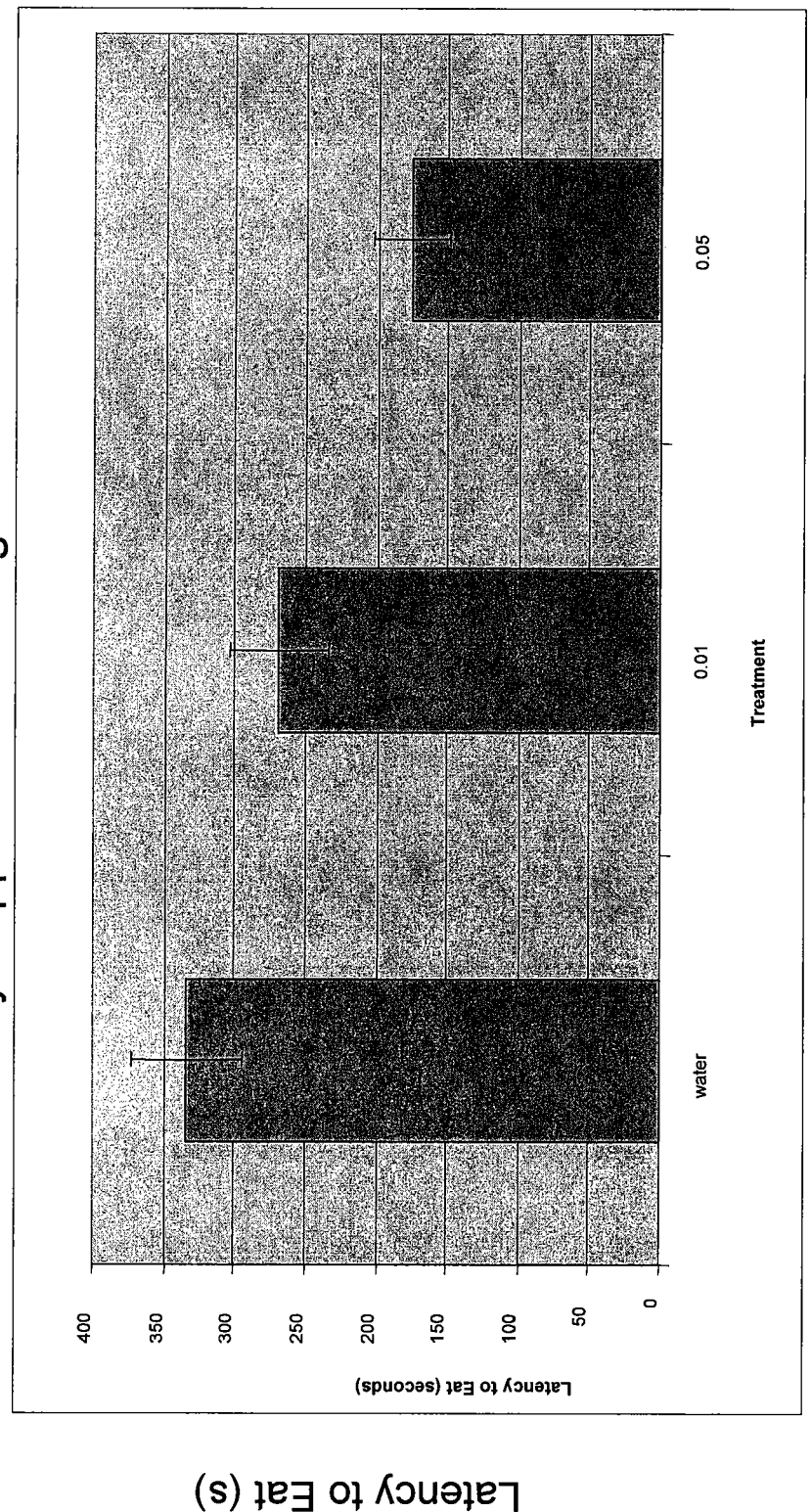
FIG. 9 shows the effect of chronic dosing of rats with sabcomeline on latency to eat in a novelty-suppressed feeding assay (left: vehicle; middle: 0.01 mg/kg; right: 0.05 mg/kg). Sabcomeline decreased the latency to eat in a dose-dependent manner, with a statistically significant decrease at 0.05 mg/kg.
Figure 10:
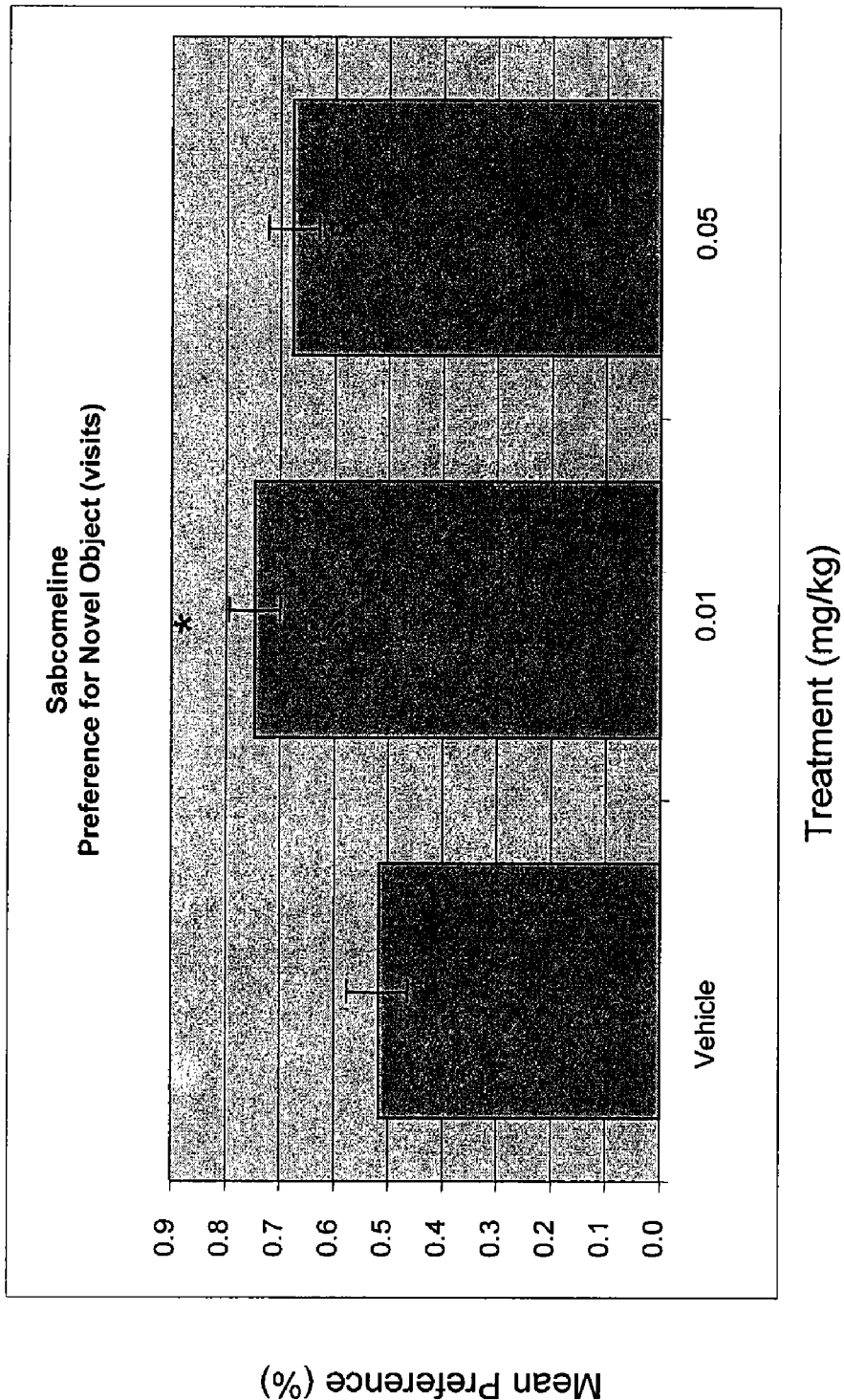
FIG. 10 shows the effect of chronic dosing of rats with sabcomeline on cognitive performance in a novel object recognition assay (left: vehicle; middle: 0.01 mg/kg; right: 0.05 mg/kg). Sabcomeline significantly enhanced performance in the assay at 0.01 mg/kg.
Figure 11:
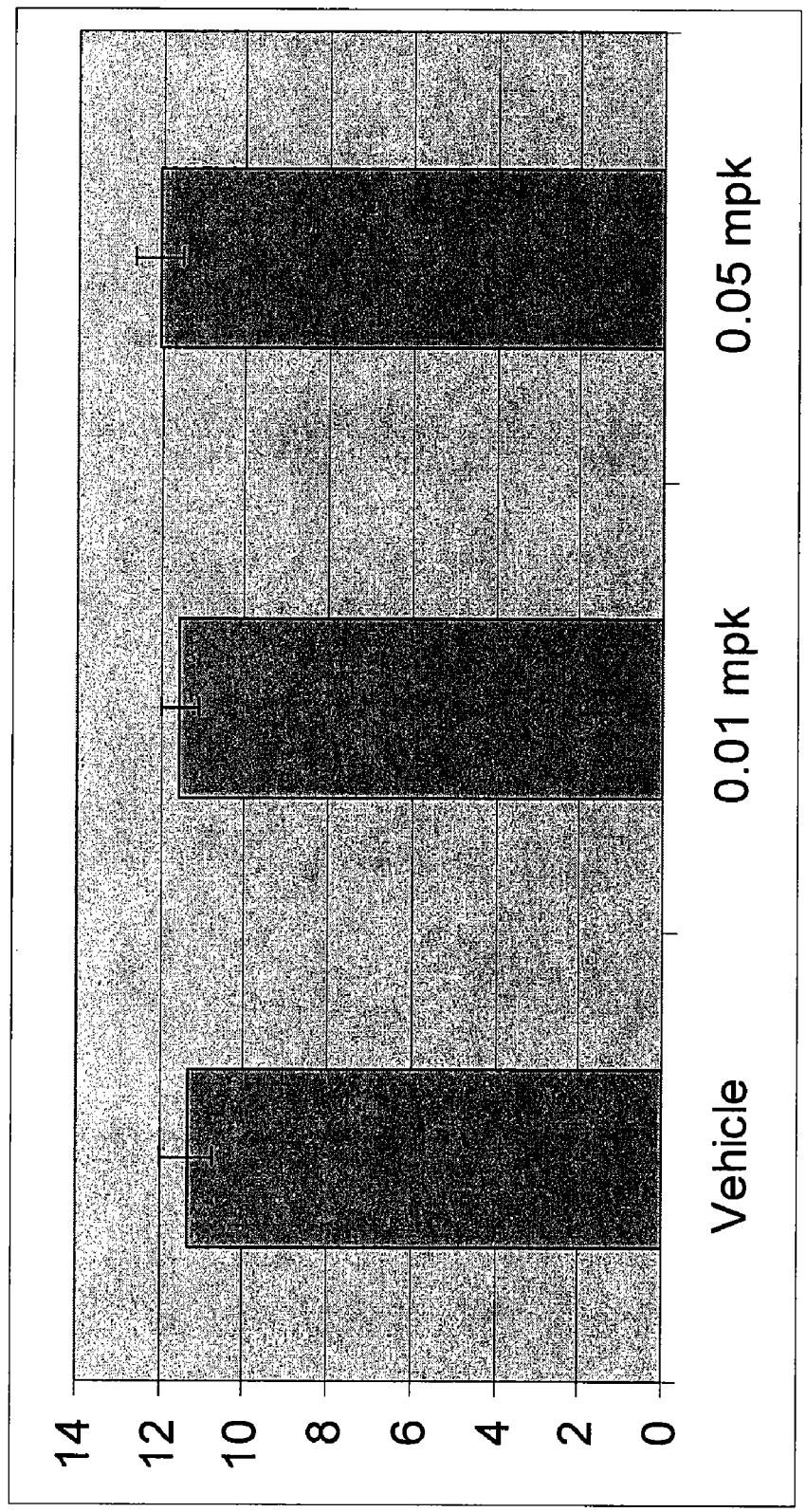
FIG. 11 shows the effect of acute dosing of rats (injection once daily for five days) with sabcomeline on neural cell proliferation within the dentate gyrus (left: vehicle; middle: 0.01 mg/kg; right: 0.05 mg/kg). Results are presented as the mean number of Brdu-positive cells per cubic mm. A dose-related increase in proliferation was observed.

In yet additional embodiments, the muscarinic agent is sabcomeline (SB 202026), or a compound that is functionally or structurally related to sabcomeline. Structures, biological activity data, methods for obtaining biological activity data, methods of synthesis, modes of administration and pharmaceutical formulations for sabcomeline and related compounds are described in U.S. Pat. Nos. 5,278,170, RE 35,593, 6,468,560, 5,773,619, 5,808,075, 5,545,740, 5,534,522, and 6,596,869, U.S. Patent Publication Nos. 2002/0127271, 2003/0129246, 2002/0150618, 2001/0018074, 2003/0157169, and 2001/0003588, Bromidge et al., J Med Chem. 19;40(26):4265-80 (1997), and Harries et al., British J. Pharm., 124, 409-415 (1998), all of which are herein incorporated by reference in their entirety. As shown in FIGS. 1-5 and 11, sabcomeline significantly enhances the proliferation, growth, and survival of human NSCs, and preferentially stimulates NSCs to differentiate along a neuronal lineage. Moreover, as shown in FIGS. 9-10, sabcomeline significantly enhances neurogenesis, reduces depressive and anxious behaviors and enhances cognitive function in vivo.

Sabcomeline, alone or in combination with one or more agents as described herein, is specifically contemplated for use in the methods and compositions as disclosed herein.

In other embodiments, the muscarinic agent is talsaclidine (WAL 2014 FU), or a compound that is functionally or structurally related to talsaclidine. Structures, biological activity data, methods for obtaining biological activity data, methods of synthesis, modes of administration and pharmaceutical formulations for talsaclidine and related compounds are disclosed in U.S. Pat. Nos. 5,451,587, 5,286,864, 5,508,405, 5,451,587, 5,286,864, 5,508,405, and 5,137,895, and in Pharmacol. Toxicol., 78, 59-68 (1996), all of which are herein incorporated by reference in their entirety.

In some embodiments, the muscarinic agent is a 1-methyl-1,2,5,6-tetrahydropyridyl-1,2,5-thiadiazole derivative, such as tetra(ethylenegiycol)(4-methoxy-1,2,5 -thiadiazol-3-yl)[3-(1-methyl-1,2,5,6-tetrahydropyrid-3-yl)-1,2,5-thiadiazol-4-yl]ether, or a compound that is functionally or structurally related to a 1-methyl-1,2,5,6-tetrahydropyridyl-1,2,5-thiadiazole derivative. Structures, biological activity data, methods for obtaining biological activity data, methods of synthesis, and other information relating to using these derivatives and related compounds as pharmaceutical agents is provided by Cao et al. ("Synthesis and biological characterization of 1-methyl-1,2,5,6-tetrahydropyridyl-1,2,5-thiadiazole derivatives as muscarinic agonists for the treatment of neurological disorders." J. Med. Chem. 46(20):4273-4286, 2003), which is herein incorporated by reference in its entirety.

In further embodiments, the muscarinic agent is besipiridine, SR-46559, L-689,660, S-9977-2, AF-102, or thiopilocarpine. The structures, biological activity data, methods for obtaining biological activity data, methods of synthesis, modes of administration and pharmaceutical formulations for these and related compounds are known in the art and/or described in the publications referenced herein.

In yet further embodiments, the muscarinic agent is an analog of clozapine or a pharmaceutically acceptable salt, ester, amide, or prodrug form thereof. In some embodiments, the analog is a diaryl[a,d]cycloheptene, such as an amino substituted form thereof. A compound that is functionally or structurally related to such analogs of clozapine may also be used in the practice of the invention. In some embodiments, the compound is N-desmethylclozapine, which has been reported to be a metabolite of clozapine and discovered to be highly neurogenic in assays as disclosed herein. Structures, biological activity data, methods for obtaining biological activity data, methods of synthesis, modes of administration and pharmaceutical formulations for these analogs and related compounds are disclosed in US 2005/0192268 and WO 05/63254, both of which are hereby incorporated by reference as if fully set forth.

In other embodiments, the muscarinic agent is an ml receptor agonist selected from 55-LH-3B, 55-LH-25A, 55-LH-30B, 55-LH-4-1A, 40-LH-67, 55-LH-15A, 55-LH-16B, 55-LH-11C, 55-LH-31A, 55-LH-46, 55-LH-47, 55-LH-4-3A, or a compound that is functionally or structurally related to one or more of these agonists. Structures, biological activity data, methods for obtaining biological activity data, methods of synthesis, modes of administration and pharmaceutical formulations for these agonists and related compounds are disclosed in US 2005/0130961 and WO 04/087158, both of which are hereby incorporated by reference as if fully set forth.

In additional embodiments, the muscarinic agent is a benzimidazolidinone derivative or a compound that is functionally or structurally related to a benzimidazolidinone derivative. The derivative or related compound may be selective for the $m_1$ and/or $M_4$ receptor subtypes. Structures, biological activity data, methods for obtaining biological activity data, methods of synthesis, modes of administration and pharmaceutical formulations for these derivatives and related compounds are disclosed in U.S. Pat. No. 6,951,849, US 2003/0100545, WO 04/089942, and WO 03/028650, all of which are hereby incorporated by reference as if fully set forth.

In yet additional embodiments, the muscarinic agent is a spiroazacyclic compound or a compound that is functionally or structurally related to a spiroazacyclic compound. In some embodiments, the compound is 1-oxa-3,8-diaza-spiro[4,5]decan-2-one. Structures, biological activity data, methods for obtaining biological activity data, methods of synthesis, modes of administration and pharmaceutical formulations for these spiroazacyclic compounds and related compounds are disclosed in U.S. Pat. No. 6,911,452 and WO 03/057698, both of which are hereby incorporated by reference as if fully set forth.

In other embodiments, the muscarinic agent is a tetrahydroquinoline analog or a compound that is functionally or structurally related to a tetrahydroquinoline analog. Structures, biological activity data, methods for obtaining biological activity data, methods of synthesis, modes of administration and pharmaceutical formulations for these spiroazacyclic compounds and related compounds are disclosed in US 2003/0176418, US 2005/0209226, and WO 03/057672, all of which are hereby incorporated by reference as if fully set forth.

In further embodiments, the agent is a muscarinic agonist or a compound that is functionally or structurally related to such an agonist. Structures, biological activity data, methods for obtaining biological activity data, methods of synthesis, modes of administration and pharmaceutical formulations for these agonists and related compounds are disclosed in U.S. Pat. No. 6,627,645, US 2005/0113357, and WO 01/83472, all of which are hereby incorporated by reference as if fully set forth.

In yet further embodiments, the agent is a muscarinic agonist or a compound that is functionally or structurally related to such an agonist. Structures, biological activity data, methods for obtaining biological activity data, methods of synthesis, modes of administration and pharmaceutical formulations for these agonists and related compounds are disclosed in U.S. Pat. No. 6,528,529, US 2003/0144285, WO 01/05763, and WO 99/50247, all of which are hereby incorporated by reference as if fully set forth.

Structures, biological activity data, methods for obtaining biological activity data, methods of synthesis, modes of administration and pharmaceutical formulations for other muscarinic agents are described in U.S. Pat. Nos., 5,675,007, 5,902,814, 6,051,581, 5,384,408, 5,468,875, 5,773,458, 5,512,574, 5,407,938, 5,668,174, 4,870,081, 4,968,691, 4,971,975, 5,110,828, 5,166,357, 5,124,460, 5,132,316, 5,262,427, 5,324,724, 5,534,520, 5,541,194, 5,599,937, 5,852,029, 5,981,545, 5,527,813, 5,571,826, 5,574,043, 5,578,602, 5,605,908, 5,641,791, 5,646,289, 5,665,745, 5,672,709, 6,911,477, 5,834,458, 5,756,501, 5,510,478, 5,093,333, 5,571,819, 4,992,457, and 5,362,739, Intl. Publication Nos. EP 384288, WO 9917771, JP 61280497, WO 9700894, WO 9847900, WO 9314089, EP 805153, WO 9422861, WO 9603377, EP 429344, EP 647642, WO 9626196, WO 9800412, WO 9531457, JP 61280497, JP 6298732, JP 6305967, WO 9640687, EP 311313, EP 370415, EP 709381, EP 723781, EP 727208, EP 727209, WO 9740044 and EP 384285, Ward et al., J. Med. Chem., 38, 3469 (1995), Wermuth et al., Farmaco., 48(2):253-74 (1993), Biorg. Med. Chem. Let., 2; 833-838 (1992), and Nordvall et al., J. Med. Chem., 35, 1541 (1992), all of which are herein incorporated by reference in their entirety.

As provided herein, an AChE inhibitor may be an organophosphate such as metrifonate or echothiophate as non-limiting examples.

Metrifonate (also known as metriphonate or trichlorfon) or its active metabolite, 2,2-dimethyldichlorovinyl phosphate (or dichlorvos or DDVP). Metrifonate is represented by the following formula:

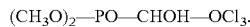

$(CH_3O)_2-PO-CHOH-OCl_3$.

Metrifonate has been used to treat Alzheimer's Disease (see the studies of Cummings et al. "The efficacy of Metrifonate in improving the behavioral disturbance of Alzheimer's disease patients." Neurology 1998; 50:A251).

Echothiophate is also known as ecothiopate, echothiophate iodide, phospholine iodide, (2-Mercaptoethyl)trimethylammonium S-ester with O,O'-diethylphosphorothioate, BRN 1794025, ecothiopatum, or phospholine. Echothiophate is referenced by CAS Registry Number 6736-03-4.

In other embodiments, an AChE inhibitor is an aminoacridine such as tacrine as a non-limiting example. Tacrine is also known as tetrahydroaminoacridine or THA. Tacrine is referenced by CAS Registry Number 321-64-2.

In additional embodiments, an AChE inhibitor is a carbamate such as physostigmine, neostigmine, or rivastigmine as non-limiting examples.

Physostigmine, also known as 1,2,3,3a,8,8a-hexahydro-1,3a,8-trimethyl-, methylcarbamate (ester) or (3aS,8aR)-pyrrolo(2,3-b)indol-5-ol, is referenced by CAS number 57-47-6. It is a tertiary amine capable of crossing the blood-brain barrier.

Neostigmine, or m-hydroxyphenyl)trimethyl-dimethylcarbamate(ester) ammonium, is referenced by CAS number 59-99-4.

Rivastigmine is also known as rivastigmine tartrate or (S)-N-Ethyl-N-methyl-3-[1-(dimethylamino)ethyl]-phenyl carbamate hydrogen-(2R,3R)-tartrate or SDZ ENA 713 or ENA 713. The reference for rivastigmine is CAS Registry Number 123441-03-2.

In further embodiments, an AChE inhibitor is a carbamate phenanthrine derivative such as galantamine or its hydrogen bromide form as non-limiting examples.

Galantamine is also known as (4aS,6R,8aS)-4a,5,9,10,11,12-hexahydro-3-methoxy-11-methyl-6H-benzofuro(3a,3,2-ef)(2)benzazepin-6-ol and is often used in its hydrogen bromide form. Galantamine is referenced by CAS number 357-70-0.

An AChE inhibitor may also be a piperidine derivative, such as donepezil as a non-limiting example. Donepezil is also known as 2,3-dihydro-5,6-dimethoxy-2-((1-(phenylmethyl)-4-piperidinyl)methyl)-1H-inden-1-one, and is referenced by CAS number 120014-06-4.

Itopride may also be an AChE inhibitor for use in embodiments disclosed herein. Itopride HCl is referenced by CAS Registry Number 122898-67-3. In one embodiment, a total daily dose range for itopride HCl is from about 25 mg to about 1000 mg, or between about 100 mg to about 300 mg. In some embodiments, the AChE inhibitor, or neurogenic agent, is the N-oxide derivative of itopride, which is the primary human metabolite of itopride HCl.

Another AChE inhibitor for use in the disclosed embodiments is (−)-huperzine A, which is also referred to as HupA and 1-amino-13-ethylidene-11-methyl-6-aza-tricyclo [7.3.1.02,7]trideca-2(7),3,10-trien-5-one. It is referenced by CAS number 102518-79-6.

A further embodiment of an AChE inhibitor is phenserine, the structure and synthesis of which is described in U.S. Pat. No. 6,495,700, which is hereby incorporated by reference as if fully set forth.

Methods for assessing the nature and/or degree of neurogenesis in vivo and in vitro, for detecting changes in the nature and/or degree of neurogenesis, for identifying neurogenesis modulating agents, for isolating and culturing neural stem cells, and for preparing neural stem cells for transplantation or other purposes are disclosed, for example, in U.S. Provisional Application No. 60/697,905, and U.S. Publication Nos. 2005/0009742 and 2005/0009847, 20050032702, 2005/0031538, 2005/0004046, 2004/0254152, 2004/0229291, and 2004/0185429, all of which are herein incorporated by reference in their entirety.

Neurogenesis includes the differentiation of neural cells along different potential lineages. In some embodiments, the differentiation of neural stem or progenitor cells is along a neuronal and/or glial cell lineage, optionally to the exclusion of differentiation along an astrocyte lineage.

A muscarinic agent, such as an AChE inhibitor, as described herein includes pharmaceutically acceptable salts, derivatives, prodrugs, and metabolites of the inhibitor. Methods for preparing and administering salts, derivatives, prodrugs, and metabolites of various inhibitors are well known in the art.

Compounds described herein that contain a chiral center include all possible stereoisomers of the compound, including compositions comprising the racemic mixture of the two enantiomers, as well as compositions comprising each enantiomer individually, substantially free of the other enantiomer. Thus, for example, contemplated herein is a composition comprising the S enantiomer of a compound substantially free of the R enantiomer, or the R enantiomer substantially free of the S enantiomer. If the named compound comprises more than one chiral center, the scope of the present disclosure also includes compositions comprising mixtures of varying proportions between the diastereomers, as well as compositions comprising one or more diastereomers substantially free of one or more of the other diastereomers. By "substantially free" it is meant that the composition comprises less than 25%, 15%, 10%, 8%, 5%, 3%, or less than 1% of the minor enantiomer or diastereomer(s). Methods for synthesizing, isolating, preparing, and administering various stereoisomers are known in the art.

Methods described herein can be used to treat any disease or condition for which it is beneficial to promote or otherwise stimulate or increase neurogenesis. One focus of the methods described herein is to achieve a therapeutic result by increasing neurogenesis. Thus, certain methods described herein can be used to treat any disease or condition susceptible to treatment by increasing neurogenesis.

In some embodiments, the disease or condition being treated is associated with pain and/or addiction, but in contrast to known methods, the disclosed treatments are substantially mediated by increasing neurogenesis. For example, in some embodiments, methods described herein involve increasing neurogenesis ex vivo, such that a composition containing neural stem cells, neural progenitor cells, and/or differentiated neural cells can subsequently be administered to an individual to treat a disease or condition. In some embodiments, methods described herein allow treatment of diseases characterized by pain, addiction, and/or depression to be treated by directly replenishing, replacing, and/or supplementing neurons and/or glial cells. In further embodiments, methods described herein enhance the growth and/or survival of existing neural cells, and/or slow or reverse the loss of such cells in a neurodegenerative condition.

Examples of diseases and conditions treatable by the methods described herein include, but are not limited to, neurodegenerative disorders and neural disease, such as dementias (e.g., senile dementia, memory disturbances/memory loss, dementias caused by neurodegenerative disorders (e.g., Alzheimer's, Parkinson's disease, Parkinson's disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

The disclosed embodiments also provide for the treatment of a nervous system disorder related to neural damage, cellular degeneration, a psychiatric condition, cellular (neurological) trauma and/or injury (e.g., subdural hematoma or traumatic brain injury), toxic chemicals (e.g., heavy metals, alcohol, some medications), CNS hypoxia, or other neurologically related conditions. In practice, the disclosed compositions and methods may be applied to a subject or patient afflicted with, or diagnosed with, one or more central or peripheral nervous system disorders in any combination. Diagnosis may be performed by a skilled person in the applicable fields using known and routine methodologies which identify and/or distinguish these nervous system disorders from other conditions.

Non-limiting examples of nervous system disorders related to cellular degeneration include neurodegenerative disorders, neural stem cell disorders, neural progenitor cell disorders, degenerative diseases of the retina, and ischemic disorders. In some embodiments, an ischemic disorder comprises an insufficiency, or lack, of oxygen or angiogenesis, and non-limiting example include spinal ischemia, ischemic stroke, cerebral infarction, multi-infarct dementia. While these conditions may be present individually in a subject or patient, the disclosed methods also provide for the treatment of a subject or patient afflicted with, or diagnosed with, more than one of these conditions in any combination.

Non-limiting embodiments of nervous system disorders related to a psychiatric condition include neuropsychiatric disorders and affective disorders. As used herein, an affective disorder refers to a disorder of mood such as, but not limited to, depression, post-traumatic stress disorder (PTSD), hypomania, panic attacks, excessive elation, bipolar depression, bipolar disorder (manic-depression), and seasonal mood (or affective) disorder. Other non-limiting embodiments include schizophrenia and other psychoses, lissencephaly syndrome, anxiety syndromes, anxiety disorders, phobias, stress and related syndromes (e.g., panic disorder, phobias, adjustment disorders, migraines), cognitive function disorders, aggression, drug and alcohol abuse, drug addiction, and drug-induced neurological damage, obsessive compulsive behavior syndromes, borderline personality disorder, non-senile dementia, post-pain depression, post-partum depression, and cerebral palsy.

Examples of nervous system disorders related to cellular or tissue trauma and/or injury include, but are not limited to, neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

Non-limiting examples of nervous system disorders related to other neurologically related conditions include learning disorders, memory disorders, age-associated memory impairment (AAMI) or age-related memory loss, autism, learning or attention deficit disorders (ADD or attention deficit hyperactivity disorder, ADHD), narcolepsy, sleep disorders and sleep deprivation (e.g., insomnia, chronic fatigue syndrome), cognitive disorders, epilepsy, injury related to epilepsy, and temporal lobe epilepsy.

Other non-limiting examples of diseases and conditions treatable by the methods described herein include, but are not limited to, hormonal changes (e.g., depression and other mood disorders associated with puberty, pregnancy, or aging (e.g., menopause)); and lack of exercise (e.g., depression or other mental disorders in elderly, paralyzed, or physically handicapped patients); infections (e.g., HIV); genetic abnormalities (down syndrome); metabolic abnormalities (e.g., vitamin B12 or folate deficiency); hydrocephalus; memory loss separate from dementia, including mild cognitive impairment (MCI), age-related cognitive decline, and memory loss resulting from the use of general anesthetics, chemotherapy, radiation treatment, post-surgical trauma, or therapeutic intervention; and diseases of the of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

Additionally, the disclosed methods provide for the application of a muscarinic agent, such as an AChE inhibitor, optionally in combination with another muscarinic agent and/or another neurogenic agent, to treat a subject or patient for a condition due to the anti-neurogenic effects of an opiate or opioid based analgesic. In some embodiments, the administration of an opiate or opioid based analgesic, such as an opiate like morphine or other opioid receptor agonist, to a subject or patient results in a decrease in, or inhibition of, neurogenesis. The administration of a muscarinic agent, such as an AChE inhibitor, optionally in combination with another muscarinic agent and/or another neurogenic agent, with an opiate or opioid based analgesic would reduce the anti-neurogenic effect. One non-limiting example is administration of a muscarinic agent, such as an AChE inhibitor, optionally in combination with another muscarinic agent and/or another neurogenic agent, with an opioid receptor agonist after surgery (such as for the treating post-operative pain).

So the disclosed embodiments include a method of treating post operative pain in a subject or patient by combining administration of an opiate or opioid based analgesic with a muscarinic agent, such as an AChE inhibitor, optionally in combination with another muscarinic agent and/or another neurogenic agent. The analgesic may have been administered before, simultaneously with, or after a muscarinic agent, such as an AChE inhibitor, alone or in combination with another neurogenic agent. In some cases, the analgesic or opioid receptor agonist is morphine or another opiate.

Other disclosed embodiments include a method to treat or prevent decreases in, or inhibition of, neurogenesis in other cases involving use of an opioid receptor agonist. The methods comprise the administration of a muscarinic agent, such as an AChE inhibitor, optionally in combination with another muscarinic agent and/or another neurogenic agent, as described herein. Non-limiting examples include cases involving an opioid receptor agonist, which decreases or inhibits neurogenesis, and drug addiction, drug rehabilitation, and/or prevention of relapse into addiction. In some embodiments, the opioid receptor agonist is morphine, opium or another opiate.

Compounds and compositions disclosed herein can also be used to treat diseases of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

Other conditions that can be beneficially treated by increasing neurogenesis are known in the art (see e.g., U.S. Publication Nos. 20020106731, 2005/0009742 and 2005/0009847, 20050032702, 2005/0031538, 2005/0004046, 2004/0254152, 2004/0229291, and 2004/0185429, herein incorporated by reference in their entirety).

In some embodiments, a muscarinic agent, such as an AChE inhibitor, optionally in combination with another muscarinic agent and/or another neurogenic agent, used in the methods described herein, is in the form of compositions that include at least one pharmaceutically acceptable excipient. As used herein, the term "pharmaceutically acceptable excipient" includes any excipient known in the field as suitable for pharmaceutical application. Suitable pharmaceutical excipients and formulations are known in the art and are described, for example, in Remington's Pharmaceutical Sciences (19th ed.) (Genarro, ed. (1995) Mack Publishing Co., Easton, Pa.). Pharmaceutical carriers may be chosen by a skilled person based upon the intended mode of administration of a muscarinic agent. The pharmaceutically acceptable carrier may include, for example, disintegrants, binders, lubricants, glidants, emollients, humectants, thickeners, silicones, flavoring agents, and water.

A muscarinic agent, such as an AChE inhibitor, may be incorporated with excipients and administered in the form of ingestible tablets, buccal tablets, troches, capsules, elixirs, suspensions, syrups, wafers, or any other form known in the pharmaceutical arts. The pharmaceutical compositions may also be formulated in a sustained release form. Sustained release compositions, enteric coatings, and the like are known in the art. Alternatively, the compositions may be a quick release formulation.

In some embodiments, methods of treatment disclosed herein comprise the step of administering to a mammal a muscarinic agent, such as an AChE inhibitor, optionally in combination with another muscarinic agent and/or another neurogenic agent, for a time and at a concentration sufficient to treat the condition targeted for treatment. The disclosed methods can be applied to individuals having, or who are likely to develop, disorders relating to neural degeneration, neural damage and/or neural demyelination. In some embodiments, a method comprises selecting a population or sub-population of patients, or selecting an individual patient, that is more amenable to treatment and/or less susceptible to side effects than other patients having the same disease or condition. For example, in some embodiments, a sub-population of patients is identified as being more amenable to neurogenesis with a muscarinic agent, such as an AChE inhibitor, optionally in combination with another muscarinic agent and/or another neurogenic agent, by taking a cell or tissue sample from prospective patients, isolating and culturing neural cells from the sample, and determining the effect of a muscarinic agent, such as an AChE inhibitor, optionally in combination with another muscarinic agent and/or another neurogenic agent, on the degree or nature of neurogenesis, thereby allowing selection of patients for which a muscarinic agent, or combination of neurogenic agents comprising it, has a substantial effect on neurogenesis. Advantageously, the selection step(s) results in more effective treatment for the disease or condition that known methods using the same or similar compounds.

In other embodiments, the method of treatment comprises identifying, generating, and/or propagating neural cells ex vivo in contact with a muscarinic agent, such as an AChE inhibitor, optionally in combination with another muscarinic agent and/or another neurogenic agent, and transplanting the cells into a subject. In another embodiment, the method of treatment comprises the steps of contacting a neural stem cell of progenitor cell with a muscarinic agent, such as an AChE inhibitor, optionally in combination with another muscarinic agent and/or another neurogenic agent, to stimulate neurogenesis, and transplanting the cells into a patient in need of treatment. Also disclosed are methods for preparing a population of neural stem cells suitable for transplantation, comprising culturing a population of neural stem cells (NSCs) in vitro, and contacting the cultured neural stem cells with a muscarinic agent, such as an AChE inhibitor, optionally in combination with another muscarinic agent and/or another neurogenic agent, described herein. The disclosure further includes methods of treating the diseases, disorders, and conditions described herein by transplanting such cells into a subject or patient.

Methods described herein may comprise administering to the subject an effective amount of a muscarinic agent, such as an AChE inhibitor, optionally in combination with another muscarinic agent and/or another neurogenic agent, or pharmaceutical composition comprising the muscarinic agent. In general, an effective amount of compound(s) in the disclosed methods is an amount sufficient, when used as described herein, to stimulate or increase neurogenesis in the subject targeted for treatment when compared to the absence of the compound. An effective amount of a composition may vary based on a variety of factors, including but not limited to, the activity of the active compound(s), the physiological characteristics of the subject, the nature of the condition to be treated, and the route and/or method of administration. The disclosed methods typically involve the administration of a muscarinic agent, such as an inhibitor of AChE activity, alone or in combination with another neurogenic agent, in a dosage range of 0.001 ng/kg/day to 500 ng/kg/day or in a dosage range of 0.05 to 200 ng/kg/day. Advantageously, methods described herein allow treatment of indications with reductions in side effects, dosage levels, dosage frequency, treatment duration, tolerability, and/or other factors.

In some methods described herein, the application of a muscarinic agent with selective activity towards one or more muscarinic receptors may allow effective treatment with substantially fewer and/or less severe side effects compared to existing treatments. For example, muscarinic agents with selectivity for m1 receptors, which are primarily located in the CNS, can reduce side effects associated with activity at muscarinic receptors outside the intended target tissue/organ. Similarly, the application of an AChE inhibitor in combination with another muscarinic agent and/or another neurogenic agent may also allow effective treatment with substantially fewer and/or less severe side effects compared to other treatments. For example, each neurogenic agent in a combination of agents may be present in an amount that results in fewer and/or less severe side effects than that which occurs with a larger amount. Thus the combined effect of the neurogenic agents will provide a desired neurogenic activity while exhibiting fewer and/or less severe side effects overall.

As non-limiting examples, fluoxetine has been reported to result in problems such as sexual dysfunction and (rarely) agitation and increased suicidal thoughts after acute administration at high doses. Sabcomeline has been reported to have dose limiting toxicities in the clinic from excessive sweating, nausea, vomiting and diarrhea. As shown in FIG. 13, however, the combination of these two compounds at doses that are individually sub-therapeutic in reference to clinical reports (and in promoting neurogenesis and anti-depressant activity in vivo by assays described herein) results in efficacy in a model of depression and is observed to promote neurogenesis. The sub-therapeutic doses are believed to be below those reported as associated with severe or significant side effects.

Established methods of treating various conditions of the CNS and PNS with compounds having activity against muscarinic receptors have been known to cause side effects including, but not limited to, sweating, diarrhea, flushing, hypotension, bradycardia, bronchoconstriction, urinary bladder contraction, nausea, vomiting, parkinsonism, and increased mortality risk. In some embodiments, methods described herein allow treatment of certain conditions for which treatment with the same or similar compounds is ineffective using known methods due, for example, to dose-limiting side effects. As non-limiting examples, methods comprising the use of reduced amounts of a muscarinic agent, such as an AChE inhibitor, in combination with another muscarinic agent and/or another neurogenic agent, as described herein treats certain conditions with minimization of these side effects.

Depending on the desired clinical result, the disclosed neurogenic agents or pharmaceutical compositions are administered by any means suitable for achieving a desired effect. Various delivery methods are known in the art and can be used to deliver an agent to a subject or to NSCs or progenitor cells within a tissue of interest. The delivery method will depend on factors such as the tissue of interest, the nature of the compound (e.g., its stability and ability to cross the blood-brain barrier), and the duration of the experiment, among other factors. For example, an osmotic minipump can be implanted into a neurogenic region, such as the lateral ventricle. Alternatively, compounds can be administered by direct injection into the cerebrospinal fluid of the brain or spinal column, or into the eye. Compounds can also be administered into the periphery (such as by intravenous or subcutaneous injection, or oral delivery), and subsequently cross the blood-brain barrier.

In various embodiments, the disclosed agents or pharmaceutical compositions are administered in a manner that allows them to contact the subventricular zone (SVZ) of the lateral ventricles and/or the dentate gyrus of the hippocampus. Examples of routes of administration include parenteral, e.g., intravenous, intradermal, subcutaneous, oral (e.g., inhalation), transdermal (topical), transmucosal, and rectal administration. Intranasal administration generally includes, but is not limited to, inhalation of aerosol suspensions for delivery of compositions to the nasal mucosa, trachea and bronchioli.

In some embodiments, the compound combinations are administered so as to either pass through or by-pass the blood-brain barrier. Methods for allowing factors to pass through the blood-brain barrier are known in the art, and include minimizing the size of the factor, providing hydrophobic factors which facilitate passage, and conjugating a muscarinic agent, such as an inhibitor of AChE activity, to a carrier molecule that has substantial permeability across the blood brain barrier. In some instances, the combination of compounds can be administered by a surgical procedure implanting a catheter coupled to a pump device. The pump device can also be implanted or be extracorporally positioned. Administration of the muscarinic agent can be in intermittent pulses or as a continuous infusion. Devices for injection to discrete areas of the brain are known in the art. In certain embodiments, the muscarinic agent is administered locally to the ventricle of the brain, substantia nigra, striatum, locus ceruleous, nucleus basalis Meynert, pedunculopontine nucleus, cerebral cortex, and/or spinal cord by, e.g., injection. Methods, compositions, and devices for delivering therapeutics, including therapeutics for the treatment of diseases and conditions of the CNS and PNS, are known in the art.

In some embodiments, the delivery or targeting of a muscarinic agent, such as an inhibitor of AChE activity, to a neurogenic region, such as the dentate gyrus or the subventricular zone, enhances efficacy and reduces side effects compared to known methods involving administration with the same or similar compounds.

In embodiments to treat subjects and patients, the methods include identifying a patient suffering from one or more disease, disorders, or conditions, or a symptom thereof, and administering to the subject or patient at least one muscarinic agent, such as an inhibitor of AChE activity, as described herein. The identification of a subject or patient as having one or more disease, disorder or condition, or a symptom thereof, may be made by a skilled practitioner using any appropriate means known in the field.

In further embodiments, the methods may be used to treat a cell, tissue, or subject which is exhibiting decreased neurogenesis or increased neurodegeneration. In some cases, the cell, tissue, or subject is, or has been, subjected to, or contacted with, an agent that decreases or inhibits neurogenesis. One non-limiting example is a human subject that has been administered morphine or other agent which decreases or inhibits neurogenesis. Non-limiting examples of other agents include opiates and opioid receptor agonists, such as mu receptor subtype agonists, that inhibit or decrease neurogenesis.

Thus in additional embodiments, the methods may be used to treat subjects having, or diagnosed with, depression or other withdrawal symptoms from morphine or other agents which decrease or inhibit neurogenesis. This is distinct from the treatment of subjects having, or diagnosed with, depression independent of an opiate, such as that of a psychiatric nature, as disclosed herein. In further embodiments, the methods may be used to treat a subject with one or more chemical addiction or dependency, such as with morphine or other opiates, where the addiction or dependency is ameliorated or alleviated by an increase in neurogenesis.

In some embodiments, such as those for treating depression and other neurological diseases and conditions, the methods may optionally further comprise use of one or more agents reported as anti-depressant agents. Thus a method may comprise treatment with a muscarinic agent, such as an inhibitor of AChE activity, and one or more reported antidepressant agents as known to the skilled person. Non-limiting examples of such agents include an SSRI (selective serotonine reuptake inhibitor), such as fluoxetine (Prozac®), citalopram (Celexa), escitalopram (Lexapro), fluvoxamine or fluvoxamine maleate (CAS RN: 61718-82-9) and Luvox®, paroxetine (Paxil®), or sertraline (Zoloft®; the compound nefazodone (Serozone®); a selective norepinephrine reuptake inhibitor (SNRI) such as reboxetine (Edronax®) or atomoxetine (Strattera®); a selective serotonin & norepinephrine reuptake inhibitor (SSNRI) such as venlafaxine (Effexor), and its reported metabolite desvenlafaxine, or duloxetine (Cymbalta); a serotonin, noradrenaline, and dopamine "triple uptake inhibitor", such as DOV 102,677 (see Popik et al. "Pharmacological Profile of the "Triple" Monoamine Neurotransmitter Uptake Inhibitor, DOV 102,677." Cell Mol Neurobiol. 2006 Apr. 25; Epub ahead of print), DOV 216,303 (see Beer et al. "DOV 216,303, a "triple" reuptake inhibitor: safety, tolerability, and pharmacokinetic profile." J Clin Pharmacol. 2004 44(12):1360-7), DOV 21,947 ((+)-1-(3,4-dichlorophenyl)-3-azabicyclo-(3.1.0)hexane hydrochloride), see Skolnick et al. "Antidepressant-like actions of DOV 21,947: a "triple" reuptake inhibitor." Eur J Pharmacol. 2003 461(2-3):99-104), NS-2330 or tesofensine (CAS RN 402856-42-2), or NS 2359 (CAS RN 843660-54-8);

and agents like dehydroepiandrosterone (DHEA), and DHEA sulfate (DHEAS), CP-122,721 (CAS RN 145742-28-5).

Additional non-limiting examples of such agents include a tricyclic compound such as amitriptyline, desipramine, doxepin, imipramine, or nortriptyline; a psychostimulant such as dextroamphetamine and methylphenidate; an MAO inhibitor such as selegiline (Emsam®); an ampakine such as CX516 (or Ampalex, CAS RN: 154235-83-3), CX546 (or 1-(1,4-benzodioxan-6-ylcarbonyl)piperidine), and CX614 (CAS RN 191744-13-5) from Cortex Pharmaceuticals; a V1b antagonist such as SSR149415 ((2S,4R)-1-[5-Chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide),

[1-(beta-mercapto-beta,beta-cyclopentamethylenepropionic acid), 2-O-ethyltyrosine, 4-valine] arginine vasopressin (d(CH2)5[Tyr(Et2)]VAVP (WK 1-1), 9-desglycine[1-(beta-mercapto-beta,beta-cyclopentamethylenepropionic acid), 2-O-ethyltyrosine, 4-valine] arginine vasopressin desGly9d(CH2)5 [Tyr(Et2)]-VAVP (WK 3-6), or 9-desglycine[1-(beta-mercapto-beta,beta-cyclopentamethylenepropionic acid),2-D-(O-ethyl)tyrosine, 4-valine] arginine vasopressin des Gly9d(CH2)5[D-Tyr(Et2)]VAVP (AO 3-21); a corticotropin-releasing factor (CRF) R antagonist such as CP-154,526 (structure disclosed in Schulz et al. "CP-154,526: a potent and selective nonpeptide antagonist of corticotropin releasing factor receptors." Proc Natl Acad Sci USA. 1996 93(19):10477-82), NBI 30775 (also known as R121919 or 2,5-dimethyl-3-(6-dimethyl-4-methylpyridin-3-yl)-7-dipropylaminopyrazolo[1,5-a]pyrimidine), astressin (CAS RN 170809-51-5), or a photoactivatable analog thereof as described in Bonk et al. "Novel high-affinity photoactivatable antagonists of corticotropin-releasing factor (CRF)" Eur. J. Biochem. 267:3017-3024 (2000), or AAG561 (from Novartis); a melanin concentrating hormone (MCH) antagonist such as 3,5-dimethoxy-N-(1-(naphthalen-2-ylmethyl)piperidin-4-yl)benzamide or (R)-3,5-dimethoxy-N-(1-(naphthalen-2-ylmethyl)-pyrrolidin-3-yl)benzamide (see Kim et al. "Identification of substituted 4-aminopiperidines and 3-aminopyrrolidines as potent MCH-R1 antagonists for the treatment of obesity." Bioorg Med Chem Lett. 2006 Jul. 29; [Epub ahead of print] for both), or any MCH antagonist disclosed in U.S. Pat. No. 7,045,636 or published U.S. Patent Application US2005/0171098.

Further non-limiting examples of such agents include agomelatine (CAS RN 138112-76-2), mirtazapine (CAS RN 61337-67-5, also known as Remeron, or CAS RN 85650-52-8), pindolol (CAS RN 13523-86-9), antalarmin (CAS RN 157284-96-3), mifepristone (CAS RN 84371-65-3), nemifitide (CAS RN 173240-15-8) or nemifitide ditriflutate (CAS RN 204992-09-6), YKP-10A or R228060 (CAS RN 561069-23-6), trazodone (CAS RN 19794-93-5), bupropion (CAS RN 34841-39-9 or 34911-55-2) or bupropion hydrochloride (or Wellbutrin, CAS RN 31677-93-7) and its reported metabolite radafaxine (CAS RN 192374-14-4), NS2359 (CAS RN 843660-54-8), Org 34517 (CAS RN 189035-07-2), Org 34850 (CAS RN 162607-84-3), vilazodone (CAS RN 163521-12-8), CP-122,721 (CAS RN 145742-28-5), gepirone (CAS RN 83928-76-1), SR58611 (see Mizuno et al. "The stimulation of beta(3)-adrenoceptor causes phosphorylation of extracellular signal-regulated kinases 1 and 2 through a G(s)- but not G(i)-dependent pathway in 3T3-L1 adipocytes." Eur J Pharmacol. 2000 404(1-2):63-8), saredutant or SR 48968 (CAS RN 142001-63-6), PRX-00023 (N-{3-[4-(4-cyclohexylmethanesulfonylaminobutyl)piperazin-1-yl]phenyl}acetamide, see Becker et al. "An integrated in silico 3D model-driven discovery of a novel, potent, and selective amidosulfonamide 5-HT1A agonist (PRX-00023) for the treatment of anxiety and depression." J Med Chem. 2006 49(11):3116-35), Vestipitant (or GW597599, CAS RN 334476-46-9), OPC-14523 or VPI-013 (see Bermack et al. "Effects of the potential antidepressant OPC-14523 [1-[3-[4-(3-chlorophenyl)-1-piperazinyl]propyl]-5-methoxy-3,4-dihydro-2-quinolinone monomethanesulfonate] a combined sigma and 5-HT1A ligand: modulation of neuronal activity in the dorsal raphe nucleus." J Pharmacol Exp Ther. 2004 310 (2):578-83), Casopitant or GW679769 (CAS RN 852393-14-7), Elzasonan or CP-448,187 (CAS RN 361343-19-3), GW823296 (see published U.S. Patent Application US2005/0119248), Delucemine or NPS 1506 (CAS RN 186495-49-8), or Ocinaplon (CAS RN 96604-21-6).

Yet additional non-limiting examples of such agents include CX717 from Cortex Pharmaceuticals, TGBA01AD (a serotonin reuptake inhibitor, 5-HT2 agonist, 5-HT1A agonist, and 5-HT1D agonist) from Fabre-Kramer Pharmaceuticals, Inc., ORG 4420 (an NaSSA (noradrenergic/specific serotonergic antidepressant) from Organon, CP-316,311 (a CRF1 antagonist) from Pfizer, BMS-562086 (a CRF1 antagonist) from Bristol-Myers Squibb, GW876008 (a CRF1 antagonist) from Neurocrine/GlaxoSmithKline, ONO-2333Ms (a CRF1 antagonist) from Ono Pharmaceutical Co., Ltd., JNJ-19567470 or TS-041 (a CRF1 antagonist) from Janssen (Johnson & Johnson) and Taisho, SSR 125543 or SSR 126374 (a CRF1 antagonist) from Sanofi-Aventis, Lu AA21004 and Lu AA24530 (both from H. Lundbeck A/S), SEP-225289 from Sepracor Inc., ND7001 (a PDE2 inhibitor) from Neuro3d, SSR 411298 or SSR 101010 (a fatty acid amide hydrolase, or FAAH, inhibitor) from Sanofi-Aventis, 163090 (a mixed serotonin receptor inhibitor) from GlaxoSmithKline, SSR 241586 (an NK2 and NK3 receptor antagonist) from Sanofi-Aventis, SAR 102279 (an NK2 receptor antagonist) from Sanofi-Aventis, YKP581 from SK Pharmaceuticals (Johnson & Johnson), R1576 (a GPCR modulator) from Roche, or ND1251 (a PDE4 inhibitor) from Neuro3d.

Specific embodiments of the disclosure include combinations of each one of the above reported anti-depressants with sabcomeline for use in the disclosed methods. The efficacy of a combination of a muscarinic agent, such as an inhibitor of AChE activity, and an antidepressant is shown in FIGS. 13A and 13B.

In other disclosed embodiments, a reported anti-psychotic agent may be used in combination with a muscarinic agent, such as an inhibitor of AChE activity. Non-limiting examples of a reported anti-psychotic agent as a member of a combination include olanzapine, quetiapine (Seroquel), clozapine (CAS RN 5786-21-0) or its metabolite ACP-104 (N-desmethylclozapine or norclozapine, CAS RN 6104-71-8), reserpine, aripiprazole, risperidone, ziprasidone, paliperidone (CAS RN 144598-75-4), mifepristone (CAS RN 84371-65-3), bifeprunox or DU-127090 (CAS RN 350992-10-8), asenapine or ORG 5222 (CAS RN 65576-45-6), iloperidone (CAS RN 133454-47-4), ocaperidone (CAS RN 129029-23-8), SLV 308 (CAS RN 269718-83-4), licarbazepine or GP 47779 (CAS RN 29331-92-8), Org 34517 (CAS RN 189035-07-2), ORG 34850 (CAS RN 162607-84-3), Org 24448 (CAS RN 211735-76-1), lurasidone (CAS RN 367514-87-2), blonanserin or lonasen (CAS RN 132810-10-7), Talnetant or SB-223412 (CAS RN 174636-32-9), secretin (CAS RN 1393-25-5) or human secretin (CAS RN 108153-74-8) which are endogenous pancreatic hormones, ABT 089 (CAS RN 161417-03-4), SSR 504734 (see compound 13 in Hashimoto "Glycine Transporter Inhibitors as Therapeutic Agents for Schizophrenia." *Recent Patents on CNS Drug Discovery*, 2006 1:43-53), MEM 3454 (see Mazurov et al. "Selective alpha7 nicotinic acetylcholine receptor ligands." *Curr Med Chem.* 2006 13(13):1567-84), a phosphodiesterase 10A (PDE10A) inhibitor such as papaverine (CAS RN 58-74-2) or papaverine hydrochloride (CAS RN 61-25-6), paliperidone (CAS RN 144598-75-4), trifluoperazine (CAS RN 117-89-5), or trifluoperazine hydrochloride (CAS RN 440-17-5).

Additional non-limiting examples of such agents include trifluoperazine, fluphenazine, chlorpromazine, perphenazine, thioridazine, haloperidol, loxapine, mesoridazine, molindone, pimoxide, or thiothixene, SSR 146977 (see Emonds-Alt et al. "Biochemical and pharmacological activities of SSR 146977, a new potent nonpeptide tachykinin NK3 receptor antagonist." *Can J Physiol Pharmacol.* 2002 80(5):482-8), SSR181507 ((3-exo)-8-benzoyl-N-[[(2 s)7-chloro-2,3-dihydro-1,4-benzodioxin-1-yl]-methyl]-8-azabicyclo[3.2.1]octane-3-methanamine monohydrochloride), or SLV313 (1-(2,3-dihydro-benzo[1,4]dioxin-5-yl)-4-[5-(4-fluorophenyl)-pyridin-3-ylmethyl]-piperazine).

Further non-limiting examples of such agents include Lu-35-138 (a D4/5-HT antagonist) from Lundbeck, AVE 1625 (a CB 1 antagonist) from Sanofi-Aventis, SLV 310,313 (a 5-HT2A antagonist) from Solvay, SSR 181507 (a D2/5-HT2 antagonist) from Sanofi-Aventis, GW07034 (a 5-HT6 antagonist) or GW773812 (a D2, 5-HT antagonist) from GlaxoSmithKline, YKP 1538 from SK Pharmaceuticals, SSR 125047 (a sigma receptor antagonist) from Sanofi-Aventis, MEM1003 (a L-type calcium channel modulator) from Memory Pharmaceuticals, JNJ-17305600 (a GLYT1 inhibitor) from Johnson & Johnson, XY 2401 (a glycine site specific NMDA modulator) from Xytis, PNU 170413 from Pfizer, RGH-188 (a D2, D3 antagonist) from Forrest, SSR 180711 (an alpha7 nicotinic acetylcholine receptor partial agonist) or SSR 103800 (a GLYT1 (Type 1 glycine transporter) inhibitor) or SSR 241586 (a NK3 antagonist) from Sanofi-Aventis.

In light of the positive recitation (above and below) of combinations with alternative agents to treat conditions disclosed herein, the disclosure includes embodiments with the explicit exclusion of one or more of the alternative agents. As would be recognized by the skilled person, a description of the whole of a plurality of alternative agents necessarily includes and describes subsets of the possible alternatives, or the part remaining with the exclusion of one or more of the alternatives.

The combination therapy may be of one of the above with a muscarinic agent, such as an inhibitor of AChE activity, as described herein to improve the condition of the subject or patient. Non-limiting examples of combination therapy include the use of lower dosages of the above which reduce side effects of the anti-depressant agent when used alone. For example, an anti-depressant agent like fluoxetine or paroxetine or sertraline may be administered at a reduced or limited dose, optionally also reduced in frequency of administration, in combination with a muscarinic agent, such as an inhibitor of AChE activity, alone or in combination with another muscarinic agent and/or another neurogenic agent. The reduced dose or frequency mediates a sufficient anti-depressant effect so that the side effects of the anti-depressant agent alone are reduced or eliminated. See FIG. 13.

In additional embodiments, such as, but not limited to, treating weight gain, metabolic syndrome, or obesity, and/or to induce weight loss, a muscarinic agent, such as an inhibitor of AChE activity, alone or in combination with another muscarinic agent and/or neurogenic agent, may be used in combination. Non-limiting examples of another agent include those reported for treating weight gain or metabolic syndrome and/or inducing weight loss such as various diet pills that are commercially or clinically available. In some embodiments, the reported agent for treating weight gain, metabolic syndrome, obesity, or for inducing weight loss is orlistat (CAS RN 96829-58-2), sibutramine (CAS RN 106650-56-0) or sibutramine hydrochloride (CAS RN 84485-00-7), phetermine (CAS RN 122-09-8) or phetermine hydrochloride (CAS RN 1197-21-3), diethylpropion or amfepramone (CAS RN 90-84-6) or diethylpropion hydrochloride, benzphetamine (CAS RN 156-08-1) or benzphetamine hydrochloride, phendimetrazine (CAS RN 634-03-7 or 21784-30-5) or phendimetrazine hydrochloride (CAS RN 17140-98-6) or phendimetrazine tartrate, rimonabant (CAS RN 168273-06-1), bupropion hydrochloride (CAS RN: 31677-93-7), topiramate (CAS RN 97240-79-4), zonisamide (CAS RN 68291-97-4), or APD-356 (CAS RN 846589-98-8).

In other non-limiting embodiments, the agent may be fenfluramine or Pondimin (CAS RN 458-24-2), dexfenfluramine or Redux (CAS RN 3239-44-9), or levofenfluramine (CAS RN 37577-24-5); or a combination thereof or a combination with phentermine. Non-limiting examples include a combination of fenfluramine and phentermine (or "fen-phen") and of dexfenfluramine and phentermine (or "dexfen-phen").

The combination therapy may be of one of the above with a muscarinic agent, such as an inhibitor of AChE activity, as described herein to improve the condition of the subject or patient. Non-limiting examples of combination therapy include the use of lower dosages of the above additional agents, or combinations thereof, which reduce side effects of the agent or combination when used alone. For example, a combination of fenfluramine and phentermine, or phentermine and dexfenfluramine, may be administered at a reduced or limited dose, optionally also reduced in frequency of administration, in combination with a muscarinic agent, such as an inhibitor of AChE activity, alone or in combination with another muscarinic agent and/or another neurogenic agent. The reduced dose or frequency may be that which reduces or eliminates the side effects of the combination.

As indicated herein, the disclosure includes combination therapy, where one or more muscarinic agent, such as inhibitors of AChE activity, and one or more other compounds are used together to produce neurogenesis. When administered as a combination, the therapeutic compounds can be formulated as separate compositions that are administered at the same time or sequentially at different times, or the therapeutic compounds can be given as a single composition. The methods of the disclosure are not limited in the sequence of administration.

Instead, the disclosure includes methods wherein treatment with a muscarinic agent, such as an inhibitor of AChE activity, and another muscarinic agent and/or neurogenic agent occurs over a period of more than about 48 hours, more than about 72 hours, more than about 96 hours, more than about 120 hours, more than about 144 hours, more than about 7 days, more than about 9 days, more than about 11 days, more than about 14 days, more than about 21 days, more than about 28 days, more than about 35 days, more than about 42 days, more than about 49 days, more than about 56 days, more than about 63 days, more than about 70 days, more than about 77 days, more than about 12 weeks, more than about 16 weeks, more than about 20 weeks, or more than about 24 weeks or more. In some embodiments, treatment by administering a muscarinic agent, such as an inhibitor of AChE activity, occurs at least about 12 hours, such as at least about 24, or at least about 36 hours, before administration of another neurogenic agent. Following administration of a muscarinic agent, such as an inhibitor of AChE activity, further administrations may be of only the other neurogenic agent in some embodiments of the disclosure. In other embodiments, further administrations may be of only the muscarinic agent.

In other embodiments, the neurogenic agent combined with a muscarinic agent, such as an inhibitor of AChE activity, may be a reported opioid or non-opioid (acts independently of an opioid receptor) agent. In some embodiments, the neurogenic agent is one reported as antagonizing one or more opioid receptors or as an inverse agonist of at least one opioid receptor. A opioid receptor antagonist or inverse agonist may be specific or selective (or alternatively non-specific or non-selective) for opioid receptor subtypes. So an antagonist may be non-specific or non-selective such that it antagonizes more than one of the three known opioid receptor subtypes, identified as $OP_1$, $OP_2$, and $OP_3$ (also know as delta, or δ, kappa, or κ, and mu, or μ, respectively). Thus an opioid that antagonizes any two, or all three, of these subtypes, or an inverse agonist that is specific or selective for any two or all three of these subtypes, may be used as the neurogenic agent in the practice. Alternatively, an antagonist or inverse agonist may be specific or selective for one of the three subtypes, such as the kappa subtype as a non-limiting example.

Non-limiting examples of reported opioid antagonists include naltrindol, naloxone, naloxene, naltrexone, JDTic (Registry Number 785835-79-2; also known as 3-isoquinolinecarboxamide, 1,2,3,4-tetrahydro-7-hydroxy-N-[(1S)-1-[[(3R,4R)-4-(3-hydroxyphenyl)-3,4-dimethyl-1-piperidinyl]methyl]-2-methylpropyl]-dihydrochloride, (3R)-(9CI)), norbinaltorphimine, and buprenorphine. In some embodiments, a reported selective kappa opioid receptor antagonist compound, as described in US 20020132828, U.S. Pat. No. 6,559,159, and/or WO 2002/053533, may be used. All three of these documents are herein incorporated by reference in their entireties as if fully set forth. Further non-limiting examples of such reported antagonists is a compound disclosed in U.S. Pat. No. 6,900,228 (herein incorporated by reference in its entirety), arodyn (Ac[Phe(1,2,3),Arg(4),d-Ala(8)]Dyn A-(1-11)NH(2), as described in Bennett, et al. (2002) *J. Med. Chem.* 45:5617-5619), and an active analog of arodyn as described in Bennett e al. (2005) J Pept Res. 65(3):322-32, alvimopan.

In some embodiments, the neurogenic agent used in the methods described herein has "selective" activity (such as in the case of an antagonist or inverse agonist) under certain conditions against one or more opioid receptor subtypes with respect to the degree and/or nature of activity against one or more other opioid receptor subtypes. For example, in some embodiments, the neurogenic agent has an antagonist effect against one or more subtypes, and a much weaker effect or substantially no effect against other subtypes. As another example, an additional neurogenic agent used in the methods described herein may act as an agonist at one or more opioid receptor subtypes and as antagonist at one or more other opioid receptor subtypes. In some embodiments, a neurogenic agent has activity against kappa opioid receptors, while having substantially lesser activity against one or both of the delta and mu receptor subtypes. In other embodiments, a neurogenic agent has activity against two opioid receptor subtypes, such as the kappa and delta subtypes. As non-limiting examples, the agents naloxone and naltrexone have nonselective antagonist activities against more than one opioid receptor subtypes. In certain embodiments, selective activity of one or more opioid antagonists results in enhanced efficacy, fewer side effects, lower effective dosages, less frequent dosing, or other desirable attributes.

An opioid receptor antagonist is an agent able to inhibit one or more characteristic responses of an opioid receptor or receptor subtype. As a non-limiting example, an antagonist may competitively or non-competitively bind to an opioid receptor, an agonist or partial agonist (or other ligand) of a receptor, and/or a downstream signaling molecule to inhibit a receptor's function.

An inverse agonist able to block or inhibit a constitutive activity of an opioid receptor may also be used. An inverse agonist may competitively or non-competitively bind to an opioid receptor and/or a downstream signaling molecule to inhibit a receptor's function. Non-limiting examples of inverse agonists for use in the disclosed methods include ICI-174864 (N,N-diallyl-Tyr-Aib-Aib-Phe-Leu), RTI-5989-1, RTI-5989-23, and RTI-5989-25 (see Zaki et al. *J Pharmacol. Exp. Therap.* 298(3): 1015-1020, 2001).

In further non-limiting embodiments, the neurogenic agent in combination with a muscarinic agent, such as an inhibitor of AChE activity, may be acetylcholine.

In yet further non-limiting embodiments, the neurogenic agent in combination with a muscarinic agent, such as an inhibitor of AChE activity, may be a reported modulator of an androgen receptor. Non-limiting examples include the androgen receptor agonists ehydroepiandrosterone (DHEA) and DHEA sulfate (DHEAS).

Alternatively, the neurogenic agent in combination with a muscarinic agent, such as an inhibitor of AChE activity, may be an enzymatic inhibitor, such as a reported inhibitor of HMG CoA reductase. Non-limiting examples of such inhibitors include atorvastatin (CAS RN 134523-00-5), cerivastatin (CAS RN 145599-86-6), crilvastatin (CAS RN 120551-59-9), fluvastatin (CAS RN 93957-54-1) and fluvastatin sodium (CAS RN 93957-55-2), simvastatin (CAS RN 79902-63-9), lovastatin (CAS RN 75330-75-5), pravastatin (CAS RN 81093-37-0) or pravastatin sodium, rosuvastatin (CAS RN 287714-41-4), and simvastatin (CAS RN 79902-63-9). Formulations containing one or more of such inhibitors may also be used in a combination. Non-limiting examples include formulations comprising lovastatin such as Advicor (an extended-release, niacin containing formulation) or Altocor (an extended release formulation); and formulations comprising simvastatin such as Vytorin (combination of simvastatin and ezetimibe).

In other non-limiting embodiments, the neurogenic agent in combination with a muscarinic agent, such as an inhibitor of AChE activity, may be a reported Rho kinase inhibitor. Non-limiting examples of such an inhibitor include fasudil (CAS RN 103745-39-7); fasudil hydrochloride (CAS RN 105628-07-7); the metabolite of fasudil, which is hydroxyfasudil (see Shimokawa et al. "Rho-kinase-mediated pathway induces enhanced myosin light chain phosphorylations in a swine model of coronary artery spasm." *Cardiovasc Res.* 1999 43:1029-1039), Y 27632 (CAS RN 138381-45-0); a fasudil analog thereof such as (S)-Hexahydro-1-(4-ethenylisoquinoline-5-sulfonyl)-2-methyl-1H-1,4-diazepine, (S)-hexahydro-4-glycyl-2-methyl-1 -(4-methylisoquinoline-5-sulfonyl)-1 H-1,4-diazepine, or (S)-(+)-2-methyl-1-[(4-methyl-5-isoquinoline)sulfonyl]-homopiperazine (also known as H-1152P; see Sasaki et al. "The novel and specific Rho-kinase inhibitor (S)-(+)-2-methyl-1-[(4-methyl-5-isoquinoline)sulfonyl]-homopiperazine as a probing molecule for Rho-kinase-involved pathway." *Pharmacol Ther.* 2002 93(2-3):225-32); or a substituted isoquinolinesulfonamide compound as disclosed in U.S. Pat. No. 6,906,061.

Furthermore, the neurogenic agent in combination with a muscarinic agent, such as an inhibitor of AChE activity, may be a reported GSK-3 inhibitor or modulator. In some non-limiting embodiments, the reported GSK3-beta modulator is a paullone, such as alsterpaullone, kenpaullone (9-bromo-7, 12-dihydroindolo[3,2-d][1]benzazepin-6(5H)-one), gwennpaullone (see Knockaert et al. "Intracellular Targets of Paullones. Identification following affinity purification on immobilized inhibitor." *J Biol Chem.* 2002 277(28):25493-501), azakenpaullone (see Kunick et al. "1-Azakenpaullone is a selective inhibitor of glycogen synthase kinase-3 beta." *Bioorg Med Chem Lett.* 2004 14(2):413-6), or the compounds described in U.S. Publication No. 20030181439; International Publication No. WO 01/60374; Leost et al., *Eur. J. Biochem.* 267:5983-5994 (2000); Kunick et al., J Med Chem.; 47(1): 22-36 (2004); or Shultz et al., J. Med. Chem. 42:2909-2919 (1999); an anticonvulsant, such as lithium or a derivative thereof (e.g., a compound described in U.S. Pat. Nos. 1,873,732; 3,814,812; and 4,301,176); valproic acid or a derivative thereof (e.g., valproate, or a compound described in Werstuck et al., Bioorg Med Chem Lett., 14(22): 5465-7 (2004)); lamotrigine; SL 76002 (Progabide), Gabapentin; tiagabine; or vigabatrin; a maleimide or a related compound, such as Ro 31-8220, SB-216763, SB-410111, SB-495052, or SB-415286, or a compound described, e.g., in U.S. Pat. No. 6,719,520; U.S. Publication No. 20040010031; International Publication Nos. WO-2004072062; WO-03082859; WO-03104222; WO-03103663, WO-03095452, WO-2005000836; WO 0021927; WO-03076398; WO-00021927; WO-00038675; or WO-03076442; or Coghlan et al., Chemistry & Biology 7:793 (2000); a pyridine or pyrimidine derivative, or a related compound (such as 5-iodotubercidin, GI 179186X, GW 784752X and GW 784775X, and compounds described, e.g., in U.S. Pat. Nos. 6,489,344; 6,417,185; and 6,153,618; U.S. Publication Nos. 20050171094; and 20030130289; European Patent Nos. EP-01454908, EP-01454910, EP-01295884, EP-01295885; and EP-01460076; EP-01454900; International Publication Nos. WO 01/70683; WO 01/70729; WO 01/70728; WO 01/70727; WO 01/70726; WO 01/70725; WO-00218385; WO-00218386; WO-03072579; WO-03072580; WO-03027115; WO-03027116; WO-2004078760; WO-2005037800, WO-2004026881, WO-03076437, WO-03029223; WO-2004098607; WO-2005026155; WO-2005026159; WO-2005025567; WO-03070730; WO-03070729; WO-2005019218; WO-2005019219; WO-2004013140; WO-2004080977; WO-2004026229, WO-2004022561; WO-03080616; WO-03080609; WO-03051847; WO-2004009602; WO-2004009596; WO-2004009597; WO-03045949; WO-03068773; WO-03080617; WO-99/65897; WO-00/18758; WO-0307073; WO-00220495; WO-2004043953, WO-2004056368, WO-2005012298, WO-2005012262, WO-2005042525, WO-2005005438, WO-2004009562, WO-03037877; WO-03037869; WO-03037891; WO-05012307; WO-05012304 and WO 98/16528; and in Massillon et al., Biochem J 299:123-8 (1994)); a pyrazine derivative, such as Aloisine A (7-n-Butyl-6-(4-hydroxyphenyl)[5H]pyrrolo[2,3-b]pyrazine) or a compound described in International Publication Nos. WO-00144206; WO0144246; or WO-2005035532; a thiadiazole or thiazole, such as TDZD-8 (Benzyl-2-methyl-1,2,4-thiadiazolidine-3,5-dione); OTDZT (4-Dibenzyl-5-oxothiadiazolidine-3-thione); or a related compound described, e.g., in U.S. Pat. Nos. 6,645, 990 or 6,762,179; U.S. Publication No. 20010039275; International Publication Nos. WO 01/56567, WO-03011843, WO-03004478, or WO-03089419; or Mettey, Y., et al., J. Med. Chem. 46, 222 (2003); TWS119 or a related compound, such as a compound described in Ding et al., Proc Natl Acad Sci U SA., 100(13): 7632-7 (2003); an indole derivative, such as a compound described in International Publication Nos. WO-03053330, WO-03053444, WO-03055877, WO-03055492, WO-03082853, or WO-2005027823; a pyrazine or pyrazole derivative, such as a compound described in U.S. Pat. Nos. 6,727,251, 6,696,452, 6,664,247, 666,073, 6,656,939, 6,653,301, 6,653,300, 6,638,926, 6,613,776, or 6,610,677; or International Publication Nos. WO-2005002552, WO-2005002576, or WO-2005012256; a compound described in U.S. Pat. Nos. 6,719,520; 6,498,176; 6,800,632; or 6,872,737; U.S. Publication Nos. 20050137201; 20050176713; 20050004125; 20040010031; 20030105075; 20030008866; 20010044436; 20040138273; or 20040214928; International Publication Nos. WO 99/21859; WO-00210158; WO-05051919; WO-00232896; WO-2004046117; WO-2004106343; WO-00210141; WO-00218346; WO 00/21927; WO 01/81345; WO 01/74771; WO 05/028475; WO 01/09106; WO 00/21927; WO01/41768; WO 00/17184; WO 04/037791; WO-04065370; WO 01/37819; WO 01/42224; WO 01/85685; WO 04/072063; WO-2004085439; WO-2005000303; WO-2005000304; or WO 99/47522; or Naerum, L., et al., Bioorg. Med. Chem. Lett. 12, 1525 (2002); CP-79049, GI 179186X, GW 784752X, GW 784775X, AZD-1080, AR-014418, SN-8914, SN-3728, TDZD-8, OTDZT, Aloisine A, TWSI 19, CHIR98023, CHIR99021, CHIR98014, CHIR98023, 5-iodotubercidin, Ro 31-8220, SB-216763, SB-410111, SB-495052, SB-415286, alsterpaullone, kenpaullone, gwennpaullone, LY294002, wortmannin, sildenafil, CT98014, CT-99025, flavoperidol, or L803-mts.

In yet further embodiments, the neurogenic agent used in combination with a muscarinic agent, such as an inhibitor of AChE activity, may be a reported glutamate modulator. In some embodiments, the reported mGlu receptor modulator is a Group II modulator, having activity against one or more Group II receptors (mGlu$_2$ and/or mGlu$_3$). Embodiments include those where the Group II modulator is a Group II agonist. Non-limiting xamples of Group II agonists include: (i) (1S,3R)-1-aminocyclopentane-1,3-dicarboxylic acid (ACPD), a broad spectrum mGlu agonist having substantial activity at Group I and II receptors; (ii) (−)-2-thia-4-aminobicyclo-hexane-4,6-dicarboxylate (LY389795), which is described in Monn et al., *J. Med. Chem.*, 42(6):1027-40 (1999); (iii) compounds described in US App. No. 20040102521 and Pellicciari et al., *J. Med. Chem.*, 39, 2259-2269 (1996); and (iv) the Group II-specific modulators described below.

Non-limiting examples of reported Group II antagonists include: (i) phenylglycine analogues, such as (RS)-alpha-methyl-4-sulphonophenylglycine (MSPG), (RS)-alpha-methyl-4-phosphonophenylglycine (MPPG), and (RS)-alpha-methyl-4-tetrazolylphenylglycine (MTPG), described in Jane et al., *Neuropharmacology* 34: 851-856 (1995); (ii) LY366457, which is described in O'Neill et al., *Neuropharmacol.*, 45(5): 565-74 (2003); (iii) compounds described in U.S. App Nos. 20050049243, 20050119345 and 20030157647; and (iv) the Group II-specific modulators described below.

In some non-limiting embodiments, the reported Group II modulator is a Group 11-selective modulator, capable of modulating $mGlu_2$ and/or $mGlu_3$ under conditions where it is substantially inactive at other mGlu subtypes (of Groups I and III). Examples of Group II-selective modulators include compounds described in Monn, et al., *J. Med. Chem.*, 40, 528-537 (1997); Schoepp, et al., *Neuropharmacol.*, 36, 1-11 (1997) (e.g., 1S,2S,5R, 6-S-2aminobicyclohexane-2,6-dicarboxylate); and Schoepp, Neurochem. Int., 24, 439 (1994).

Non-limiting examples of reported Group II-selective agonists include (i) (+)-2-aminobicyclohexane-2,6-dicarboxylic acid (LY354740), which is described in Johnson et al., *Drug Metab. Disposition*, 30(1): 27-33 (2002) and Bond et al., *NeuroReport* 8: 1463-1466 (1997), and is systemically active after oral administration (e.g., Grillon et al., *Psychopharmacol.* (Berl), 168: 446-454 (2003)); (ii) (−)-2-Oxa-4-aminobicyclohexane-4,6-dicarboxylic acid (LY379268), which is described in Monn et al., *J. Med. Chem.* 42: 1027-1040 (1999) and U.S. Pat. No. 5,688,826. LY379268 is readily permeable across the blood-brain barrier, and has $EC_{50}$ values in the low nanomolar range (e.g., below about 10 nM, or below about 5 nM) against human $mGlu_2$ and $mGlu_3$ receptors in vitro; (iii) (2R,4R)-4-aminopyrrolidine-2,4-dicarboxylate ((2R,4R)-APDC), which is described in Monn et al., *J. Med. Chem.* 39: 2990 (1996) and Schoepp et al., Neuropharmacology, 38: 1431 (1999); (iv) (1S,3S)-1-aminocyclopentane-1,3-dicarboxylic acid ((1S,3S)-ACPD), described in Schoepp, *Neurochem. Int.*, 24: 439 (1994); (v) (2R,4R)-4-aminopyrrolidine-2,4-dicarboxylic acid ((2R,4R)-APDC), described in Howson and Jane, *British Journal of Pharmacology*, 139, 147-155 (2003); (vi) (2S,1'S,2'S)-2-(carboxycyclopropyl)-glycine (L-CCG-I), described in Brabet et al., *Neuropharmacology* 37: 1043-1051 (1998); (vii) (2S,2'R,3'R)-2-(2',3'-dicarboxycyclopropyl)glycine (DCG-IV), described in Hayashi et al., *Nature*, 366, 687-690 (1993); (viii) 1S,2S,5R, 6S-2-aminobicyclohexane-2,6-dicarboxylate, described in Monn, et al., *J. Med. Chem.*, 40, 528 (1997) and Schoepp, et al., *Neuropharmacol.*, 36, 1 (1997); and (vii) compounds described in US App. No. 20040002478; U.S. Pat. Nos. 6,204,292, 6,333,428, 5,750,566 and 6,498,180; and Bond et al., *Neuroreport* 8: 1463-1466 (1997).

Non-limiting examples of reported Group II-selective antagonists useful in methods provided herein include the competitive antagonist (2S)-2-amino-2-(1S,2S-2-carboxycycloprop-1-yl)-3-(xanth-9-yl)propanoic acid (LY341495), which is described, e.g., in Kingston et al., *Neuropharmacology* 37:1-12 (1998) and Monn et al., *J Med Chem* 42: 1027-1040 (1999). LY341495 is readily permeably across the blood-brain barrier, and has $IC_{50}$ values in the low nanomolar range (e.g., below about 10 nM, or below about 5 nM) against cloned human $mGlu_2$ and $mGlu_3$ receptors. LY341495 has a high degree of selectivity for Group II receptors relative to Group I and Group III receptors at low concentrations (e.g., nanomolar range), whereas at higher concentrations (e.g., above 1 μM), LY341495 also has antagonist activity against $mGlu_7$ and $mGlu_8$, in addition to $mGlu_{2/3}$. LY341495 is substantially inactive against KA, AMPA, and NMDA iGlu receptors.

Additional non-limiting examples of reported Group II-selective antagonists include the following compounds, indicated by chemical name and/or described in the cited references: (i) α-methyl-L-(carboxycyclopropyl) glycine (CCG); (ii) (2S,3S,4S)-2-methyl-2-(carboxycyclopropyl) glycine (MCCG); (iii) (IR,2R,3R,5R,6R)-2-amino-3-(3,4-dichlorobenzyloxy)-6 fluorobicyclohexane-2,6-dicarboxylic acid (MGS0039), which is described in Nakazato et al., *J. Med. Chem.*, 47(18):4570-87 (2004); (iv) an n-hexyl, n-heptyl, n-octyl, 5-methylbutyl, or 6-methylpentyl ester prodrug of MGS0039; (v) MGS0210 (3-(3,4-dichlorobenzyloxy)-2-amino-6-fluorobicyclohexane-2,6-dicarboxylic acid n-heptyl ester); (vi) (RS)-1-amino-5-phosphonoindan-1-carboxylic acid (APICA), which is described in Ma et al., *Bioorg. Med. Chem. Lett.*, 7: 1195 (1997); (vii) (2S)-ethylglutamic acid (EGLU), which is described in Thomas et al., *Br. J. Pharmacol.* 117: 70P (1996); (viii) (2S,1'S,2'S,3'R)-2-(2'-carboxy-3'-phenylcyclopropyl)glycine (PCCG-IV); and (ix) compounds described in U.S. Pat. No. 6,107,342 and US App No. 20040006114. APICA has an $IC_{50}$ value of approximately 30 μM against $mGluR_2$ and $mGluR_3$, with no appreciable activity against Group I or Group III receptors at sub-mM concentrations.

In some non-limiting embodiments, a reported Group II-selective modulator is a subtype-selective modulator, capable of modulating the activity of $mGlu_2$ under conditions in which it is substantially inactive at $mGlu_3$ ($mGlu_2$-selective), or vice versa ($mGlu_3$-selective). Non-limiting examples of subtype-selective modulators include compounds described in U.S. Pat. No. 6,376,532 ($mGlu_2$-selective agonists) and US App No. 20040002478 ($mGlu_3$-selective agonists). Additional non-limiting examples of subtype-selective modulators include allosteric mGlu receptor modulators ($mGlu_2$ and $mGlu_3$) and NAAG-related compounds ($mGlu_3$), such as those described below.

In other non-limiting embodiments, a reported Group II modulator is a compound with activity at Group I and/or Group III receptors, in addition to Group II receptors, while having selectivity with respect to one or more mGlu receptor subtypes. Non-limiting examples of such compounds include: (i) (2S,3S,4S)-2-(carboxycyclopropyl)glycine (L-CCG-1) (Group I/Group II agonist), which is described in Nicoletti et al., *Trends Neurosci.* 19: 267-271 (1996), Nakagawa, et al., *Eur. J. Pharmacol.*, 184, 205 (1990), Hayashi, et al., *Br. J. Pharmacol.*, 107, 539 (1992), and Schoepp et al., *J. Neurochem.*, 63., page 769-772 (1994); (ii) (S)-4-carboxy-3-hydroxyphenylglycine ($4C_3HPG$) (Group II agonist/Group I competitive antagonist); (iii) gamma-carboxy-L-glutamic acid (GLA) (Group II antagonist/Group III partial agonist/antagonist); (iv) (2S,2'R,3'R)-2-(2,3-dicarboxycyclopropyl) glycine (DCG-IV) (Group II agonist/Group III antagonist), which is described in Ohfune et al, *Bioorg. Med. Chem. Lett.*, 3: 15 (1993); (v) (RS)-a-methyl-4-carboxyphenylglycine (MCPG) (Group I/Group II competitive antagonist), which is described in Eaton et al., *Eur. J. Pharmacol.*, 244: 195 (1993), Collingridge and Watkins, TiPS, 15: 333 (1994), and Joly et al., *J. Neurosci.*, 15: 3970 (1995); and (vi) the Group II/III modulators described in U.S. Pat. Nos. 5,916,920, 5,688,826, 5,945,417, 5,958,960, 6,143,783, 6,268,507, 6,284,785.

In some non-limiting embodiments, the reported mGlu receptor modulator comprises (S)-MCPG (the active isomer of the Group I/Group II competitive antagonist (RS)-MCPG) substantially free from (R)-MCPG. (S)-MCPG is described, e.g., in Sekiyama et al., *Br. J. Pharmacol.*, 117: 1493 (1996) and Collingridge and Watkins, *TiPS*, 15: 333 (1994).

Additional non-limiting examples of reported mGlu modulators useful in methods disclosed herein include compounds described in U.S. Pat. Nos. 6,956,049, 6,825,211, 5,473,077, 5,912,248, 6,054,448, and 5,500,420; US App Nos. 20040077599, 20040147482, 20040102521, 20030199533 and 20050234048; and Intl Pub/App Nos. WO 97/19049, WO 98/00391, and EP0870760.

In some non-limiting embodiments, the reported mGlu receptor modulator is a prodrug, metabolite, or other derivative of N-Acetylaspartylglutamate (NAAG), a peptide neurotransmitter in the mammalian CNS that is a highly selective agonist for mGluR$_3$ receptors, as described in Wroblewska et al., *J. Neurochem.*, 69(1): 174-181 (1997). In other embodiments, the mglu modulator is a compound that modulates the levels of endogenous NAAG, such as an inhibitor of the enzyme N-acetylated-alpha-linked-acidic dipeptidase (NAALADase), which catalyzes the hydrolysis of NAAG to N-acetyl-aspartate and glutamate. Examples of NAALADase inhibitors include 2-PMPA (2-(phosphonomethyl)pentanedioic acid), which is described in Slusher et al., *Nat. Med.*, 5(12): 1396-402 (1999); and compounds described in *J. Med. Chem.* 39: 619 (1996), US Pub. No. 20040002478, and U.S. Pat. Nos. 6,313,159, 6,479,470, and 6,528,499. In some embodiments, the mGlu modulator is the mGlu$_3$-selective antagonist, beta-NAAG.

Additional non-limiting examples of reported glutamate modulators include memantine (CAS RN 19982-08-2), memantine hydrochloride (CAS RN 41100-52-1), and riluzole (CAS RN 1744-22-5).

In some non-limiting embodiments, a reported Group II modulator is administered in combination with one or more additional compounds reported as active against a Group I and/or a Group III mGlu receptor. For example, in some cases, methods comprise modulating the activity of at least one Group I receptor and at least one Group II mGlu receptor (e.g., with a compound described herein). Examples of compounds useful in modulating the activity of Group I receptors include Group I-selective agonists, such as (i) trans-azetidine-2,4,-dicarboxylic acid (tADA), which is described in Kozikowski et al., *J. Med. Chem.*, 36: 2706 (1993) and Manahan-Vaughan et al., *Neuroscience*, 72: 999 (1996); (ii) (RS)-3,5-Dihydroxyphenylglycine (DHPG), which is described in Ito et al., *NeuroReport* 3: 1013 (1992); or a composition comprising (S)-DHPG substantially free of (R)-DHPG, as described, e.g., in Baker et al., *Bioorg.Med.Chem.Lett.* 5: 223 (1995); (iii) (RS)-3-Hydroxyphenylglycine, which is described in Birse et al., *Neuroscience* 52: 481 (1993); or a composition comprising (S)-3-Hydroxyphenylglycine substantially free of (R)-3-Hydroxyphenylglycine, as described, e.g., in Hayashi et al., *J.Neurosci.*, 14: 3370 (1994); (iv) and (S)-Homoquisqualate, which is described in Porter et al., *Br. J. Pharmacol.*, 106: 509 (1992).

Additional non-limiting examples of reported Group I modulators include (i) Group I agonists, such as (RS)-3,5-dihydroxyphenylglycine, described in Brabet et al., *Neuropharmacology*, 34, 895-903, 1995; and compounds described in U.S. Pat. Nos. 6,399,641 and 6,589,978, and US Pub No. 20030212066; (ii) Group I antagonists, such as (S)-4-Carboxy-3-hydroxyphenylglycine; 7-(Hydroxyimino)cyclopropa-0-chromen-1α-carboxylate ethyl ester; (RS)-1-Aminoindan-1,5-dicarboxylic acid (AIDA); 2-Methyl-6 (phenylethynyl)pyridine (MPEP); 2-Methyl-6-(2-phenylethenyl)pyridine (SIB-1893); 6-Methyl-2-(phenylazo)-3-pyridinol (SIB-1757); (Sa-Amino-4-carboxy-2-methylbenzeneacetic acid; and compounds described in U.S. Pat. Nos. 6,586,422, 5,783,575, 5,843,988, 5,536,721, 6,429,207, 5,696,148, and 6,218,385, and US Pub Nos. 20030109504, 20030013715, 20050154027, 20050004130, 20050209273, 20050197361, and 20040082592; (iii) mGlu$_5$-selective agonists, such as (RS)-2-Chloro-5-hydroxyphenylglycine (CHPG); and (iv) mGlu$_5$-selective antagonists, such as 2-methyl-6-(phenylethynyl)-pyridine (MPEP); and compounds described in U.S. Pat. No. 6,660,753; and US Pub Nos. 20030195139, 20040229917, 20050153986, 20050085514, 20050065340, 20050026963, 20050020585, and 20040259917.

Non-limiting examples of compounds reported to modulate Group III receptors include (i) the Group III-selective agonists (L)-2-amino-4-phosphonobutyric acid (L-AP4), described in Knopfel et al., *J. Med Chem.*, 38, 1417-1426 (1995); and (S)-2-Amino-2-methyl-4-phosphonobutanoic acid; (ii) the Group III-selective antagonists (RS)-α-Cyclopropyl-4-phosphonophenylglycine; (RS)-α-Methylserine-O-phosphate (MSOP); and compounds described in US App. No. 20030109504; and (iii) (1S,3R,4S)-1-aminocyclopentane-1,2,4-tricarboxylic acid (ACPT-I).

In additional embodiments, the neurogenic agent used in combination with a muscarinic agent, such as an inhibitor of AChE activity, may be an AMPA modulator. Non-limiting examples include CX-516 or ampalex (CAS RN 154235-83-3), Org-24448 (CAS RN 211735-76-1), LY451395 (2-propanesulfonamide, N-[(2R)-2-[4'-[2-[methylsulfonyl)amino] ethyl][1,1'-biphenyl]-4-yl]propyl]-), LY-450108 (see Jhee et al. "Multiple-dose plasma pharmacokinetic and safety study of LY450108 and LY451395 (AMPA receptor potentiators) and their concentration in cerebrospinal fluid in healthy human subjects." *J Clin Pharmacol.* 2006 46(4):424-32), and CX717. Additional examples of reported antagonists include irampanel (CAS RN 206260-33-5) and E-2007.

Further non-limiting examples of reported AMPA receptor antagonists for use in combinations include YM9OK (CAS RN 154164-30-4), YM872 or Zonampanel (CAS RN 210245-80-0), NBQX (or 2,3-Dioxo-6-nitro-7-sulfamoyl-benzo(f)quinoxaline; CAS RN 118876-58-7), PNQX (1,4,7,8,9,10-hexahydro-9-methyl-6-nitropyrido[3, 4-f]quinoxaline-2,3-di and ZK200775 ([1,2,3,4-tetrahydro-7-morpholinyl-2,3-dioxo-6-(fluoromethyl) quinoxalin-1-yl] methylphosphonate).

In yet additional embodiments, the neurogenic agent in combination with a muscarinic agent, such as an inhibitor of AChE activity, is a reported HDAC inhibitor. The term "HDAC" refers to any one of a family of enzymes that remove acetyl groups from the epsilon-amino groups of lysine residues at the N-terminus of a histone. An HDAC inhibitor refers to compounds capable of inhibiting, reducing, or otherwise modulating the deacetylation of histones mediated by a histone deacetylase. Non-limiting examples of a reported HDAC inhibitor include a short-chain fatty acid, such as butyric acid, phenylbutyrate (PB), 4-phenylbutyrate (4-PBA), pivaloyloxymethyl butyrate (Pivanex, AN-9), isovalerate, valerate, valproate, valproic acid, propionate, butyramide, isobutyramide, phenylacetate, 3-bromopropionate, or tributyrin; a compound bearing a hydroxyamic acid group, such as suberoylanlide hydroxamic acid (SAHA), trichostatin A (TSA), trichostatin C (TSC), salicylhydroxamic acid, oxamflatin, suberic bishydroxamic acid (SBHA), m-carboxy-cinnamic acid bishydroxamic acid (CBHA), pyroxamide (CAS RN 382180-17-8), diethyl bis-(pentamethylene-N,N-dimethyl-carboxamide) malonate (EMBA), azelaic bishydroxamic acid (ABHA), azelaic-1-hydroxamate-9-anilide (AAHA), 6-(3-Chlorophenylureido) carpoic hydroxamic acid, or A-161906; a cyclic tetrapeptide, such as Depsipeptide (FK228), FR225497, trapoxin A, apicidin, chlamydocin, or HC-toxin; a benzamide, such as MS-275; depudecin, a sulfonamide anilide (e.g., diallyl sulfide), BL1521, curcumin (diferuloylmethane), CI-994 (N-acetyldinaline), spiruchostatin A, Scriptaid, carbamazepine (CBZ), or a related compound; a compound comprising a cyclic tetrapeptide group and a hydroxamic acid group (examples of such compounds are described in U.S. Pat. Nos. 6,833,384 and 6,552,065); a compound comprising a benzamide group and a hydroxamic acid group (examples of such compounds are described in Ryu et al., Cancer Lett. 2005 Jul. 9 (epub), Plumb et al., Mol Cancer Ther., 2(8):721-8 (2003), Ragno et al., J Med Chem., 47(6):1351-9 (2004), Mai et al., J Med Chem., 47(5):1098-109 (2004), Mai et al., J Chem., 46(4):512-24 (2003), Mai et al., J Med Chem., 45(9):1778-84 (2002), Massa et Med Chem., 44(13):2069-72 (2001), Mai et al., J Med Chem., 48(9):3344-53 (2005), an et al., J Med Chem., 46(23):4826-9 (2003)); a compound described in U.S. Pat. Nos. 6,897,220, 6,888,027, 5,369,108, 6,541,661, 6,720,445, 6,562,995, 6,777,217, or 6,387,673, or U.S. Patent Publication Nos. 20050171347, 20050165016, 20050159470, 20050143385, 20050137234, 20050137232, 20050119250, 20050113373, 20050107445, 20050107384, 20050096468, 20050085515, 20050032831, 20050014839, 20040266769, 20040254220, 20040229889, 20040198830, 20040142953, 20040106599, 20040092598, 20040077726, 20040077698, 20040053960, 20030187027, 20020177594, 20020161045, 20020119996, 20020115826, 20020103192, or 20020065282; FK228, AN-9, MS-275, CI-994, SAHA, G2M-777, PXD-101, LBH-589, MGCD-0103, MK0683, sodium phenylbutyrate, CRA-024781, and derivatives, salts, metabolites, prodrugs, and stereoisomers thereof; and a molecule that inhibits the transcription and/or translation of one or more HDACs.

Additional non-limiting examples include a reported HDac inhibitor selected from ONO-2506 or arundic acid (CAS RN 185517-21-9); MGCD0103 (see Gelmon et al. "Phase I trials of the oral histone deacetylase (HDAC) inhibitor MGCD0103 given either daily or 3×weekly for 14 days every 3 weeks in patients (pts) with advanced solid tumors." *Journal of Clinical Oncology*, 2005 ASCO Annual Meeting Proceedings. 23(16S, June 1 Supplement), 2005: 3147 and Kalita et al. "Pharmacodynamic effect of MGCD0103, an oral isotype-selective histone deacetylase (HDAC) inhibitor, on HDAC enzyme inhibition and histone acetylation induction in Phase I clinical trials in patients (pts) with advanced solid tumors or non-Hodgkin's lymphoma (NHL)" *Journal of Clinical Oncology*, 2005 ASCO Annual Meeting Proceedings. 23(16S, Part I of II, June 1 Supplement), 2005: 9631), a reported thiophenyl derivative of benzamide HDac inhibitor as presented at the 97th American Association for Cancer Research (AACR) Annual Meeting in Washington, D.C. in a poster titled "Enhanced Isotype-Selectivity and Antiproliferative Activity of Thiophenyl Derivatives of BenzamideHDAC Inhibitors In Human Cancer Cells," (abstract #4725), and a reported HDac inhibitor as described in U.S. Pat. No. 6,541,661; SAHA or Vorinostat (CAS RN 149647-78-9); PXD101 or PXD 101 or PX 105684 (CAS RN 414864-00-9); CI-994 or Tacedinaline (CAS RN 112522-64-2), MS-275 (CAS RN 209783-80-2), or an inhibitor reported in WO2005/108367.

In other embodiments, the neurogenic agent in combination with a muscarinic agent, such as an inhibitor of AChE activity, is a reported GABA modulator which modulates GABA receptor activity at the receptor level (e.g., by binding directly to GABA receptors), at the transcriptional and/or translational level (e.g., by preventing GABA receptor gene expression), and/or by other modes (e.g., by binding to a ligand or effector of a GABA receptor, or by modulating the activity of an agent that directly or indirectly modulates GABA receptor activity). Non-limiting examples of GABA-A receptor modulators useful in methods described herein include triazolophthalazine derivatives, such as those disclosed in WO 99/25353, and WO/98/04560; tricyclic pyrazolo-pyridazinone analogues, such as those disclosed in WO 99/00391; fenamates, such as those disclosed in U.S. Pat. No. 5,637,617; triazolo-pyridazine derivatives, such as those disclosed in WO 99/37649, WO 99/37648, and WO 99/37644; pyrazolo-pyridine derivatives, such as those disclosed in WO 99/48892; nicotinic derivatives, such as those disclosed in WO 99/43661 and U.S. Pat. No. 5,723,462; muscimol, thiomuscimol, and compounds disclosed in U.S. Pat. No. 3,242, 190; baclofen and compounds disclosed in U.S. Pat. No. 3,471,548; phaclofen; quisqualamine; ZAPA; zaleplon; THIP; imidazole-4-acetic acid (IMA); (+)-bicuculline; gaba-linoleamide; isoguvicaine; 3-aminopropane sulphonic acid; piperidine-4-sulphonic acid; 4,5,6,7-tetrahydro-[5,4-c]-pyridin-3-ol; SR 95531; RU5315; CGP 55845; CGP 35348; FG 8094; SCH 50911; NG2-73; NGD-96-3; picrotoxin and other bicyclophosphates disclosed in Bowery et al., Br. J. Pharmacol., 57; 435 (1976).

The combination of the muscarinic agent tacrine with baclofen resulted in synergistic activity (see Example 8 below). See also Example 12 for a discussion of synergy. Tacrine alone has an $EC_{50}$ of 8.0 µM for neuronal differentiation. Baclofen alone has an $EC_{50}$ of 3.6 µM. The concentration of each agent in combination to reach 50% activity in neuronal differentiation is 1.8 µM, resulting in a CI of 0.84. As the CI is less than 1, the two compounds have a synergistic effect in neuronal differentiation.

Additional non-limiting examples of GABA-A modulators include compounds described in U.S. Pat. Nos. 6,503,925; 6,218,547; 6,399,604; 6,646,124; 6,515,140; 6,451,809; 6,448,259; 6,448,246; 6,423,711; 6,414,147; 6,399,604; 6,380,209; 6,353,109; 6,297,256; 6,297,252; 6,268,496; 6,211,365; 6,166,203; 6,177,569; 6,194,427; 6,156,898; 6,143,760; 6,127,395; 6,103,903; 6,103,731; 6,723,735; 6,479,506; 6,476,030; 6,337,331; 6,730,676; 6,730,681; 6,828,322; 6,872,720; 6,699,859; 6,696,444; 6,617,326; 6,608,062; 6,579,875; 6,541,484; 6,500,828; 6,355,798; 6,333,336; 6,319,924; 6,303,605; 6,303,597; 6,291,460; 6,255,305; 6,133,255; 6,872,731; 6,900,215; 6,642,229; 6,593,325; 6,914,060; 6,914,063; 6,914,065; 6,936,608; 6,534,505; 6,426,343; 6,313,125; 6,310,203; 6,200,975; 6,071,909; 5,922,724; 6,096,887; 6,080,873; 6,013,799; 5,936,095; 5,925,770; 5,910,590; 5,908,932; 5,849,927; 5,840,888; 5,817,813; 5,804,686; 5,792,766; 5,750,702; 5,744,603; 5,744,602; 5,723,462; 5,696,260; 5,693,801; 5,677,309; 5,668,283; 5,637,725; 5,637,724; 5,625,063; 5,610,299; 5,608,079; 5,606,059; 5,604,235; 5,585,490; 5,510,480; 5,484,944; 5,473,073; 5,463,054; 5,451,585; 5,426,186; 5,367,077; 5,328,912; 5,326,868; 5,312,822; 5,306,819; 5,286,860; 5,266,698; 5,243,049; 5,216,159; 5,212,310; 5,185,446; 5,185,446; 5,182,290; 5,130,430; 5,095,015; 20050014939; 20040171633; 20050165048; 20050165023; 20040259818; and 20040192692.

In some embodiments, the GABA-A modulator is a subunit-selective modulator. Non-limiting examples of GABA-A modulator having specificity for the alpha1 subunit include alpidem and zolpidem. Non-limiting examples of GABA-A modulator having specificity for the alpha2 and/or alpha3 subunits include compounds described in U.S. Pat. Nos. 6,730,681; 6,828,322; 6,872,720; 6,699,859; 6,696,444; 6,617,326; 6,608,062; 6,579,875; 6,541,484; 6,500,828; 6,355,798; 6,333,336; 6,319,924; 6,303,605; 6,303,597; 6,291,460; 6,255,305; 6,133,255; 6,900,215; 6,642,229; 6,593,325; and 6,914,063. Non-limiting examples of GABA-A modulator having specificity for the alpha2, alpha3 and/or alpha5 subunits include compounds described in U.S. Pat. Nos. 6,730,676 and 6,936,608. Non-limiting examples of GABA-A modulators having specificity for the alpha5 subunit include compounds described in U.S. Pat. Nos. 6,534,505; 6,426,343; 6,313,125; 6,310,203; 6,200,975 and 6,399,604. Additional non-limiting subunit selective GABA-A modulators include CL218,872 and related compounds disclosed in Squires et al., *Pharmacol. Biochem. Behav.*, 10: 825 (1979); and beta-carboline-3-carboxylic acid esters described in Nielsen et al., *Nature,* 286: 606 (1980).

In some embodiments, the GABA-A receptor modulator is a reported allosteric modulator. In various embodiments, allosteric modulators modulate one or more aspects of the activity of GABA at the target GABA receptor, such as potency, maximal effect, affinity, and/or responsiveness to other GABA modulators. In some embodiments, allosteric modulators potentiate the effect of GABA (e.g., positive allosteric modulators), and/or reduce the effect of GABA (e.g., inverse agonists). Non-limiting examples of benzodiazepine GABA-A modulators include aiprazolam, bentazepam, bretazenil, bromazepam, brotizolam, cannazepam, chlordiazepoxide, clobazam, clonazepam, cinolazepam, clotiazepam, cloxazolam, clozapin, delorazepam, diazepam, dibenzepin, dipotassium chlorazepat, divaplon, estazolam, ethylloflazepat, etizolam, fludiazepam, flumazenil, flunitrazepam, flurazepamI 1HCl, flutoprazepam, halazepam, haloxazolam, imidazenil, ketazolam, lorazepam, loprazolam, lormetazepam, medazepam, metaclazepam, mexozolam, midazolam-HCl, nabanezil, nimetazepam, nitrazepam, nordazepam, oxazepam-tazepam, oxazolam, pinazepam, prazepam, quazepam, sarmazenil, suriclone, temazepam, tetrazepam, tofisopam, triazolam, zaleplon, zolezepam, zolpidem, zopiclone, and zopielon.

Additional non-limiting examples of benzodiazepine GABA-A modulators include Rol5-4513, CL218872, CGS 8216, CGS 9895, PK 9084, U-93631, beta-CCM, beta-CCB, beta-CCP, Ro 19-8022, CGS 20625, NNC 14-0590, Ru 33-203, 5-amino-1-bromouracil, GYKI-52322, FG 8205, Ro 19-4603, ZG-63, RWJ46771, SX-3228, and L-655,078; NNC 14-0578, NNC 14-8198, and additional compounds described in Wong et al., *Eur J Pharmacol* 209: 319-325 (1995); Y-23684 and additional compounds in Yasumatsu et al., Br J Pharmacol 111: 1170-1178 (1994); and compounds described in U.S. Pat. No. 4,513,135.

Non-limiting examples of barbiturate or barbituric acid derivative GABA-A modulators include phenobarbital, pentobarbital, pentobarbitone, primidone, barbexaclon, dipropyl barbituric acid, eunarcon, hexobarbital, mephobarbital, methohexital, Na-methohexital, 2,4,6(1H,3H,5)-pyrimidintrion, secbutabarbital and/or thiopental.

Non-limiting examples of neurosteroid GABA-A modulators include alphaxalone, allotetrahydrodeoxycorticosterone, tetrahydrodeoxycorticosterone, estrogen, progesterone 3-beta-hydroxyandrost-5-en-17-on-3-sulfate, dehydroepiandrosterone, eltanolone, ethinylestradiol, 5-pregnen-3-beta-ol-20 on-sulfate, 5a-pregnan-3a-ol-20-one (5PG), allopregnanolone, pregnanolone, and steroid derivatives and metabolites described in U.S. Pat. Nos. 5,939,545, 5,925,630, 6,277,838, 6,143,736, RE35,517, 5,925,630, 5,591,733, 5,232,917, 20050176976, WO 96116076, WO 98/05337, WO 95/21617, WO 94/27608, WO 93/18053, WO 93/05786, WO 93/03732,, WO 91116897, EP01038880, and Han et al., *J. Med. Chem.,* 36, 3956-3967 (1993), Anderson et al., *J. Med. Chem.,* 40, 1668-1681 (1997), Hogenkamp et al., *J. Med. Chem.,* 40, 61-72 (1997), Upasani et al., *J. Med. Chem.,* 40, 73-84 (1997), Majewska et al., *Science* 232:1004-1007 (1986), Harrison et al., *J. Pharmacol. Exp. Ther.* 241:346-353 (1987), Gee et al., *Eur. J. Pharmacol.,* 136:419-423 (1987) and Birtran et al., *Brain Res.,* 561, 157-161 (1991).

Non-limiting examples of beta-carboline GABA-A modulators include abecarnil, 3,4-dihydro-beta-carboline, gedocarnil, 1-methyl-1-vinyl-2,3,4-trihydro-beta-carboline-3-carboxylic acid, 6-methoxy-1,2,3,4-tetrahydro-beta-carboline, N-BOC-L-1,2,3,4-tetrahydro-beta-carboline-3-carboxylic acid, tryptoline, pinoline, methoxyharmalan, tetrahydro-beta-carboline (THBC), 1-methyl-THBC, 6-methoxy-THBC, 6-hydroxy-THBC, 6-methoxyharmalan, norharman, 3,4-dihydro-beta-carboline, and compounds described in Nielsen et al., Nature, 286: 606 (1980).

In some embodiments, the GABA modulator modulates GABA-B receptor activity. Non-limiting examples of reported GABA-B receptor modulators useful in methods described herein include CGP36742; CGP-64213; CGP 56999A; CGP 54433A; CGP 36742; SCH 50911; CGP 7930; CGP 13501; baclofen and compounds disclosed in U.S. Pat. No. 3,471,548; saclofen; phaclofen; 2-hydroxysaclofen; SKF 97541; CGP 35348 and related compounds described in Olpe, et al, *Eur. J. Pharmacol.,* 187, 27 (1990); phosphinic acid derivatives described in Hills, et al, *Br. J. Pharmacol.,* 102, pp. 5-6 (1991); and compounds described in U.S. Pat. Nos. 4,656,298, 5,929,236, EP0463969, EP 0356128, Kaupmann et al., *Nature* 368: 239 (1997), Karla et al., *J Med Chem.,* 42(11):2053-9 (1992), Ansar et al., *Therapie,* 54(5):651-8 (1999), and Castelli et al., *Eur J Pharmacol.,* 446(1-3):1-5 (2002).

In some embodiments, the GABA modulator modulates GABA-C receptor activity. Non-limiting examples of reported GABA-C receptor modulators useful in methods described herein include cis-aminocrotonic acid (CACA); 1,2,5,6-tetrahydropyridine-4-yl methyl phosphinic acid (TP-MPA) and related compounds such as P4MPA, PPA and SEPI; 2-methyl-TACA; (+/−)-TAMP; muscimol and compounds disclosed in U.S. Pat. No. 3,242,190; ZAPA; THIP and related analogues, such as aza-THIP; pricotroxin; imidazole-4-acetic acid (IMA); and CGP36742.

In some embodiments, the GABA modulator modulates the activity of glutamic acid decarboxylase (GAD).

In some embodiments, the GABA modulator modulates GABA transaminase (GTA). Non-limiting examples of GTA modulators include the GABA analogue vigabatrin and compounds disclosed in U.S. Pat. No. 3,960,927.

In some embodiments, the GABA modulator modulates the reuptake and/or transport of GABA from extracellular regions. In other embodiments, the GABA modulator modulates the activity of the GABA transporters, GAT-1, GAT-2, GAT-3 and/or BGT-1. Non-limiting examples of GABA reuptake and/or transport modulators include nipecotic acid and related derivatives, such as CI 966; SKF 89976A; TACA; stiripentol; tiagabine and GAT-1 inhibitors disclosed in U.S. Pat. No. 5,010,090; (R)-1-(4,4-diphenyl-3-butenyl)-3-piperidinecarboxylic acid and related compounds disclosed in U.S. Pat. No. 4,383,999; (R)-1-[4,4-bis(3-methyl-2-thienyl)-3-butenyl]-3-piperidinecarboxylic acid and related compounds disclosed in Anderson et al., *J. Med. Chem.* 36, (1993) 1716-1725; guvacine and related compounds disclosed in Krogsgaard-Larsen, *Molecular & Cellular Biochemistry* 31, 105-121 (1980); GAT-4 inhibitors disclosed in U.S. Pat. No. 6,071,932; and compounds disclosed in U.S. Pat. No. 6,906,177 and Ali, F. E., et al. *J. Med. Chem.* 1985, 28, 653-660. Methods for detecting GABA reuptake inhibitors are known in the art, and are described, e.g., in U.S. Pat. Nos. 6,906,177; 6,225,115; 4,383,999; Ali, F. E., et al. *J. Med. Chem.* 1985, 28, 653-660.

In some embodiments, the GABA modulator is the benzodiazepine Clonazepam, which is described, e.g., in U.S. Pat. Nos. 3,121,076 and 3,116,203; the benzodiazepine Diazepam, which is described, e.g., in U.S. Pat. Nos. 3,371,085; 3,109,843; and 3,136,815; the short-acting diazepam derivative Midazolam, which is a described, e.g., in U.S. Pat. No. 4,280,957; the imidazodiazepine Flumazenil, which is described, e.g., in U.S. Pat. No. 4,316,839; the benzodiazepine Lorazepam is described, e.g., in U.S. Pat. No. 3,296,249; the benzodiazepine L-655708, which is described, e.g., in Quirk et al. *Neuropharmacology* 1996, 35, 1331; Sur et al. *Mol. Pharmacol.* 1998, 54, 928; and Sur et al. *Brain Res.* 1999, 822, 265; the benzodiazepine Gabitril; Zopiclone, which binds the benzodiazepine site on GABA-A receptors, and is disclosed, e.g., in U.S. Pat. Nos. 3,862,149 and 4,220,646.; the GABA-A potentiator Indiplon as described, e.g., in Foster et al., *J Pharmacol Exp Ther.,* 311(2):547-59 (2004), U.S. Pat. Nos. 4,521,422 and 4,900,836; Zolpidem, described, e.g., in U.S. Pat. No. 4,794,185 and EP50563; Zaleplon, described, e.g., in U.S. Pat. No. 4,626,538; Abecarnil, described, e.g., in Stephens et al., *J Pharmacol Exp Ther.,* 253(1):334-43 (1990); the GABA-A agonist Isoguvacine, which is described, e.g., in Chebib et al., *Clin. Exp. Pharmacol. Physiol.* 1999, 26, 937-940; Leinekugel et al. *J. Physiol.* 1995, 487, 319-29; and White et al., *J. Neurochem.* 1983, 40(6), 1701-8; the GABA-A agonist Gaboxadol (THIP), which is described, e.g., in U.S. Pat. No. 4,278,676 and Krogsgaard-Larsen, *Acta. Chem. Scand.* 1977, 31, 584; the GABA-A agonist Muscimol, which is described, e.g., in U.S. Pat. Nos. 3,242,190 and 3,397,209; the inverse GABA-A agonist beta-CCP, which is described, e.g., in Nielsen et al., *J. Neurochem.,* 36(1):276-85 (1981); the GABA-A potentiator Riluzole, which is described, e.g., in U.S. Pat. No. 4,370,338 and EP 50,551; the GABA-B agonist and GABA-C antagonist SKF 97541, which is described, e.g., in Froestl et al., *J. Med. Chem.* 38 3297 (1995); Hoskison et al., *Neurosci. Lett.* 2004, 365(1), 48-53 and Hue et al., *J. Insect Physiol.* 1997, 43(12), 1125-1131; the GABA-B agonist Baclofen, which is described, e.g., in U.S. Pat. No. 3,471,548; the GABA-C agonist cis-4-aminocrotonic acid (CACA), which is described, e.g., in Ulloor et al. *J. Neurophysiol.* 2004, 91(4), 1822-31; the GABA-A antagonist Phaclofen, which is described, e.g., in Kerr et al. *Brain Res.* 1987, 405, 150; Karlsson et al. *Eur. J Pharmacol.* 1988, 148, 485; and Hasuo, Gallagher *Neurosci. Lett.* 1988, 86, 77; the GABA-A antagonist SR 95531, which is described, e.g., in Stell et al. *J. Neurosci.* 2002, 22(10), RC223; Wermuth et al., *J. Med. Chem.* 30 239 (1987); and Luddens and Korpi, *J. Neurosci.* 15: 6957 (1995); the GABA-A antagonist Bicuculline, which is a described, e.g., in Groenewoud, *J. Chem. Soc.* 1936, 199; Olsen et al., *Brain Res.* 102: 283 (1976) and Haworth et al. *Nature* 1950, 165, 529; the selective GABA-B antagonist CGP 35348, which is described, e.g., in Olpe et al. *Eur. J. Pharmacol.* 1990, 187, 27; Hao et al. *Neurosci. Lett.* 1994, 182, 299; and Froestl et al. *Pharmacol. Rev. Comm.* 1996, 8, 127; the selective GABA-B antagonist CGP 46381, which is described, e.g., in Lingenhoehl, *Pharmacol. Comm.* 1993, 3, 49; the selective GABA-B antagonist CGP 52432, which is described, e.g., in Lanza et al. *Eur. J. Pharmacol.* 1993, 237, 191; Froestl et al. *Pharmacol. Rev. Comm.* 1996, 8, 127; Bonanno et al. *Eur. J. Pharmacol.* 1998, 362, 143; and Libri et al. *Naunyn-Schmied. Arch. Pharmacol.* 1998, 358, 168; the selective GABA-B antagonist CGP 54626, which is described, e.g., in Brugger et al. *Eur. J. Pharmacol.* 1993, 235, 153; Froestl et al. *Pharmacol. Rev. Comm.* 1996, 8, 127; and Kaupmann et al. *Nature* 1998, 396, 683; the selective GABA-B antagonist CGP 55845, which is a GABA-receptor antagonist described, e.g., in Davies et al. *Neuropharmacology* 1993, 32, 1071; Froestl et al. *Pharmacol. Rev. Comm.* 1996, 8, 127; and Deisz *Neuroscience* 1999, 93, 1241; the selective GABA-B antagonist Saclofen, which is described, e.g., in Bowery, *TiPS,* 1989, 10, 401; and Kerr et al. *Neurosci Lett.* 1988;92(1):92-6; the GABA-B antagonist 2-Hydroxysaclofen, which is described, e.g., in Kerr et al. *Neurosci. Lett.* 1988, 92, 92; and Curtis et al. *Neurosci. Lett.* 1988, 92, 97; the GABA-B antagonist SCH 50,911, which is described, e.g., in Carruthers et al., *Bioorg Med Chem Lett* 8: 3059-3064 (1998); Bolser et al. *J. Pharmacol. Exp. Ther.* 1996, 274, 1393; Hosford et al. *J. Pharmacol. Exp. Ther.* 1996, 274, 1399; and Ong et al. *Eur. J. Pharmacol.* 1998, 362, 35; the selective GABA-C antagonist TPMPA, which is described, e.g., in Schlicker et al., *Brain Res. Bull.* 2004, 63(2), 91-7; Murata et al., *Bioorg. Med. Chem. Lett.* 6: 2073 (1996); and Ragozzino et al., *Mol. Pharmacol.* 50: 1024 (1996); a GABA derivative, such as Pregabalin [(S)-(+)-3-isobutylgaba] or gabapentin [1-(aminomethyl)cyclohexane acetic acid]. Gabapentin is described, e.g., in U.S. Pat. No. 4,024,175; the lipid-soluble GABA agonist Progabide, which is metabolized in vivo into GABA and/or pharmaceutically active GABA derivatives in vivo. Progabide is described, e.g., in U.S. Pat. Nos. 4,094,992 and 4,361,583; the GAT1 inhibitor Tiagabine, which is described, e.g., in U.S. Pat. No. 5,010,090 and Andersen et al. *J. Med. Chem.* 1993, 36, 1716; the GABA transaminase inhibitor Valproic Acid (2-propylpentanoic acid or dispropylacetic acid), which is described, e.g., in U.S. Pat. No. 4,699,927 and Carraz et al., *Therapie,* 1965, 20, 419; the GABA transaminase inhibitor Vigabatrin, which is described, e.g., in U.S. Pat. No. 3,960,927; or Topiramate, which is described, e.g., in U.S. Pat. No. 4,513,006.

Additionally, the neurogenic agent in combination with a muscarinic agent, such as an inhibitor of AChE activity, may be a neurogenic sensitizing agent that is a reported antiepileptic agent. Non-limiting examples of such agents include carbamazepine or tegretol (CAS RN 298-46-4), clonazepam (CAS RN 1622-61-3), BPA or 3-(p-Boronophenyl)alanine (CAS RN 90580-64-6), gabapentin or neurontin (CAS RN 60142-96-3), phenytoin (CAS RN 57-41-0), topiramate, lamotrigine or lamictal (CAS RN 84057-84-1), phenobarbital (CAS RN 50-06-6), oxcarbazepine (CAS RN 28721-07-5), primidone (CAS RN 125-33-7), ethosuximide (CAS RN 77-67-8), levetiracetam (CAS RN 102767-28-2), zonisamide, tiagabine (CAS RN 115103-54-3), depakote or divalproex sodium (CAS RN 76584-70-8), Felbamate (Na-channel and NMDA receptor antagonist), or pregabalin (CAS RN 148553-50-8).

In further embodiments, the neurogenic sensitizing agent may be reported a direct or indirect modulator of dopamine receptors. Non-limiting examples of such agents include the indirect dopamine agonists methylphenidate (CAS RN 113-45-1) or Methylphenidate hydrochloride (also known as ritalin CAS RN 298-59-9), amphetamine (CAS RN 300-62-9) and methamphetamine (CAS RN 537-46-2), and the direct dopamine agonists sumanirole (CAS RN 179386-43-7), roprinirole (CAS RN 91374-21-9), and rotigotine (CAS RN 99755-59-6).

Additional non-limiting examples include bromocriptine (CAS RN 25614-03-3), adrogolide (CAS RN 171752-56-0), pramipexole (CAS RN 104632-26-0), Ropinirole (CAS RN 91374-21-9), apomorphine (CAS RN 58-00-4) or apomorphine hydrochloride (CAS RN 314-19-2), lisuride (CAS RN 18016-80-3), Sibenadet hydrochloride or Viozan (CAS RN 154189-24-9), L-DOPA or Levodopa (CAS RN 59-92-7), Melevodopa (CAS RN 7101-51-1), etilevodopa (CAS RN 37178-37-3), Talipexole hydrochloride (CAS RN 36085-73-1) or Talipexole (CAS RN 101626-70-4), Nolomirole (CAS RN 90060-42-7), quinelorane (CAS RN 97466-90-5), pergolide (CAS RN 66104-22-1), fenoldopam (CAS RN 67227-56-9), Carmoxirole (CAS RN 98323-83-2), terguride (CAS RN 37686-84-3), cabergoline (CAS RN 81409-90-7), quinagolide (CAS RN 87056-78-8) or quinagolide hydrochloride (CAS RN 94424-50-7), sumanirole, docarpamine (CAS RN 74639-40-0), SLV-308 or 2(3H)-Benzoxazolone, 7-(4-methyl-1-piperazinyl)-monohydrochloride (CAS RN 269718-83-4), aripiprazole (CAS RN 129722-12-9), bifeprunox, lisdexamfetamine dimesylate (CAS RN 608137-33-3), safinamide (CAS RN 133865-89-1), or Adderall or Amfetamine (CAS RN 300-62-9).

The combination of the muscarinic agent tacrine with ritalin resulted in at least additive activity (see Example 8 below). See Example 12 for a discussion of additive activity. Tacrine alone has an $EC_{50}$ of 8.0 μM for neuronal differentiation. Ritalin alone has an $EC_{50}$ of 3.5 μM. The concentration of each agent in combination to reach 50% activity in neuronal differentiation is 2.06 μM, resulting in a CI of 0.9976. As the CI is less than 1, the two compounds have at least an additive effect in neuronal differentiation. This indicates that the administered amounts of each compound can be lowered, with a concomitant reduction in side effects profile, while still providing greater efficacy than either compound alone.

In further embodiments, the neurogenic agent used in combination with a muscarinic agent, such as an inhibitor of AChE activity, may be a reported dual sodium and calcium channel modulator. Non-limiting examples of such agents include safinamide and zonisamide. Additional non-limiting examples include enecadin (CAS RN 259525-01-4), Levosemotiadil (CAS RN 116476-16-5), bisaramil (CAS RN 89194-77-4), SL-34.0829 (see U.S. Pat. No. 6,897,305), lifarizine (CAS RN 119514-66-8), JTV-519 (4-[3-(4-benzylpiperidin-1-yl)propionyl]-7-methoxy-2,3,4,5-tetrahydro-1,4-benzothiazepine monohydrochloride), and delapril.

In further embodiments, the neurogenic agent in used in combination with a muscarinic agent, such as an inhibitor of AChE activity, may be a reported calcium channel antagonists such as amlodipine (CAS RN 88150-42-9) or amlodipine maleate (CAS RN 88150-47-4), nifedipine (CAS RN 21829-25-4), MEM-1003 (CAS RN see Rose et al. "Efficacy of MEM 1003, a novel calcium channel blocker, in delay and trace eyeblink conditioning in older rabbits." Neurobiol Aging. 2006 Apr. 16; [Epub ahead of print]), isradipine (CAS RN 75695-93-1), felodipine (CAS RN 72509-76-3; 3,5-Pyridinedicarboxylic acid, 1,4-dihydro-4-(2,3-dichlorophenyl)-2,6-dimethyl-, ethyl methyl ester) or felodipine (CAS RN 86189-69-7; 3,5-Pyridinedicarboxylic acid, 4-(2,3-dichlorophenyl)-1,4-dihydro-2,6-dimethyl-, ethyl methyl ester, (+−)-), lemildipine (CAS RN 125729-29-5 or 94739-29-4), clevidipine (CAS RN 166432-28-6 or 167221-71-8), verapamil (CAS RN 52-53-9), ziconotide (CAS RN 107452-89-1), monatepil maleate (CAS RN 132046-06-1), manidipine (CAS RN 89226-50-6), Furnidipine (CAS RN 138661-03-7), Nitrendipine (CAS RN 39562-70-4), Loperamide (CAS RN 53179-11-6), Amiodarone (CAS RN 1951-25-3), Bepridil (CAS RN 64706-54-3), diltiazem (CAS RN 42399-41-7), Nimodipine (CAS RN 66085-59-4), Lamotrigine, Cinnarizine (CAS RN 298-57-7), lacipidine (CAS RN 103890-78-4), nilvadipine (CAS RN 75530-68-6), dotarizine (CAS RN 84625-59-2), cilnidipine (CAS RN 132203-70-4), Oxodipine (CAS RN 90729-41-2), aranidipine (CAS RN 86780-90-7), anipamil (CAS RN 83200-10-6), ipenoxazone (CAS RN 104454-71-9), Efonidipine hydrochloride or NZ 105 (CAS RN 111011-53-1) or Efonidipine (CAS RN 111011-63-3), temiverine (CAS RN 173324-94-2), pranidipine (CAS RN 99522-79-9), dopropidil (CAS RN 79700-61-1), lercanidipine (CAS RN 100427-26-7), terodiline (CAS RN 15793-40-5), fantofarone (CAS RN 114432-13-2), azelnidipine (CAS RN 123524-52-7), mibefradil (CAS RN 116644-53-2) or mibefradil dihydrochloride (CAS RN 116666-63-8), SB-237376 (see Xu et al. "Electrophysiologic effects of SB-237376: a new antiarrhythmic compound with dual potassium and calcium channel blocking action." J Cardiovasc Pharmacol. 2003 41(3):414-21), BRL-32872 (CAS RN 113241-47-7), S-2150 (see Ishibashi et al. "Pharmacodynamics of S-2150, a simultaneous calcium-blocking and alphal-inhibiting antihypertensive drug, in rats." J Pharm Pharmacol. 2000 52(3):273-80), nisoldipine (CAS RN 63675-72-9), semotiadil (CAS RN 116476-13-2), palonidipine (CAS RN 96515-73-0) or palonidipine hydrochloride (CAS RN 96515-74-1), SL-87.0495 (see U.S. Pat. No. 6,897,305), YM430 (4(((S)-2-hydroxy-3-phenoxypropyl)amino)butyl methyl 2,6-dimethyl-((S)-4-(m-nitrophenyl))-1,4-dihydropyridine-3,5-dicarboxylate), barnidipine (CAS RN 104713-75-9), and AM336 or CVID (see Adams et al. "Omega-Conotoxin CVID Inhibits a Pharmacologically Distinct Voltage-sensitive Calcium Channel Associated with Transmitter Release from Preganglionic Nerve Terminals" J. Biol. Chem., 278(6): 4057-4062, 2003). An additional non-limiting example is NMED-160.

In other embodiments, the neurogenic agent used in combination with a muscarinic agent, such as an inhibitor of AChE activity, may be a reported modulator of a melatonin receptor. Non-limiting examples of such modulators include the melatonin receptor agonists melatonin, LY-156735 (CAS RN 118702-11-7), agomelatine (CAS RN 138112-76-2), 6-chloromelatonin (CAS RN 63762-74-3), Ramelteon (CAS RN 196597-26-9), 2-Methyl-6,7-dichloromelatonin (CAS RN 104513-29-3), and ML 23 (CAS RN 108929-03-9).

In yet further embodiments, the neurogenic agent in combination with a muscarinic agent, such as an inhibitor of AChE activity, may be a reported modulator of a melanocortin receptor. Non-limiting examples of such agents include a melanocortin receptor agonists selected from melanotan II (CAS RN 121062-08-6), PT-141 or Bremelanotide (CAS RN 189691-06-3), HP-228 (see Getting et al. "The melanocortin peptide HP228 displays protective effects in acute models of inflammation and organ damage." Eur J Pharmacol. 2006 Jan. 24), or AP214 from Action Pharma A/S.

Additional examples of combinations of a muscarinic agent, such as an inhibitor of AChE activity, and another agent include the muscarinic agent, ibudilast, and captopril; the muscarinic agent, enoximone, and captopril; the muscarinic agent, enoximone, and serotonin; the muscarinic agent, rolipram, and serotonin; and the muscarinic agent, rolipram, and buspirone.

Thus a combination of neurogenic agents used with a muscarinic agent, such as an inhibitor of AChE activity, may be a reported modulator of angiotensin II function, such as at an angiotensin II receptor. In some embodiments, the neurogenic sensitizing agent used with a muscarinic agent may be a reported inhibitor of an angiotensin converting enzyme (ACE). Non-limiting examples of such reported inhibitors include a sulfhydryl-containing (or mercapto-containing) agent, such as Alacepril, captopril (Capoten®), fentiapril, pivopril, pivalopril, or zofenopril; a dicarboxylate-containing agent, such as enalapril (Vasotec® or Renitec®) or enalaprilat, ramipril (Altace® or Tritace® or Ramace®), quinapril (Accupril®) or quinapril hydrochloride, perindopril (Coversyl®) or perindopril erbumine (Aceon®), lisinopril (Lisodur® or Prinivil® or Zestril®); a phosphonate-containing (or phosphate-containing) agent, such as fosinopril (Monopril®), fosinoprilat, fosinopril sodium (CAS RN 88889-14-9), benazepril (Lotensin®) or benazepril hydrochloride, imidapril or imidapril hydrochloride, moexipril (Univasc®), or trandolapril (Mavik®). In other embodiments, a modulator is administered in the form of an ester that increases bioavailability upon oral administration with subsequent conversion into metabolites with greater activity.

Further embodiments include reported angiotensin II modulating entities that are naturally occurring, such as casokinins and lactokinins (breakdown products of casein and whey) which may be administered as such to obviate the need for their formation during digestion. Additional non-limiting embodiments of reported angiotensin receptor antagonists include candesartan (Atacand® or Ratacand®, 139481-59-7) or candesartan cilexetil; eprosartan (Teveten®) or eprosartan mesylate; irbesartan (Aprovel® or Karvea® or Avapro®); losartan (Cozaar® or Hyzaar®); olmesartan (Benicar®, CAS RN 144689-24-7) or olmesartan medoxomil (CAS RN 144689-63-4); telmisartan (Micardis® or Pritor®); or valsartan (Diovan®).

Additional non-limiting examples of a reported angiotensin modulator that may be used in a combination include nateglinide or starlix (CAS RN 105816-04-4); tasosartan or its metabolite enoltasosartan; omapatrilat (CAS RN 167305-00-2); or a a combination of nateglinide and valsartan, amoldipine and benazepril (Lotrel 10-40 or Lotrel 5-40), or delapril and manidipine (CHF 1521).

The combination of the muscarinic agent donepezil with captopril resulted in synergistic activity (see Example 8 below). Donepezil alone has an $EC_{50}$ of 2.02 µM for neuronal differentiation. Captopril alone has an $EC_{50}$ of 3.78 µM. The concentration of each agent in combination to reach 50% activity in neuronal differentiation is 0.3 µM, resulting in a CI of 0.24. As the CI is less than 1, the two compounds have a synergistic effect in neuronal differentiation.

Additionally, the agent used with a muscarinic agent, such as an inhibitor of AChE activity, may be a reported 5HT1a receptor agonist (or partial agonist) such as buspirone (buspar). In some embodiments, a reported 5HT1a receptor agonist is an azapirone, such as, but not limited to, tandospirone, gepirone and ipsapirone. Non-limiting examples of additional reported 5HT1a receptor agonists include flesinoxan, MDL 72832 hydrochloride, U-92016A, (+)-UH 301, F 13714, F 13640, 6-hydroxy-buspirone (see US 2005/0137206), S-6-hydroxy-buspirone (see US 2003/0022899), R-6-hydroxy-buspirone (see US 2003/0009851), adatanserin, and buspirone-saccharide (see WO 00/12067). As indicated in Example 8 below, the combination of the muscarinic agent tacrine with buspirone resulted in synergistic activity.

Additional non-limiting examples of reported 5HT1a receptor agonists include OPC-14523 (1-[3-[4-(3-chlorophenyl)-1-piperazinyl]propyl]-5-methoxy-3,4-dihydro-2[1H]-quinolinone monomethanesulfonate); BMS-181100 or BMY 14802 (CAS RN 105565-56-8); flibanserin (CAS RN 167933-07-5); repinotan (CAS RN 144980-29-0); lesopitron (CAS RN 132449-46-8); piclozotan (CAS RN 182415-09-4); Aripiprazole, Org-13011 (1-(4-trifluoromethyl-2-pyridinyl)-4-[4-[2-oxo-1-pyrrolidinyl]butyl]piperazine (E)-2-butenedioate); SDZ-MAR-327 (see Christian et al. "Positron emission tomographic analysis of central dopamine D1 receptor binding in normal subjects treated with the atypical neuroleptic, SDZ MAR 327." Int J Mol Med. 1998 1(1):243-7); MKC-242 ((S)-5-[3-[(1,4-benzodioxan-2-ylmethyl)amino]propoxy]-1,3-benzodioxole HCl); vilazodone; sarizotan (CAS RN 177975-08-5); roxindole (CAS RN 112192-04-8) or roxindole methanesulfonate (CAS RN 119742-13-1); alnespirone (CAS RN 138298-79-0); bromerguride (CAS RN 83455-48-5); xaliproden (CAS RN 135354-02-8); mazapertine succinate (CAS RN 134208-18-7) or mazapertine (CAS RN 134208-17-6); PRX-00023; F-13640 ((3-chloro-4-fluoro-phenyl)-[4-fluoro-4-[[(5-methyl-pyridin-2-ylmethyl)-amino]methyl]piperidin-1-yl]methanone, fumaric acid salt); eptapirone (CAS RN 179756-85-5); Ziprasidone (CAS RN 146939-27-7); Sunepitron (see Becker et al. "G protein-coupled receptors: In silico drug discovery in 3D" PNAS 2004 101(31):11304-11309); umespirone (CAS RN 107736-98-1); SLV-308; bifeprunox; flesinoxan (CAS RN 98206-10-1); and zalospirone (CAS RN 114298-18-9).

Yet further non-limiting examples include AP-521 (partial agonist from AsahiKasei) and Du-123015 (from Solvay).

Alternatively, the agent used with a muscarinic agent, such as an inhibitor of AChE activity, may be a reported 5HT4 receptor agonist (or partial agonist). In some embodiments, a reported 5HT4 receptor agonist or partial agonist is a substituted benzamide, such as cisapride; individual, or a combination of, cisapride enantiomers ((+) cisapride and (−) cisapride); mosapride; and renzapride as non-limiting examples. In other embodiments, the chemical entity is a benzofuran derivative, such as prucalopride. Additional embodiments include indoles, such as tegaserod, or benzimidazolones. Other non-limiting chemical entities reported as a 5HT4 receptor agonist or partial agonist include zacopride (CAS RN 90182-92-6), SC-53116 (CAS RN 141196-99-8) and its racemate SC-49518 (CAS RN 146388-57-0), BIMU1 (CAS RN 127595-43-1), TS-951 (CAS RN 174486-39-6), or ML10302 CAS RN 148868-55-7). Additional non-limiting chemical entities include metoclopramide, 5-methoxytryptamine, RS67506, 2-[1-(4-piperonyl)piperazinyl]benzothiazole, RS66331, BIMU8, SB 205149 (the n-butyl quaternary analog of renzapride), or an indole carbazimidamide as described by Buchheit et al. ("The serotonin 5-HT4 receptor. 2. Structure-activity studies of the indole carbazimidamide class of agonists." *J Med Chem.* (1995) 38(13):2331-8). Yet additional non-limiting examples include norcisapride (CAS RN 102671-04-5) which is the metabolite of cisapride; mosapride citrate; the maleate form of tegaserod (CAS RN 189188-57-6); zacopride hydrochloride (CAS RN 99617-34-2); mezacopride (CAS RN 89613-77-4); SK-951 ((+−)-4-amino-N-(2-(1-azabicyclo(3.3.0)octan-5-yl)ethyl)-5-chloro-2,3-dihydro-2-methylbenzo(b)furan-7-carboxamide hemifumarate); ATI-7505, a cisapride analog from ARYx Therapeutics; SDZ-216-454, a selective 5HT4 receptor agonist that stimulates cAMP formation in a concentration dependent manner (see Markstein et al. "Pharmacological characterisation of 5-HT receptors positively coupled to adenylyl cyclase in the rat hippocampus." *Naunyn Schmiedebergs Arch Pharmacol.* (1999) 359(6):454-9); SC-54750, or Aminomethylazaadamantane; Y-36912, or 4-amino-N-[1-[3-(benzylsulfonyl)propyl]piperidin-4-ylmethyl]-5-chloro-2-methoxybenzamide as disclosed by Sonda et al. ("Synthesis and pharmacological properties of benzamide derivatives as selective serotonin 4 receptor agonists." *Bioorg Med Chem.* (2004) 12(10):2737-47); TKS159, or 4-amino-5-chloro-2- methoxy-N-[(2S,4S)-1-ethyl-2-hydroxymethyl-4-pyrrolidinyl]benzamide, as reported by Haga et al. ("Effect of TKS 159, a novel 5-hydroxytryptamine4 agonist, on gastric contractile activity in conscious dogs."; RS67333, or 1-(4-amino-5-chloro-2-methoxyphenyl)-3-(1-n-butyl-4-piperidinyl)-1-propanone; KDR-5169, or 4-amino-5-chloro-N-[1-(3-fluoro-4-methoxybenzyl)piperidin-4-yl]-2-(2-hydroxyethoxy)benzamide hydrochloride dihydrate as reported by Tazawa, et al. (2002) "KDR-5169, a new gastrointestinal prokinetic agent, enhances gastric contractile and emptying activities in dogs and rats." Eur J Pharmacol 434(3):169-76); SL65.0155, or 5-(8-amino-7-chloro-2,3-dihydro-1,4-benzodioxin-5-yl)-3-[1-(2-phenyl ethyl)-4-piperidinyl]-1,3,4-oxadiazol-2(3H)-one monohydrochloride; and Y-34959, or 4-Amino-5-chloro-2-methoxy-N-[1-[5-(1-methylindol-3-ylcarbonylamino)pentyl]piperidin-4-ylmethyl]benzamide.

Other non-limiting reported 5HT4 receptor agonists and partial agonists for use in combination with a muscarinic agent, such as an inhibitor of AChE activity, include metoclopramide (CAS RN 364-62-5), 5-methoxytryptamine (CAS RN 608-07-1), RS67506 (CAS RN 168986-61-6), 2-[1-(4-piperonyl)piperazinyl]benzothiazole (CAS RN 155106-73-3), RS66331 (see Buccafusco et al. "Multiple Central Nervous System Targets for Eliciting Beneficial Effects on Memory and Cognition." (2000) Pharmacology 295(2):438-446), BIMU8 (endo-N-8-methyl-8-azabicyclo[3.2.1]oct-3-yl)-2,3-dehydro-2-oxo-3-(prop-2-yl)-1H-benzimid-azole-1-carboxamide), or SB 205149 (the n-butyl quaternary analog of renzapride). Compounds related to metoclopramide, such as metoclopramide dihydrochloride (CAS RN 2576-84-3) or metoclopramide dihydrochloride (CAS RN 5581-45-3) or metoclopramide hydrochloride (CAS RN 7232-21-5 or 54143-57-6) may also be used in a combination or method as described herein.

Additionally, the agent used with a muscarinic agent, such as an inhibitor of AChE activity, may be a reported 5HT3 receptor antagonist such as azasetron (CAS RN 123039-99-6); Ondansetron (CAS RN 99614-02-5) or Ondansetron hydrochloride (CAS RN 99614-01-4); Cilansetron (CAS RN 120635-74-7); Aloxi or Palonosetron Hydrochloride (CAS RN 135729-62-3); Palenosetron (CAS RN 135729-61-2 or 135729-56-5); Cisplatin (CAS RN 15663-27-1); Lotronex or Alosetron hydrochloride (CAS RN 122852-69-1); Anzemet or Dolasetron mesylate (CAS RN 115956-13-3); zacopride or R-Zacopride; E-3620 ([3(S)-endo]-4-amino-5-chloro-N-(8-methyl-8-azabicyclo[3.2.1-]oct-3-yl-2[(1-methyl-2-butynyl)oxy]benzamide) or E-3620 HCl (3(S)-endo-4-amino-5-chloro-N-(8-methyl-8-azabicyclo[3.2.1]oct-3-yl)-2-(1-methyl-2-butinyl)oxy)-benzamide-HCl); YM 060 or Ramosetron hydrochloride (CAS RN 132907-72-3); a thieno[2,3-d]pyrimidine derivative antagonist described in U.S. Pat. No. 6,846,823, such as DDP 225 or MCI 225 (CAS RN 135991-48-9); Marinol or Dronabinol (CAS RN 1972-08-3); or Lac Hydrin or Ammonium lactate (CAS RN 515-98-0); Kytril or Granisetron hydrochloride (CAS RN 107007-99-8); Bemesetron (CAS RN 40796-97-2); Tropisetron (CAS RN 89565-68-4); Zatosetron (CAS RN 123482-22-4); Mirisetron (CAS RN 135905-89-4) or Mirisetron maleate (CAS RN 148611-75-0); or renzapride (CAS RN 112727-80-7).

Additionally, the agent used with a muscarinic agent, such as an inhibitor of AChE activity, may be a reported 5HT2A/2C receptor antagonist such as Ketanserin (CAS RN 74050-98-9) or ketanserin tartrate; risperidone; olanzapine; adatanserin (CAS RN 127266-56-2); Ritanserin (CAS RN 87051-43-2); Deramciclane (CAS RN 120444-71-5); Geoden or Ziprasidone hydrochloride (CAS RN 138982-67-9); Zeldox or Ziprasidone or Ziprasidone hydrochloride; EMD 281014 (7-[4-[2-(4-fluoro-phenyl)-ethyl]-piperazine-1-carbonyl]-1H-indole-3-carbonitrile HCl); MDL 100907 or M100907 (CAS RN 139290-65-6); Effexor XR (Venlafaxine formulation); Zomaril or Iloperidone; quetiapine (CAS RN 111974-69-7) or Quetiapine fumarate (CAS RN 111974-72-2) or Seroquel; SB 228357 or SB 243213 (see Bromidge et al. "Biarylcarbamoylindolines are novel and selective 5-HT(2C) receptor inverse agonists: identification of 5-methyl-1-[[2-[(2-methyl-3-pyridyl)oxy]-5-pyridyl]carbamoyl]-6-trifluoromethylindoline (SB-243213) as a potential antidepressant/anxiolytic agent." J Med Chem. 2000 43(6):1123-34; SB 220453 or Tonabersat (CAS RN 175013-84-0); Sertindole (CAS RN 106516-24-9); Eplivanserin (CAS RN 130579-75-8) or Eplivanserin fumarate (CAS RN 130580-02-8); Lubazodone hydrochloride (CAS RN 161178-10-5); Cyproheptadine (CAS RN 129-03-3); Pizotyline or pizotifen (CAS RN 15574-96-6); Mesulergine (CAS RN 64795-35-3); Irindalone (CAS RN 96478-43-2); MDL 11939 (CAS RN 107703-78-6); or pruvanserin (CAS RN 443144-26-1).

Additional non-limiting examples of modulators include reported 5-HT2A receptor inverse agonists, such as ACP 103 (CAS RN: 868855-07-6), APD125 (from Arena Pharmaceuticals), AVE 8488 (from Sanofi-Aventis) or TGWOOAD/AA (from Fabre Kramer Pharmaceuticals).

Additionally, the agent used with a muscarinic agent, such as an inhibitor of AChE activity, may be a reported 5HT6 receptor antagonist such as SB-357134 (N-(2,5-Dibromo-3-fluorophenyl)-4-methoxy-3-piperazin-1-ylbenzenesulfonamide); SB-271046 (5-chloro-N-(4-methoxy-3-(piperazin-1-yl)phenyl)-3-methylbenzo[b]thiophene-2-sulfonamide); Ro 04-06790 (N-(2,6-bis(methylamino)pyrimidin-4-yl)-4-aminobenzenesulfonamide); Ro 63-0563 (4-amino-N-(2,6 bis-methylamino-pyridin-4-yl)-benzene sulfonamide); clozapine or its metabolite N-desmethylclozapine; olanzapine (CAS RN 132539-06-1); fluperlapine (CAS RN 67121-76-0); seroquel (quetiapine or quetiapine fumarate); clomipramine (CAS RN 303-49-1); amitriptyline (CAS RN50-48-6); doxepin (CAS RN 1668-19-5); nortryptyline (CAS RN 72-69-5); 5-methoxytryptamine (CAS RN 608-07-1); bromocryptine (CAS RN 25614-03-3); octoclothepin (CAS RN 13448-22-1); chlorpromazine (CAS RN 50-53-3); loxapine (CAS RN 1977-10-2); fluphenazine (CAS RN 69-23-8); or GSK 742457 (presented by David Witty, "Early Optimisation of in vivo Activity: the discovery of 5-HT6 Receptor Antagonist 742457" GlaxoSmithKline at SCIpharm 2006, International Pharmaceutical Industry Conference in Edinburgh, 16 May 2006).

As an additional non-limiting example, the reported 5HT6 modulator may be SB-258585 (4-Iodo-N-[4-methoxy-3-(4-methyl-piperazin-1-yl)-phenyl]-benzenesulphonamide); PRX 07034 (from Predix Pharmaceuticals) or a partial agonist, such as E-6801 (6-chloro-N-(3-(2-(dimethylamino)ethyl)-1H-indol-5-yl)imidazo[2,1-b]thiazole-5-sulfonamide) or E-6837 (5-chloro-N-(3-(2-(dimethylamino)ethyl)-1H-indol-5-yl)naphthalene-2-sulfonamide).

Additionally, the agent used with a muscarinic agent, such as an inhibitor of AChE activity, may be a reported trace amine (TA), or a metabolite, precursor, prodrug, or analogue thereof, receptor modulator. TAs are endogenous, CNS-active amines that are structurally related to classical biogenic amines (e.g., dopamine, 5-HT, norepinephrine). The methods of the disclosure thus include administration of one or more reported TAs in a combination.

Certain food products, e.g., chocolates, cheeses, and wines, can also provide a significant dietary source of TAs and/or TA-related compounds. Non-limiting examples of mammalian TAs useful as constitutive factors include, but are not limited to, tryptamine, ρ-tyramine, m-tyramine, octopamine, synephrine and β-phenylethylamine (β-PEA). Additional useful TA-related compounds include, but are not limited to, 5-hydroxytryptamine, amphetamine, bufotenin, 5-methoxytryptamine, dihydromethoxytryptamine, and phenylephrine.

In some embodiments, the constitutive factor is a biogenic amine or a ligand of a trace amine-associated receptor (TAAR), and/or an agent that mediates one or more biological effects of a TA. TAs have been shown to bind to and activate a number of unique receptors, termed TAARs, which comprise a family of G-protein coupled receptors (TAAR1-TAAR9) with homology to classical biogenic amine receptors. For example, TAAR1 is activated by both tyramine and β-PEA.

Thus non-limiting embodiments include methods and combination compositions wherein the constitutive factor is β-PEA, which has been indicated as having a significant neuromodulatory role in the mammalian CNS and is found at relatively high levels in the hippocampus (e.g., Taga et al., Biomed Chromatogr., 3(3): 118-20 (1989)); a metabolite, prodrug, precursor, or other analogue of β-PEA, such as the β-PEA precursor L-phenylalanine, the β-PEA metabolite β-phenylacetic acid (β-PAA), or the β-PEA analogues methylphenidate, amphetamine, and related compounds.

Most TAs have a short half-life (e.g., less than about 30 s) due, e.g., to their rapid extracellular metabolism by MAO-A and/or MAO-B, which provide the major pathway for TA metabolism. Thus, in some embodiments, TA levels are regulated by modulating the activity of MAO-A and/or MAO-B. For example, in some embodiments, endogenous TA levels are increased (and TA signaling is enhanced) by administering an inhibitor of MAO-A and/or MAO-B, in combination with a muscarinic agent, such as an inhibitor of AChE activity, as described herein. Non-limiting examples of inhibitors of monoamine oxidase (MAO) include reported inhibitors of the MAO-A isoform, which preferentially deaminates 5-hydroxytryptamine (serotonin) (5-HT) and norepinephrine (NE), and/or the MAO-B isoform, which preferentially deaminates phenylethylamine (PEA) and benzylamine (both MAO-A and MAO-B metabolize Dopamine (DA)). In various embodiments, MAO inhibitors may be irreversible or reversible (e.g., reversible inhibitors of MAO-A (RIMA)), and may have varying potencies against MAO-A and/or MAO-B (e.g., non-selective dual inhibitors or isoform-selective inhibitors). Non-limiting examples of MAO inhibitors useful in methods described herein include clorgyline, L-deprenyl, isocarboxazid (Marplan), ayahuasca, nialamide, iproniazide, iproclozide, moclobemide (Aurorix), phenelzine (Nardil), tranylcypromine (Pamate) (the congeneric of phenelzine), toloxatone, levo-deprenyl (Selegiline), harmala, RIMAs (e.g., moclobemide, described in Da Prada et al., J Pharmacol Exp Ther 248: 400-414 (1989); brofaromine; and befloxatone, described in Curet et al., J Affect Disord 51: 287-303 (1998)), lazabemide (Ro 19 6327), described in Ann. Neurol., 40(1): 99-107 (1996), and SL25.1131, described in Aubin et al., J. Pharmacol. Exp. Ther., 310: 1171-1182 (2004).

In embodiments relating to a biogenic amine modulator used in a combination or method with a muscarinic agent as disclosed herein, the modulator may be (i) a norepinephrine and dopamine reuptake inhibitor, such as bupropion (described, e.g., in U.S. Pat. Nos. 3,819,706 and 3,885,046), or (S,S)-hydroxybupropion (described, e.g., in U.S. Pat. No. 6,342,496); (ii) selective dopamine reuptake inhibitors, such as medifoxamine, amineptine (described, e.g., in U.S. Pat. Nos. 3,758,528 and 3,821,249), GBR12909, GBR12783 and GBR13069, described in Andersen, Eur J Pharmacol, 166: 493-504 (1989); or (iii) a biogenic amine "releaser" which stimulates the release of biogenic amines, such as fenfluramine or p-chloroamphetamine (PCA), or the dopamine, norepinephrine, and serotonin releasing compound amineptine (described, e.g., in U.S. Pat. Nos. 3,758,528 and 3,821,249).

The agent used with a muscarinic agent, such as an inhibitor of AChE activity, may be a reported phosphodiesterase (PDE) inhibitor. In some embodiments, a reported inhibitor of PDE activity include an inhibitor of a cAMP-specific PDE. Non-limiting examples of cAMP specific PDE inhibitors useful in the methods described herein include a pyrrolidinone, such as a compound disclosed in U.S. Pat. No. 5,665,754, US20040152754 or US20040023945; a quinazolineone, such as a compound disclosed in U.S. Pat. Nos. 6,747,035 or 6,828,315, WO 97/49702 or WO 97/42174; a xanthine derivative; a phenylpyridine, such as a compound disclosed in U.S. Pat. No. 6,410,547 or 6,090,817, or WO 97/22585; a diazepine derivative, such as a compound disclosed in WO 97/36905; an oxime derivative, such as a compound disclosed in U.S. Pat. No. 5,693,659 or WO 96/00215; a naphthyridine, such as a compound described in U.S. Pat. Nos. 5,817,670, 6,740,662, 6,136,821, 6,331,548, 6,297,248, 6,541,480, 6,642,250, or 6,900,205, or Trifilieff et al., *Pharmacology*, 301(1): 241-248 (2002), or Hersperger et al., *J Med Chem.*, 43(4):675-82 (2000); a benzofuran, such as a compound disclosed in U.S. Pat. Nos. 5,902,824, 6,211,203, 6,514,996, 6,716,987, 6,376,535, 6,080,782, or 6,054,475, or EP 819688, EP685479, or Perrier et al., *Bioorg. Med. Chem. Lett.* 9:323-326 (1999); a phenanthridine, such as that disclosed in U.S. Pat. Nos. 6,191,138, 6,121,279, or 6,127,378; a benzoxazole, such as that disclosed in U.S. Pat. Nos. 6,166,041 or 6,376,485; a purine derivative, such as a compound disclosed in U.S. Pat. No. 6,228,859; a benzamide, such as a compound described in U.S. Pat. No. 5,981,527 or 5,712,298, or W095/01338, WO 97/48697 or Ashton et al., *J. Med Chem* 37: 1696-1703 (1994); a substituted phenyl compound, such as a compound disclosed in U.S. Pat. Nos. 6,297,264, 5,866,593, 5,859,034, 6,245,774, 6,197,792, 6,080,790, 6,077,854, 5,962,483, 5,674,880, 5,786,354, 5,739,144, 5,776,958, 5,798,373, 5,891,896, 5,849,770, 5,550,137, 5,340,827, 5,780,478, 5,780,477, or 5,633,257, or WO 95/35283; a substituted biphenyl compound, such as that disclosed in U.S. Pat. No. 5,877,190; or a quinilinone, such as a compound described in U.S. Pat. No. 6,800,625 or WO 98/14432.

Additional non-limiting examples of reported cAMP-specific PDE inhibitors useful in methods disclosed herein include a compound disclosed in U.S. Pat. Nos. 6,818,651, 6,737,436, 6,613,778, 6,617,357, 6,146,876, 6,838,559, 6,884,800, 6,716,987, 6,514,996, 6,376,535, 6,740,655, 6,559,168, 6,069,151, 6,365,585, 6,313,116, 6,245,774, 6,011,037, 6,127,363, 6,303,789, 6,316,472, 6,348,602, 6,331,543, 6,333,354, 5,491,147, 5,608,070, 5,622,977, 5,580,888, 6,680,336, 6,569,890, 6,569,885, 6,500,856, 6,486,186, 6,458,787, 6,455,562, 6,444,671, 6,423,710, 6,376,489, 6,372,777, 6,362,213, 6,313,156, 6,294,561, 6,258,843, 6,258,833, 6,121,279, 6,043,263, RE 38,624, 6,297,257, 6,251,923, 6,613,794, 6,407,108, 6,107,295, 6,103,718, 6,479,494, 6,602,890, 6,545,158, 6,545,025, 6,498,160, 6,743,802, 6,787,554, 6,828,333, 6,869,945, 6,894,041, 6,924,292, 6,949,573, 6,953,810, 6,156,753, 5,972,927, 5,962,492, 5,814,651, 5,723,460, 5,716,967, 5,686,434, 5,502,072, 5,116,837, 5,091,431; 4,670,434; 4,490,371; 5,710,160, 5,710,170, 6,384,236, or 3,941,785, or US20050119225, US20050026913, US20050059686, US20040138279, US20050222138, US20040214843, US20040106631, US 20030045557, US 20020198198, US20030162802, US20030092908, US 20030104974, US20030100571, 20030092721, US20050148604, WO 99/65880, WO 00/26201, WO 98/06704, WO 00/59890, WO9907704, WO9422852, WO 98/20007, WO 02/096423, WO 98/18796, WO 98/02440, WO 02/096463, WO 97/44337, WO 97/44036, WO 97/44322, EP 0763534, Aoki et al., *J Pharmacol Exp Ther.*, 295(1):255-60 (2000), Del Piaz et al., *Eur. J. Med. Chem.*, 35; 463-480 (2000), or Barnette et al., *Pharmacol. Rev. Commun.* 8: 65-73 (1997).

In some embodiments, the reported cAMP-specific PDE inhibitor is Cilomilast (SB-207499); Filaminast; Tibenelast (LY-186655); Ibudilast; Piclamilast (RP 73401);

Doxofylline; Cipamfylline (HEP-688); atizoram (CP-80633); theophylline; isobutylmethylxanthine; Mesopram (ZK-117137); Zardaverine; vinpocetine; Rolipram (ZK-62711); Arofylline (LAS-31025); roflumilast (BY-217); Pumafentrin (BY-343);

Denbufylline; EHNA; milrinone; Siguazodan; Zaprinast; Tolafentrine; Isbufylline; IBMX;

1C-485; diphylline; verolylline; bamifylline; pentoxyfilline; enprofilline; lirimilast (BAY 19-8004); filaminast (WAY-PDA-641); benafentrine; trequinsin; nitroquazone; cilostamide; vesnarinone; piroximone; enoximone; amrinone; olprinone; imazodan or 5-methyl-imazodan; indolidan; anagrelide; carbazeran; ampizone; emoradan; motapizone; phthalazinol; lixazinone (RS 82856); quazinone; bemorandan (RWJ 22867); adibendan (BM 14,478); Pimobendan (MCI-154); Saterinone (BDF 8634); Tetomilast (OPC-6535); benzafentrine; sulmazole (ARL 115); Revizinone; 349-U-85; AH-21-132; ATZ-1993; AWD-12-343; AWD-12-281; AWD-12-232; BRL 50481; CC-7085; CDC-801; CDC-998; CDP-840; CH-422; CH-673; CH-928; CH-3697; CH-3442; CH-2874; CH-4139; Chiroscience 245412; CI-930; CI-1018; CI-1044; Cl-1118; CP-353164; CP-77059; CP-146523; CP-293321; CP-220629; CT-2450; CT-2820; CT-3883; CT-5210; D-4418; D-22888; E-4021; EMD 54622; EMD-53998; EMD-57033; GF-248; GW-3600; IC-485; ICI 63197; ICI 153,110; IPL-4088; KF-19514; KW-4490; L-787258; L-826141; L-791943; LY181512; NCS-613; NM-702; NSP-153; NSP-306; NSP-307; Org-30029; Org-20241; Org-9731; ORG 9935; PD-168787; PD-190749; PD-190036; PDB-093; PLX650; PLX369; PLX371; PLX788; PLX939; Ro-20-1724; RPR-132294; RPR-117658A; RPR-114597; RPR-122818; RPR-132703; RS-17597; RS-25344; RS-14203; SCA 40; Sch-351591; SDZ-ISQ-844; SDZ-MKS-492; SKF 94120; SKF-95654; SKF-107806; SKF 96231; T-440; T-2585; WAY-126120; WAY-122331; WAY-127093B; WIN-63291; WIN-62582; V-11294A; VMX 554; VMX 565; XT-044; XT-611; Y-590; YM-58897; YM-976; ZK-62711; methyl 3-[6-(2H-3,4,5,6-tetrahydropyran-2-yloxy)-2-(3-thienylcarbonyl)benzo[b]furan-3-yl]propanoate; 4-[4-methoxy-3-(5-phenylpentyloxy)phenyl]-2-methylbenzoic acid; methyl 3-{2-[(4-chlorophenyl)carbonyl]-6-hydroxybenzo[b]furan-3-yl}propanoate; (R*,R*)-(±)-methyl 3-acetyl-4-[3-(cyclopentyloxy)-4-methoxyphenyl]-3-methyl-1-pyrrolidinecarboxylat; or 4-(3-bromophenyl)-1-ethyl-7-methylhydropyridino[2,3-b]pyridin-2-one.

In some embodiments, the reported PDE inhibitor inhibits a cGMP-specific PDE. Non-limiting examples of a cGMP specific PDE inhibitor for use in the combinations and methods described herein include a pyrimidine or pyrimidinone derivative, such as a compound described in U.S. Pat. Nos. 6,677,335, 6,458,951, 6,251,904, 6,787,548, 5,294,612, 5,250,534, or 6,469,012, WO 94/28902, WO 96/16657, EP0702555, and Eddahibi, *Br. J. Pharmacol.*, 125(4): 681-688 (1988); a griseolic acid derivative, such as a compound disclosed in U.S. Pat. No. 4,460,765; a 1-arylnaphthalene lignan, such as that described in Ukita, *J. Med. Chem.* 42(7): 1293-1305 (1999); a quinazoline derivative, such as 4-[[3',4'-(methylenedioxy)benzyl]amino]-6-methoxyquinazoline) or a compound described in U.S. Pat. Nos. 3,932,407 or 4,146,718, or RE 31,617; a pyrroloquinolone or pyrrolopyridinone, such as that described in U.S. Pat. Nos. 6,686,349, 6,635,638, 6,818,646, US20050113402; a carboline derivative, such a compound described in U.S. Pat. Nos. 6,492,358, 6,462,047, 6,821,975, 6,306,870, 6,117,881, 6,043,252, or 3,819,631, US20030166641, WO 97/43287, Daugan et al., *J Med Chem.*, 46(21):4533-42 (2003), or Daugan et al., *J Med Chem.*, 9;46 (21):4525-32 (2003); an imidazo derivative, such as a compound disclosed in U.S. Pat. Nos. 6,130,333, 6,566,360, 6,362,178, or 6,582,351, US20050070541, or US20040067945; or a compound described in U.S. Pat. Nos. 6,825,197, 5,719,283, 6,943,166, 5,981,527, 6,576,644, 5,859,009, 6,943,253, 6,864,253, 5,869,516, 5,488,055, 6,140,329, 5,859,006, or 6,143,777, WO 96/16644, WO 01/19802, WO 96/26940, Dunn, *Org. Proc. Res. Dev.*, 9: 88-97 (2005), or Bi et al., *Bioorg Med Chem Lett.*, 11 (18): 2461-4 (2001).

In some embodiments, the PDE inhibitor used in a combination or method disclosed herein is caffeine. In some embodiments, the caffeine is administered in a formulation comprising a muscarinic agent, such as an inhibitor of AChE activity. In other embodiments, the caffeine is administered simultaneously with the muscarinic agent. In alternative embodiments, the caffeine is administered in a formulation, dosage, or concentration lower or higher than that of a caffeinated beverage such as coffee, tea, or soft drinks. In further embodiments, the caffeine is administered by a non-oral means, including, but not limited to, parenteral (e.g., intravenous, intradermal, subcutaneous, inhalation), transdermal (topical), transmucosal, rectal, or intranasal (including, but not limited to, inhalation of aerosol suspensions for delivery of compositions to the nasal mucosa, trachea and bronchioli) administration. The disclosure includes embodiments with the explicit exclusion of caffeine or another one or more of the described agents for use in combination with a muscarinic agent.

In further alternative embodiments, the caffeine is in an isolated form, such as that which is separated from one or more molecules or macromolecules normally found with caffeine before use in a combination or method as disclosed herein. In other embodiments, the caffeine is completely or partially purified from one or more molecules or macromolecules normally found with the caffeine. Exemplary cases of molecules or macromolecules found with caffeine include a plant or plant part, an animal or animal part, and a food or beverage product.

Non-limiting examples of a reported PDE1 inhibitor include IBMX; vinpocetine; MMPX; KS-505a; SCH-51866; W-7; PLX650; PLX371; PLX788; a phenothiazines; or a compound described in U.S. Pat. No. 4,861,891.

Non-limiting examples of a PDE2 inhibitor include EHNA; PLX650; PLX369; PLX788; PLX 939; Bay 60-7550 or a related compound described in Boess et al., *Neuropharmacology*, 47(7):1081-92 (2004); or a compound described in US20020132754.

Non-limiting examples of reported PDE3 inhibitors include a dihydroquinolinone compound such as cilostamide, cilostazol, vesnarinone, or OPC 3911; an imidazolone such as piroximone or enoximone; a bipyridine such as milrinone, amrinone or olprinone; an imidazoline such as imazodan or 5-methyl-imazodan; a pyridazinone such as indolidan; LY 181512 (see Komas et al. "Differential sensitivity to cardiotonic drugs of cyclic AMP phosphodiesterases isolated from canine ventricular and sinoatrial-enriched tissues." *J Cardiovasc Pharmacol.* 1989 14(2):213-20); ibudilast; isomazole; motapizone; phthalazinol; trequinsin; lixazinone (RS 82856); Y-590; SKF 94120; quazinone; ICI 153,110; bemorandan (RWJ 22867); siguazodan (SK&F 94836); adibendan (BM 14,478); Pimobendan (UD-CG 115, MCI-I 54); Saterinone (BDF 8634); NSP-153; zardaverine; a quinazoline; benzafentrine; sulmazole (ARL 115); ORG 9935; CI-930; SKF-95654; SDZ-MKS-492; 349-U-85; EMD-53998; EMD-57033; NSP-306; NSP-307; Revizinone; NM-702; WIN-62582; ATZ-1993; WIN-63291; ZK-62711; PLX650; PLX369; PLX788; PLX939; anagrelide; carbazeran; ampizone; emoradan; or a compound disclosed in U.S. Pat. No. 6,156,753.

Non-limiting examples of reported PDE4 inhibitors include a pyrrolidinone, such as a compound disclosed in U.S. Pat. No. 5,665,754, US20040152754 or US20040023945; a quinazolineone, such as a compound disclosed in U.S. Pat. Nos. 6,747,035 or 6,828,315, WO 97/49702 or WO 97/42174; a xanthine derivative; a phenylpyridine, such as a compound disclosed in U.S. Pat. No. 6,410,547 or 6,090,817 or WO 97/22585; a diazepine derivative, such as a compound disclosed in WO 97/36905; an oxime derivative, such as a compound disclosed in U.S. Pat. No. 5,693,659 or WO 96/00215; a naphthyridine, such as a compound described in U.S. Pat. Nos. 5,817,670, 6,740,662, 6,136,821, 6,331,548, 6,297,248, 6,541,480, 6,642,250, or 6,900,205, Trifilieff et al., *Pharmacology,* 301(1): 241-248 (2002) or Hersperger et al., *J Med Chem.,* 43(4):675-82 (2000); a benzofuran, such as a compound disclosed in U.S. Pat. Nos. 5,902,824, 6,211,203, 6,514,996, 6,716,987, 6,376,535, 6,080,782, or 6,054,475, EP 819688, EP685479, or Perrier et al., *Bioorg. Med. Chem. Lett.* 9:323-326 (1999); a phenanthridine, such as that disclosed in U.S. Pat. Nos. 6,191,138, 6,121,279, or 6,127,378; a benzoxazole, such as that disclosed in U.S. Pat. Nos. 6,166,041 or 6,376,485; a purine derivative, such as a compound disclosed in U.S. Pat. No. 6,228,859; a benzamide, such as a compound described in U.S. Pat. Nos. 5,981,527 or 5,712,298, W095/01338, WO 97/48697, or Ashton et al., *J. Med Chem* 37: 1696-1703 (1994); a substituted phenyl compound, such as a compound disclosed in U.S. Pat. Nos. 6,297,264, 5,866,593, 5,859,034, 6,245,774, 6,197,792, 6,080,790, 6,077,854, 5,962,483, 5,674,880, 5,786,354, 5,739,144, 5,776,958, 5,798,373, 5,891,896, 5,849,770, 5,550,137, 5,340,827, 5,780,478, 5,780,477, or 5,633,257, or WO 95/35283; a substituted biphenyl compound, such as that disclosed in U.S. Pat. No. 5,877,190; or a quinilinone, such as a compound described in U.S. Pat. No. 6,800,625 or WO 98/14432.

Additional examples of reported PDE4 inhibitors useful in methods provided herein include a compound disclosed in U.S. Pat. Nos. 6,716,987, 6,514,996, 6,376,535, 6,740,655, 6,559,168, 6,069,151, 6,365,585, 6,313,116, 6,245,774, 6,011,037, 6,127,363, 6,303,789, 6,316,472, 6,348,602, 6,331,543, 6,333,354, 5,491,147, 5,608,070, 5,622,977, 5,580,888, 6,680,336, 6,569,890, 6,569,885, 6,500,856, 6,486,186, 6,458,787, 6,455,562, 6,444,671, 6,423,710, 6,376,489, 6,372,777, 6,362,213, 6,313,156, 6,294,561, 6,258,843, 6,258,833, 6,121,279, 6,043,263, RE 38,624, 6,297,257, 6,251,923, 6,613,794, 6,407,108, 6,107,295, 6,103,718, 6,479,494, 6,602,890, 6,545,158, 6,545,025, 6,498,160, 6,743,802, 6,787,554, 6,828,333, 6,869,945, 6,894,041, 6,924,292, 6,949,573, 6,953,810, 5,972,927, 5,962,492, 5,814,651, 5,723,460, 5,716,967, 5,686,434, 5,502,072, 5,116,837, 5,091,431; 4,670,434; 4,490,371; 5,710,160, 5,710,170, 6,384,236, or 3,941,785, US20050119225, US20050026913, WO 99/65880, WO 00/26201, WO 98/06704, WO 00/59890, WO9907704, WO9422852, WO 98/20007, WO 02/096423, WO 98/18796, WO 98/02440, WO 02/096463, WO 97/44337, WO 97/44036, WO 97/44322, EP 0763534, Aoki et al., *J Pharmacol Exp Ther.,* 295(1):255-60 (2000), Del Piaz et al., *Eur. J. Med. Chem.,* 35; 463-480 (2000), or Barnette et al., Pharmacol. Rev. Commun. 8: 65-73 (1997).

In some embodiments, the reported PDE4 inhibitor is Cilomilast (SB-207499); Filaminast; Tibenelast (LY-186655); Ibudilast; Piclamilast (RP 73401); Doxofylline; Cipamfylline (HEP-688); atizoram (CP-80633); theophylline; isobutylmethylxanthine; Mesopram (ZK-117137); Zardaverine; vinpocetine; Rolipram (ZK-62711); Arofylline (LAS-31025); roflumilast (BY-217); Pumafentrin (BY-343); Denbufylline; EHNA; milrinone; Siguazodan; Zaprinast; Tolafentrine; Isbufylline; IBMX; 1C-485; diphylline; verolylline; bamifylline; pentoxyfilline; enprofilline; lirimilast (BAY 19-8004); filaminast (WAY-PDA-641); benafentrine; trequinsin; nitroquazone; Tetomilast (OPC-6535); AH-21-132; AWD-12-343; AWD-12-281; AWD-12-232; CC-7085; CDC-801; CDC-998; CDP-840; CH-422; CH-673; CH-928; CH-3697; CH-3442; CH-2874; CH-4139; Chiroscience 245412; CI-1018; CI-1044; CI-1118; CP-353164; CP-77059; CP-146523; CP-293321; CP-220629; CT-2450; CT-2820; CT-3883; CT-5210; D-4418; D-22888; E-4021; EMD 54622; GF-248; GW-3600; IC-485; ICI 63197; IPL-4088; KF-19514; KW-4490; L-787258; L-826141; L-791943; NCS-613; Org-30029; Org-20241; Org-9731; PD-168787; PD-190749; PD-190036; PDB-093; PLX650; PLX369; PLX371; PLX788; PLX939; Ro-20-1724; RPR-132294; RPR-117658A; RPR-114597; RPR-122818; RPR-132703; RS-17597; RS-25344; RS-14203; SCA 40; Sch-351591; SDZ-ISQ-844; SKF-107806; SKF 96231; T-440; T-2585; WAY-126120; WAY-122331; WAY-127093B; V-11294A; VMX 554; VMX 565; XT-044; XT-611; YM-58897; YM-976; methyl 3-[6-(2H-3,4,5,6-tetrahydropyran-2-yloxy)-2-(3-thienylcarbonyl)benzo[b]furan-3-yl]propanoate; 4-[4-methoxy-3-(5-phenylpentyloxy)phenyl]-2-methylbenzoic acid; methyl 3-{2-[(4-chlorophenyl)carbonyl]-6-hydroxybenzo[b]furan-3-yl }propanoate; (R*, R*)-(±)-methyl 3-acetyl-4-[3-(cyclopentyloxy)-4-methoxyphenyl]-3-methyl-3-pyrrolidinecarboxylat; or 4-(3-bromophenyl)-1-ethyl-7-methylhydropyridino[2,3-b]pyridin-2-one.

Non-limiting examples of a reported PDE5 inhibitor useful in a combination or method described herein include a pyrimidine or pyrimidinone derivative, such as a compound described in U.S. Pat. Nos. 6,677,335, 6,458,951, 6,251,904, 6,787,548, 5,294,612, 5,250,534, or 6,469,012, WO 94/28902, WO96/16657, EP0702555, or Eddahibi, *Br. J. Pharmacol.,* 125(4): 681-688 (1988); a griseolic acid derivative, such as a compound disclosed in U.S. Pat. No. 4,460,765; a 1-arylnaphthalene lignan, such as that described in Ukita, *J. Med. Chem.* 42(7): 1293-1305 (1999); a quinazoline derivative, such as 4-[[3',4'-(methylenedioxy)benzyl]amino]-6-methoxyquinazoline) or a compound described in U.S. Pat. Nos. 3,932,407 or 4,146,718, or RE 31,617; a pyrroloquinolones or pyrrolopyridinone, such as that described in U.S. Pat. Nos. 6,686,349, 6,635,638, or 6,818,646, US20050113402; a carboline derivative, such a compound described in U.S. Pat. Nos. 6,492,358, 6,462,047, 6,821,975, 6,306,870, 6,117,881, 6,043,252, or 3,819,631, US20030166641, WO 97/43287, Daugan et al., *J Med Chem.,* 46(21):4533-42 (2003), and Daugan et al., *J Med Chem.,* 9;46(21):4525-32 (2003); an imidazo derivative, such as a compound disclosed in U.S. Pat. Nos. 6,130,333, 6,566,360, 6,362,178, or 6,582,351, US20050070541, or US20040067945; or a compound described in U.S. Pat. Nos. 6,825,197, 6,943,166, 5,981,527, 6,576,644, 5,859,009, 6,943,253, 6,864,253, 5,869,516, 5,488,055, 6,140,329, 5,859,006, or 6,143,777, WO 96/16644, WO 01/19802, WO 96/26940, Dunn, Org. Proc. Res. Dev., 9: 88-97 (2005), or Bi et al., *Bioorg Med Chem Lett.,* 11(18):2461-4 (2001).

In some embodiments, a reported PDE5 inhibitor is zaprinast; MY-5445; dipyridamole; vinpocetine; FR229934; 1-methyl-3-isobutyl-8-(methylamino)xanthine; furazlocillin; Sch-51866; E4021; GF-196960; IC-351; T-1032; sildenafil; tadalafil; vardenafil; DMPPO; RX-RA-69; KT-734; SKF-96231; ER-21355; BF/GP-385; NM-702; PLX650; PLX134; PLX369; PLX788; or vesnarinone.

In some embodiments, the reported PDE5 inhibitor is sildenafil or a related compound disclosed in U.S. Pat. Nos. 5,346,901, 5,250,534, or 6,469,012; tadalafil or a related compound disclosed in U.S. Pat. No. 5,859,006, 6,140,329, 6,821,975, or 6,943,166; or vardenafil or a related compound disclosed in U.S. Pat. No. 6,362,178.

Non-limiting examples of a reported PDE6 inhibitor useful in a combination or method described herein include dipyridamole or zaprinast.

Non-limiting examples of a reported PDE7 inhibitor for use in the combinations and methods described herein include BRL 50481; PLX369; PLX788; or a compound described in U.S. Pat. Nos. 6,818,651; 6,737,436, 6,613,778, 6,617,357; 6,146,876, 6,838,559, or 6,884,800, US20050059686; US20040138279; US20050222138; US20040214843; US20040106631; US 20030045557; US 20020198198; US20030162802, US20030092908, US 20030104974; US20030100571; 20030092721; or US20050148604.

A non-limiting examples of a reported inhibitor of PDE8 activity is dipyridamole.

Non-limiting examples of a reported PDE9 inhibitor useful in a combination or method described herein include SCH-51866; IBMX; or BAY 73-6691.

Non-limiting examples of a PDE10 inhibitor include sildenafil; SCH-51866; papaverine; Zaprinast; Dipyridamole; E4021; Vinpocetine; EHNA; Milrinone; Rolipram; PLX107; or a compound described in U.S. Pat. No. 6,930,114, US20040138249, or US20040249148.

Non-limiting examples of a PDE11 inhibitor includes IC-351 or a related compound described in WO 9519978; E4021 or a related compound described in WO 9307124; UK-235,187 or a related compound described in EP 579496; PLX788; Zaprinast; Dipyridamole; or a compound described in US20040106631 or Maw et al., *Bioorg Med Chem Lett.* 2003 Apr. 17;13(8):1425-8.

In some embodiments, the reported PDE inhibitor is a compound described in U.S. Pat. Nos. 5,091,431, 5,081,242, 5,066,653, 5,010,086, 4,971,972, 4,963,561, 4,943,573, 4,906,628, 4,861,891, 4,775,674, 4,766,118, 4,761,416, 4,739,056, 4,721,784, 4,701,459, 4,670,434, 4,663,320, 4,642,345, 4,593,029, 4,564,619, 4,490,371, 4,489,078, 4,404,380, 4,370,328, 4,366,156, 4,298,734, 4,289,772, RE 30,511, 4,188,391, 4,123,534, 4,107,309, 4,107,307, 4,096,257, 4,093,617, 4,051,236, or 4,036,840.

In some embodiments, the reported PDE inhibitor inhibits dual-specificity PDE. Non-limiting examples of a dual-specificity PDE inhibitor useful in a combination or method described herein include a cAMP-specific or cGMP-specific PDE inhibitor described herein; MMPX; KS-505a; W-7; a phenothiazine; Bay 60-7550 or a related compound described in Boess et al., *Neuropharmacology,* 47(7):1081-92 (2004); UK-235,187 or a related compound described in EP 579496; or a compound described in U.S. Pat. Nos. 6,930,114 or 4,861,891, US20020132754, US20040138249, US20040249148, US20040106631, WO 951997, or Maw et al., *Bioorg Med Chem Lett.* 2003 Apr 17;13(8):1425-8.

In some embodiments, a reported PDE inhibitor exhibits dual-selectivity, being substantially more active against two PDE isozymes relative to other PDE isozymes. For example, in some embodiments, a reported PDE inhibitor is a dual PDE4/PDE7 inhibitor, such as a compound described in US20030104974; a dual PDE3/PDE4 inhibitor, such as zardaverine, tolafentrine, benafentrine, trequinsine, Org-30029, L-686398, SDZ-ISQ-844, Org-20241, EMD-54622, or a compound described in U.S. Pat. Nos. 5,521,187, or 6,306,869; or a dual PDE1/PDE4 inhibitor, such as KF19514 (5-phenyl-3-(3-pyridyl)methyl-3H-imidazo[4,5-c][1,8] naphthyridin-4 (5H)-one).

The combination of the muscarinic agent donepezil with enoximone resulted in synergistic activity (see Example 8 below). Donepezil alone has an $EC_{50}$ of 2.02 µM for neuronal differentiation. Enozimone alone has an $EC_{50}$ of 6.76 µM. The concentration of each agent in combination to reach 50% activity in neuronal differentiation is 0.78 µM, resulting in a CI of 0.55. As the CI is less than 1, the two compounds have a synergistic effect in neuronal differentiation.

Furthermore, the neurogenic agent in combination with a muscarinic agent, such as an inhibitor of AChE activity, may be a reported neurosteroid. Non-limiting examples of such a neurosteroid include pregnenolone and allopregnenalone.

Alternatively, the neurogenic sensitizing agent may be a reported non-steroidal anti-inflammatory drug (NSAID) or an anti-inflammatory mechanism targeting agent in general. Non-limiting examples of a reported NSAID include a cyclooxygenase inhibitor, such as indomethacin, ibuprofen, celecoxib, cofecoxib, naproxen, or aspirin.

In additional embodiments, the neurogenic agent in combination with a muscarinic agent, such as an inhibitor of AChE activity, may be a reported agent for treating migraines. Non-limiting examples of such an agent include a triptan, such as almotriptan or almotriptan malate; naratriptan or naratriptan hydrochloride; rizatriptan or rizatriptan benzoate; sumatriptan or sumatriptan succinate; zolmatriptan or zolmitriptan, frovatriptan or frovatriptan succinate; or eletriptan or eletriptan hydrobromide. Embodiments of the disclosure may exclude combinations of triptans and an SSRI or SNRI that result in life threatening serotonin syndrome.

Other non-limiting examples include an ergot derivative, such as dihydroergotamine or dihydroergotamine mesylate, ergotamine or ergotamine tartrate; diclofenac or diclofenac potassium or diclofenac sodium; flurbiprofen; amitriptyline; nortriptyline; divalproex or divalproex sodium; propranolol or propranolol hydrochloride; verapamil; methysergide (CAS RN 361-37-5); metoclopramide; prochlorperazine (CAS RN 58-38-8); acetaminophen; topiramate; GW274150 ([2-[(1-iminoethyl)amino]ethyl]-L-homocysteine); or ganaxalone (CAS RN 38398-32-2).

Additional non-limiting examples include a COX-2 inhibitor, such as Celecoxib.

In other embodiments, the neurogenic agent in combination with a muscarinic agent, such as an inhibitor of AChE activity, may be a reported modulator of a nuclear hormone receptor. Nuclear hormone receptors are activated via ligand interactions to regulate gene expression, in some cases as part of cell signaling pathways. Non-limiting examples of a reported modulator include a dihydrotestosterone agonist such as dihydrotestosterone; a 2-quinolone like LG121071 (4-ethyl-1,2,3,4-tetrahydro-6-(trifluoromethyl)-8-pyridono [5,6-g]-quinoline); a non-steroidal agonist or partial agonist compound described in U.S. Pat. No. 6,017,924; LGD2226 (see WO 01/16108, WO 01/16133, WO 01/16139, and Rosen et al. "Novel, non-steroidal, selective androgen receptor modulators (SARMs) with anabolic activity in bone and muscle and improved safety profile." *J Musculoskelet Neuronal Interact.* 2002 2(3):222-4); or LGD2941 (from collaboration between Ligand Pharmaceuticals Inc. and TAP Pharmaceutical Products Inc.).

Additional non-limiting examples of a reported modulator include a selective androgen receptor modulator (SARM) such as andarine, ostarine, prostarin, or andromustine (all from GTx, Inc.); bicalutamide or a bicalutamide derivative such as GTx-007 (U.S. Pat. No. 6,492,554); or a SARM as described in U.S. Pat. No. 6,492,554.

Further non-limiting examples of a reported modulator include an androgen receptor antagonist such as cyproterone, bicalutamide, flutamide, or nilutamide; a 2-quinolone such as LG 120907, represented by the following structure

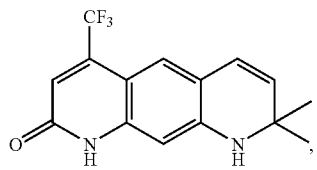

or a derivative compound represented by the following structure

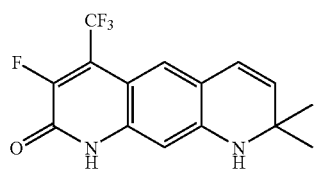

(see Allan et al. "Therapeutic androgen receptor ligands" *Nucl Recept Signal* 2003; 1: e009); a phthalamide, such as a modulator as described by Miyachi et al. ("Potent novel non-steroidal androgen antagonists with a phthalimide skeleton." *Bioorg. Med. Chem. Lett.* 1997 7:1483-1488); osaterone or osaterone acetate; hydroxyflutamide; or a non-steroidal antagonist described in U.S. Pat. No. 6,017,924.

Other non-limiting examples of a reported modulator include a retinoic acid receptor agonist such as all-trans retinoic acid (Tretinoin); isotretinoin (13-cis-retinoic acid); 9-cis retinoic acid; bexarotene; TAC-101 (4-[3,5-bis(trimethylsilyl)benzamide]benzoic acid); AC-261066 (see Lund et al. "Discovery of a potent, orally available, and isoform-selective retinoic acid beta2 receptor agonist." *J Med Chem.* 2005 48(24):7517-9); LGD1550 ((2E,4E,6E)-3-methyl-7-(3,5-di-ter-butylphen-yl)octatrienoic acid); E6060 (E6060 [4-{5-[7-fluoro-4-(trifluoromethyl)benzo[b]furan-2-yl]-1H-2-pyrrolyl}benzoic acid]; agonist 1 or 2 as described by Schapira et al. ("In silico discovery of novel Retinoic Acid Receptor agonist structures." *BMC Struct Biol.* 2001; 1:1 (published online 2001 Jun. 4) where "Agonist 1 was purchased from Bionet Research (catalog number 1G-433S). Agonist 2 was purchased from Sigma-Aldrich (Sigma Aldrich library of rare chemicals. Catalog number S08503-1"); a synthetic acetylenic retinoic acid, such as AGN 190121 (CAS RN: 132032-67-8), AGN 190168 (or Tazarotene or CAS RN 118292-40-3), or its metabolite AGN 190299 (CAS RN 118292-41-4); Etretinate; acitretin; an acetylenic retinoate, such as AGN 190073 (CAS 132032-68-9), or AGN 190089 (or 3-Pyridinecarboxylic acid, 6-(4-(2,6,6-trimethyl-1-cyclohexen-1-yl)-3-buten-1-ynyl)-, ethyl ester or CAS RN 116627-73-7).

In further embodiments, the additional agent for use in combination with a muscarinic agent may be a reported modulator be selected from thyroxin, tri-iodothyronine, or levothyroxine.

Alternatively, the additional agent is a vitamin D (1,25-dihydroxyvitamine $D_3$) receptor modulator, such as calcitriol or a compound described in Ma et al. ("Identification and characterization of noncalcemic, tissue-selective, nonsecosteroidal vitamin D receptor modulators." *J Clin Invest.* 2006 116(4):892-904) or Molnar et al. ("Vitamin D receptor agonists specifically modulate the volume of the ligand-binding pocket." *J Biol Chem.* 2006 281(15):10516-26) or Milliken et al. ("EB1089, a vitamin D receptor agonist, reduces proliferation and decreases tumor growth rate in a mouse model of hormone-induced mammary cancer." *Cancer Lett.* 2005 229 (2):205-15) or Yee et al. ("Vitamin D receptor modulators for inflammation and cancer." *Mini Rev Med Chem.* 2005 5(8): 761-78) or Adachi et al. "Selective activation of vitamin D receptor by lithocholic acid acetate, a bile acid derivative." *J Lipid Res.* 2005 46(1):46-57).

Furthermore, the additional agent may be a reported cortisol receptor modulator, such as methylprednisolone or its prodrug methylprednisolone suleptanate; PI-1020 (NCX-1020 or budesonide-21-nitrooxymethylbenzoate); fluticasone furoate; GW-215864; betamethasone valerate; beclomethasone; prednisolone; or BVT-3498 (AMG-311).

Alternatively, the additional agent may be a reported aldosterone (or mineralocorticoid) receptor modulator, such as Spironolactone or Eplerenone.

In other embodiments, the additional agent may be a reported progesterone receptor modulator such as Asoprisnil (CAS RN 199396-76-4 ); mesoprogestin or J1042; J956; medroxyprogesterone acetate (MPA); R5020; tanaproget; trimegestone; progesterone; norgestomet; melengestrol acetate; mifepristone; onapristone; ZK137316; ZK230211 (see Fuhrmann et al. "Synthesis and biological activity of a novel, highly potent progesterone receptor antagonist." *J Med Chem.* 2000 43(26):5010-6); or a compound described in Spitz "Progesterone antagonists and progesterone receptor modulators: an overview." *Steroids* 2003 68(10-13):981-93.

In further embodiments, the additional agent may be a reported i) peroxisome proliferator-activated receptor agonist such as muraglitazar; tesaglitazar; reglitazar; GW-409544 (see Xu et al. "Structural determinants of ligand binding selectivity between the peroxisome proliferator-activated receptors." *Proc Natl Acad Sci U S A.* 2001 98(24):13919-24); or DRL 11605 (Dr. Reddy's Laboratories); ii) a peroxisome proliferator-activated receptor alpha agonist like clofibrate; ciprofibrate; fenofibrate; gemfibrozil; DRF-10945 (Dr. Reddy's Laboratories); iii) a peroxisome proliferator-activated receptor delta agonist such as GW501516 (CAS RN 317318-70-0); or iv) a peroxisome proliferator-activated gamma receptor agonist like a hydroxyoctadecadienoic acid (HODE); a prostaglandin derivatives, such as 15-deoxy-Delta12,14-prostaglandin J2; a thiazolidinedione (glitazone), such as pioglitazone, troglitazone; rosiglitazone or rosiglitazone maleate; ciglitazone; Balaglitazone or DRF-2593; AMG 131 (from Amgen); or G1262570 (from GlaxoWellcome).

In additional embodiments, the additional agent may be a reported modulator of an "orphan" nuclear hormone receptor. Embodiments include a reported modulator of a liver X receptor, such as a compound described in U.S. Pat. No. 6,924,311; a farnesoid X receptor, such as GW4064 as described by Maloney et al. ("Identification of a chemical tool for the orphan nuclear receptor FXR." *J Med Chem.* 2000 43(16):2971-4); a RXR receptor; a CAR receptor, such as 1,4-bis[2-(3,5-dichloropyridyloxy)]benzene (TCPOBOP); or a PXR receptor, such as SR-12813 (tetra-ethyl 2-(3,5-di-tert-butyl-4-hydroxyphenyl)ethenyl-1,1-bisphosphonate).

The combination of the muscarinic agent tacrine with rosiglitazone resulted in synergistic activity (see Example 8 below). Tacrine alone has an $EC_{50}$ of 8.0 uM for neuronal differentiation. Rosiglitazone alone has an $EC_{50}$ of 0.94 µM. The concentration of each agent in combination to reach 50% activity in neuronal differentiation is 0.53 µM, resulting in a CI of 0.67. As the CI is less than 1, the two compounds have a synergistic effect in neuronal differentiation.

In additional embodiments, the agent in combination with a muscarinic agent, such as an inhibitor of AChE activity, is ethyl eicosapentaenoate or ethyl-EPA (also known as 5,8,11,14,17-eicosapentaenoic acid ethyl ester or miraxion, CAS RN 86227-47-6), docosahexaenoic acid (DHA), or a retinoid acid drug. As an additional non-limiting example, the agent may be Omacor, a combination of DHA and EPA, or idebenone (CAS RN 58186-27-9).

In further embodiments, a reported nootropic compound may be used as an agent in combination with a muscarinic agent, such as an inhibitor of AChE activity. Non-limiting examples of such a compound include Piracetam (Nootropil), Aniracetam, Oxiracetam, Pramiracetam, Pyritinol (Enerbol), Ergoloid mesylates (Hydergine), Galantamine, Selegiline, Centrophenoxine (Lucidril), Desmopressin (DDAVP), Nicergoline, Vinpocetine, Picamilon, Vasopressin, Milacemide, FK-960, FK-962, levetiracetam, nefiracetam, or hyperzine A (CAS RN: 102518-79-6).

Additional non-limiting examples of such a compound include anapsos (CAS RN 75919-65-2), nebracetam (CAS RN 97205-34-0 or 116041-13-5), metrifonate, ensaculin (or CAS RN 155773-59-4 or KA-672) or ensaculin HCl, Rokan (CAS RN 122933-57-7 or EGb 761), AC-3933 (5-(3-methoxyphenyl)-3-(5-methyl-1,2,4-oxadiazol-3-yl)-2-oxo-1,2-dihydro-1,6-naphthyridine) or its hydroxylated metabolite SX-5745 (3-(5-hydroxymethyl-1,2,4-oxadiazol-3-yl)-5-(3-methoxyphenyl)-2-oxo-1,2-dihydro-1,6-naphthyridine), JTP-2942 (CAS RN 148152-77-6), sabeluzole (CAS RN 104383-17-7), ladostigil (CAS RN 209394-27-4), choline alphoscerate (CAS RN 28319-77-9 or Gliatilin), Dimebon (CAS RN 3613-73-8), tramiprosate (CAS RN 3687-18-1), omigapil (CAS RN 181296-84-4), cebaracetam (CAS RN 113957-09-8), fasoracetam (CAS RN 110958-19-5), PD-151832 (see Jaen et al. "In vitro and in vivo evaluation of the subtype-selective muscarinic agonist PD 151832." *Life Sci.* 1995 56(11-12):845-52), Vinconate (CAS RN 70704-03-9), PYM-50028 PYM-50028 (Cogane) or PYM-50018 (Myogane) as described by Harvey ("Natural Products in Drug Discovery and Development. 27-28 Jun. 2005, London, UK." IDrugs. 2005 8(9):719-21), SR-46559A (3-[N-(2 diethyl-amino-2-methylpropyl)-6-phenyl-5-propyl), dihydroergocristine (CAS RN 17479-19-5), dabelotine (CAS RN 118976-38-8), zanapezil (CAS RN 142852-50-4).

Further non-limiting examples include NBI-113 (from Neurocrine Biosciences, Inc.), NDD-094 (from Novartis), P-58 or P58 (from Pfizer), or SR-57667 (from Sanofi-Synthelabo).

Moreover, an agent in combination with a muscarinic agent, such as an inhibitor of AChE activity, may be a reported modulator of the nicotinic receptor. Non-limiting examples of such a modulator include nicotine, acetylcholine, carbamylcholine, epibatidine, ABT-418 (structurally similar to nicotine, with an ixoxazole moiety replacing the pyridyl group of nicotine), epiboxidine (a structural analogue with elements of both epibatidine and ABT-418), ABT-594 (azetidine analogue of epibatidine), lobeline, SSR-591813, represented by the following formula

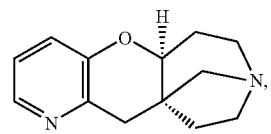

or SIB-1508 (altinicline).

In additional embodiments, an agent used in combination with a muscarinic agent, such as an inhibitor of AChE activity, is a reported aromatase inhibitor. Reported aromatase inhibitors include, but are not limited to, nonsteroidal or steroidal agents. Non-limiting examples of the former, which inhibit aromatase via the heme prosthetic group, include anastrozole (Arimidex®), letrozole (Femara®), or vorozole (Rivisor). Non-limiting examples of steroidal aromatase inhibitors AIs, which inactivate aromatase, include, but are not limited to, exemestane (Aromasin®), androstenedione, or formestane (lentaron).

Additional non-limiting examples of a reported aromatase for use in a combination or method as disclosed herein include aminoglutethimide, 4-androstene-3,6,17-trione (or "6-OXO"), or zoledronic acid or Zometa (CAS RN 118072-93-8).

Further embodiments include a combination of a muscarinic agent, such as an inhibitor of AChE activity, and a reported selective estrogen receptor modulator (SERM) may be used as described herein. Non-limiting examples include tamoxifen, raloxifene, toremifene, clomifene, bazedoxifene, arzoxifene, or lasofoxifene.

In other embodiments, a combination of a muscarinic agent, such as an inhibitor of AChE activity, and a reported cannabinoid receptor modulator may be used as described herein. Non-limiting examples include synthetic cannabinoids, endogenous cannabinoids, or natural cannabinoids. In some embodiments, the reported cannabinoid receptor modulator is rimonabant (SR141716 or Acomplia), nabilone, levonantradol, marinol, or sativex (an extract containing both THC and CBD). Non-limiting examples of endogenous cannabinoids include arachidonyl ethanolamine (anandamide); analogs of anandamide, such as docosatetraenylethanolamide or homo-γ-linoenylethanolamide; N-acyl ethanolamine signalling lipids, such as the noncannabimimetic palmitoylethanolamine or oleoylethanolamine; or 2-arachidonyl glycerol. Non-limiting examples of natural cannabinoids include tetrahydrocannabinol (THC), cannabidiol (CBD), cannabinol (CBN), cannabigerol (CBG), cannabichromene (CBC), cannabicyclol (CBL), cannabivarol (CBV), tetrahydrocannabivarin (THCV), cannabidivarin (CBDV), cannabichromevarin (CBCV), cannabigerovarin (CBGV), or cannabigerol monoethyl ether (CBGM).

In yet further embodiments, an agent used in combination with a muscarinic agent, such as an inhibitor of AChE activity, is a reported FAAH (fatty acid amide hydrolase) inhibitor. Non-limiting examples of reported inhibitor agents include URB597 (3'-carbamoyl-biphenyl-3-yl-cyclohexylcarbamate); CAY10401 (1-oxazolo[4,5-b]pyridin-2-yl-9-octadecyn-1-one); OL-135 (1-oxo-1[5-(2-pyridyl)-2-yl]-7-phenylheptane); anandamide (CAS RN 94421-68-8); AA-5-HT (see Bisogno et al. "Arachidonoylserotonin and other novel inhibitors of fatty acid amide hydrolase." *Biochem Biophys Res Commun.* 1998 248(3):515-22); 1-Octanesulfonyl fluoride; or O-2142 or another arvanil derivative FAAH inhibitor as described by Di Marzo et al. ("A structure/activity relationship study on arvanil, an endocannabinoid and vanilloid hybrid." *J Pharmacol Exp Ther.* 2002 300(3):984-91).

Further non-limiting examples include SSR 411298 (from Sanofi-Aventis), JNJ28614118 (from Johnson & Johnson), or SSR 101010 (from Sanofi-Aventis)

In additional embodiments, an agent in combination with a muscarinic agent, such as an inhibitor of AChE activity, may be a reported modulator of nitric oxide function. One non-limiting example is sildenafil (Viagra®).

In additional embodiments, an agent in combination with a muscarinic agent, such as an inhibitor of AChE activity, may be a reported modulator of prolactin or a prolactin modulator.

In additional embodiments, an agent in combination with a muscarinic agent, such as an inhibitor of AChE activity, is a reported anti-viral agent, with ribavirin and amantadine as non-limiting examples.

In additional embodiments, an agent in combination with a muscarinic agent, such as an inhibitor of AChE activity, may be a component of a natural product or a derivative of such a component. In some embodiments, the component or derivative thereof is in an isolated form, such as that which is separated from one or more molecules or macromolecules normally found with the component or derivative before use in a combination or method as disclosed herein. In other embodiments, the component or derivative is completely or partially purified from one or more molecules or macromolecules normally found with the component or derivative. Exemplary cases of molecules or macromolecules found with a component or derivative as described herein include a plant or plant part, an animal or animal part, and a food or beverage product.

Non-limiting examples such a component include folic acid; a flavinoid, such as a citrus flavonoid; a flavonol, such as Quercetin, Kaempferol, Myricetin, or Isorhamnetin; a flavone, such as Luteolin or Apigenin; a flavanone, such as Hesperetin, Naringenin, or Eriodictyol; a flavan-3-ol (including a monomeric, dimeric, or polymeric flavanol), such as (+)-Catechin, (+)-Gallocatechin, (−)-Epicatechin, (−)-Epigallocatechin, (−)-Epicatechin 3-gallate, (−)-Epigallocatechin 3-gallate, Theaflavin, Theaflavin 3-gallate, Theaflavin 3'-gallate, Theaflavin 3,3' digallate, a Thearubigin, or Proanthocyanidin; an anthocyanidin, such as Cyanidin, Delphinidin, Malvidin, Pelargonidin, Peonidin, or Petunidin; an isoflavone, such as daidzein, genistein, or glycitein; flavopiridol; a prenylated chalcone, such as Xanthohumol; a prenylated flavanone, such as Isoxanthohumol; a non-prenylated chalcone, such as Chalconaringenin; a non-prenylated flavanone, such as Naringenin; Resveratrol; or an anti-oxidant neutraceutical (such as any present in chocolate, like dark chocolate or unprocessed or unrefined chocolate).

Additional non-limiting examples include a component of *Gingko biloba*, such as a flavo glycoside or a terpene. In some embodiments, the component is a flavanoid, such as a flavonol or flavone glycoside, or a quercetin or kaempferol glycoside, or rutin; or a terpenoid, such as ginkgolides A, B, C, or M, or bilobalide.

Further non-limiting examples include a component that is a flavanol, or a related oligomer, or a polyphenol as described in US2005/245601AA, US2002/018807AA, US2003/180406AA, US2002/086833AA, US2004/0236123, WO9809533, or WO9945788; a procyanidin or derivative thereof or polyphenol as described in US2005/171029AA; a procyanidin, optionally in combination with L-arginine as described in US2003/104075AA; a low fat cocoa extract as described in US2005/031762AA; lipophilic bioactive compound containing composition as described in US2002/107292AA; a cocoa extract, such as those containing one or more polyphenols or procyanidins as described in US2002/004523AA; an extract of oxidized tea leaves as described in U.S. Pat. Nos. 5,139,802 or 5,130,154; a food supplement as described in WO 2002/024002.

Of course a composition comprising any of the above components, alone or in combination with a muscarinic agent as described herein is included within the disclosure.

In additional embodiments, an agent in combination with a muscarinic agent, such as an inhibitor of AChE activity, may be a reported calcitonin receptor agonist such as calcitonin or the 'orphan peptide' PHM-27 (see Ma et al. "Discovery of novel peptide/receptor interactions: identification of PHM-27 as a potent agonist of the human calcitonin receptor." *Biochem Pharmacol.* 2004 67(7):1279-84). A further non-limiting example is the agonist from Kemia, Inc.

In an alternative embodiment, the agent may be a reported modulator of parathyroid hormone activity, such as parathyroid hormone, or a modulator of the parathyroid hormone receptor.

In additional embodiments, an agent in combination with a muscarinic agent, such as an inhibitor of AChE activity, may a reported antioxidant, such as N-acetylcysteine or acetylcysteine; disufenton sodium (or CAS RN 168021-79-2 or Cerovive); activin (CAS RN 104625-48-1); selenium; L-methionine; an alpha, gamma, beta, or delta, or mixed, tocopherol; alpha lipoic acid; Coenzyme Q; Benzimidazole; benzoic acid; dipyridamole; glucosamine; IRFI-016 (2(2,3-dihydro-5-acetoxy-4,6,7-trimethylbenzofuranyl) acetic acid); L-camosine; L-Histidine; glycine; flavocoxid (or LIMBREL); baicalin, optionally with catechin (3,3',4',5,7-pentahydroxyflavan (2R,3S form)), and/or its stereo-isomer; masoprocol (CAS RN 27686-84-6); mesna (CAS RN 19767-45-4); probucol (CAS RN 23288-49-5); silibinin (CAS RN 22888-70-6); sorbinil (CAS RN 68367-52-2); spermine; tangeretin (CAS RN 481-53-8); butylated hydroxyanisole (BHA); butylated hydroxytoluene (BHT); propyl gallate (PG); tertiary-butyl-hydroquinone (TBHQ); nordihydroguaiaretic acid (CAS RN 500-38-9); astaxanthin (CAS RN 472-61-7); or an antioxidant flavonoid.

Additional non-limiting examples include a vitamin, such as vitamin A (Retinol) or C (Ascorbic acid) or E (including Tocotrienol and/or Tocopherol); a vitamin cofactors or mineral, such as Coenzyme Q10 (CoQ10), Manganese, or Melatonin; a carotenoid terpenoid, such as Lycopene, Lutein, Alpha-carotene, Beta-carotene, Zeaxanthin, Astaxanthin, or Canthaxantin; a non-carotenoid terpenoid, such as Eugenol; a flavonoid polyphenolic (or bioflavonoid); a flavonol, such as Resveratrol, Pterostilbene (methoxylated analogue of resveratrol), Kaempferol, Myricetin, Isorhamnetin, a Proanthocyanidin, or a tannin; a flavone, such as Quercetin, rutin, Luteolin, Apigenin, or Tangeritin; a flavanone, such as Hesperetin or its metabolite hesperidin, naringenin or its precursor naringin, or Eriodictyol; a flavan-3-ols (anthocyanidins), such as Catechin, Gallocatechin, Epicatechin or a gallate form thereof, Epigallocatechin or a gallate form thereof, Theaflavin or a gallate form thereof, or a Thearubigin; an isoflavone phytoestrogens, such as Genistein, Daidzein, or Glycitein; an anthocyanins, such as Cyanidin, Delphinidin, Malvidin, Pelargonidin, Peonidin, or Petunidin; a phenolic acid or ester thereof, such as Ellagic acid, Gallic acid, Salicylic acid, Rosmarinic acid, Cinnamic acid or a derivative thereof like ferulic acid, Chlorogenic acid, Chicoric acid, a Gallotannin, or an Ellagitannin; a nonflavonoid phenolic, such as Curcumin; an anthoxanthin, betacyanin, Citric acid, Uric acid, R-α-lipoic acid, or Silymarin.

Further non-limiting examples include 1-(carboxymethylthio)tetradecane; 2,2,5,7,8-pentamethyl-1-hydroxychroman; 2,2,6,6-tetramethyl-4-piperidinol-N-oxyl; 2,5-di-tert-butylhydroquinone; 2-tert-butylhydroquinone; 3,4-dihydroxyphenylethanol; 3-hydroxypyridine; 3-hydroxytamoxifen; 4-coumaric acid; 4-hydroxyanisole; 4-hydroxyphenylethanol; 4-methylcatechol; 5,6,7,8-tetrahydrobiopterin; 6,6'-methylenebis(2,2-dimethyl-4-methanesulfonic acid-1,2-dihydroquinoline); 6-hydroxy-2,5,7,8-tetramethylchroman-2-carboxylic acid; 6-methyl-2-ethyl-3-hydroxypyridine; 6-O-palmitoylascorbic acid; acetovanillone; acteoside; Actovegin; allicin; allyl sulfide; alpha-pentyl-3-(2-quinolinylmethoxy)benzenemethanol; alpha-tocopherol acetate; apolipoprotein A-IV; bemethyl; boldine; bucillamine; Calcium Citrate; Canthaxanthin; crocetin; diallyl trisulfide; dicarbine; dihydrolipoic acid; dimephosphon; ebselen; Efamol; enkephalin-Leu,Ala(2)-Arg(6)-; Ergothioneine; esculetin; essential 303 forte; Ethonium; etofyllinclofibrate; fenozan; glaucine; H290-51; histidyl-proline diketopiperazine; hydroquinone; hypotaurine; idebenone; indole-3-carbinol; isoascorbic acid; kojic acid, lacidipine, lodoxamide tromethamine; mexidol; morin; N,N'-diphenyl-4-phenylenediamine; N-isopropyl-N-phenyl-4-phenylenediamine; N-monoacetylcystine; nicaraven, nicotinoyl-GABA; nitecapone; nitroxyl; nobiletin; oxymethacil; p-tert-butyl catechol; phenidone; pramipexol; proanthocyanidin; procyanidin; prolinedithiocarbamate; Propyl Gallate; purpurogallin; pyrrolidine dithiocarbamic acid; rebamipide; retinol palmitate; salvin; Selenious Acid; sesamin; sesamol; sodium selenate; sodium thiosulfate; theaflavin; thiazolidine-4-carboxylic acid; tirilazad; tocopherylquinone; tocotrienol, alpha; a Tocotrienol; tricyclodecane-9-yl-xanthogenate; turmeric extract; U 74389F; U 74500A; U 78517F; ubiquinone 9; vanillin; vinpocetine; xylometazoline; zeta Carotene; zilascorb; zinc thionein; or zonisamide.

In additional embodiments, an agent in combination with a muscarinic agent, such as an inhibitor of AChE activity, may be a reported modulator of a norepinephrine receptor. Non-limiting examples include Atomoxetine (Strattera); a norepinephrine reuptake inhibitor, such as talsupram, tomoxetine, nortriptyline, nisoxetine, reboxetine (described, e.g., in U.S. Pat. No. 4,229,449), or tomoxetine (described, e.g., in U.S. Pat. No. 4,314,081); or a direct agonist, such as a beta adrenergic agonist.

Non-limiting examples of reported adrenergic agonists include albuterol, clonidine (CAS RN 4205-90-7), yohimbine (CAS RN 146-48-5), arbutamine; befunolol; BRL 26830A; BRL 35135; BRL 37344; bromoacetylalprenololmenthane; broxaterol; carvedilol; CGP 12177; cimaterol; cirazoline; CL 316243; Clenbuterol; denopamine; dexmedetomidine hydrochloride; Dobutamine, dopexamine, Ephedrine, Epinephrine, formoterol; formoterol fumarate; Hexoprenaline; higenamine; ICI D7114; Isoetharine; Isoproterenol; Isoxsuprine; levalbuterol tartrate hydrofluoroalkane; lidamidine; mabuterol; methoxyphenamine; modafinil; Nylidrin; Orciprenaline; Oxyfedrine; pirbuterol; Prenalterol; Procaterol; ractopamine; reproterol; Ritodrine; Ro 363; salmeterol; salmeterol xinafoate; SR 58611A; Terbutaline; tetramethylpyrazine; tizanidine hydrochloride; Tretoquinol; tulobuterol; Xamoterol; or zinterol.

In further embodiments, an agent in combination with a muscarinic agent, such as an inhibitor of AChE activity, may be a reported modulator of carbonic anhydrase. Non-limiting examples of such an agent include acetazolamide, benzenesulfonamide, Benzolamide, brinzolamide, Dichlorphenamide, dorzolamide, Ethoxzolamide, Flurbiprofen, Mafenide, Methazolamide, sezolamide, zonisamide, bendroflumethiazide, benzthiazide, chlorothiazide, cyclothiazide, dansylamide, diazoxide, ethinamate, furosemide, hydrochlorothiazide, hydroflumethiazide, mercuribenzoic acid, methyclothiazide, topiramate, or trichloromethazide.

In yet additional embodiments, an agent in combination with a muscarinic agent, such as an inhibitor of AChE activity, may be a reported modulator of COMT, such as floproprion, or a catechol-O-methyltransferase (COMT) inhibitor, such as tolcapone (CAS RN 134308-13-7), nitecapone (CAS RN 116313-94-1), or entacapone(CAS RN 116314-67-1 or 130929-57-6).

In yet further embodiments, an agent in combination with a muscarinic agent, such as an inhibitor of AChE activity, may be a reported modulator of hedgehog activity such as cyclopamine, jervine, lovastatin, ezetimibe, Regadenoson (CAS RN 313348-27-5, or CVT-3146), a compound described in U.S. Pat. No. 6,683,192 or identified as described in U.S. Pat. No. 7,060,450, or CUR-61414 or another compound described in U.S. Pat. No. 6,552,016.

In other embodiments, an agent in combination with a muscarinic agent, such as an inhibitor of AChE activity, may be a reported modulator of IMPDH, such as mycophenolic acid or mycophenolate mofetil (CAS RN 128794-94-5).

Other non-limiting examples of an agent in combination with a muscarinic agent, such as an inhibitor of AChE activity, include acamprosate (CAS RN 77337-76-9), a growth factor, octreotide (CAS RN 83150-76-9), modafinil, minocycline or metformin.

Of course a further combination therapy may also be that of a muscarinic agent, such as an inhibitor of AChE activity, with a non-chemical based therapy. limiting examples include the use of psychotherapy for the treatment of many conditions described herein, such as the psychiatric conditions, as well as behavior modification therapy such as that use in connection with a weight loss program.

Having now generally described the invention, the same will be more readily understood through reference to the following examples which are provided by way of illustration, and are not intended to be limiting of the present invention, unless specified.

EXAMPLES

The following examples are offered to illustrate, but not to limit the claimed invention.

Example 1

Effect on Neuronal Differentiation of Human Neural Stem Cells

Human neural stem cells (hNSCs) were isolated and grown in monolayer culture, plated, treated with varying concentrations of sabcomeline (test compound), and stained with TUJ-1 antibody, as described in U.S. Provisional Application No. 60/697,905 (incorporated by reference). Mitogen-free test media with 5 µM DHEA served as a positive control for neuronal differentiation, and basal media without growth factors served as a negative control. Results are shown in FIG. 1.

Example 2

Effect on Astrocyte Differentiation of hNSCs

Figure 2:
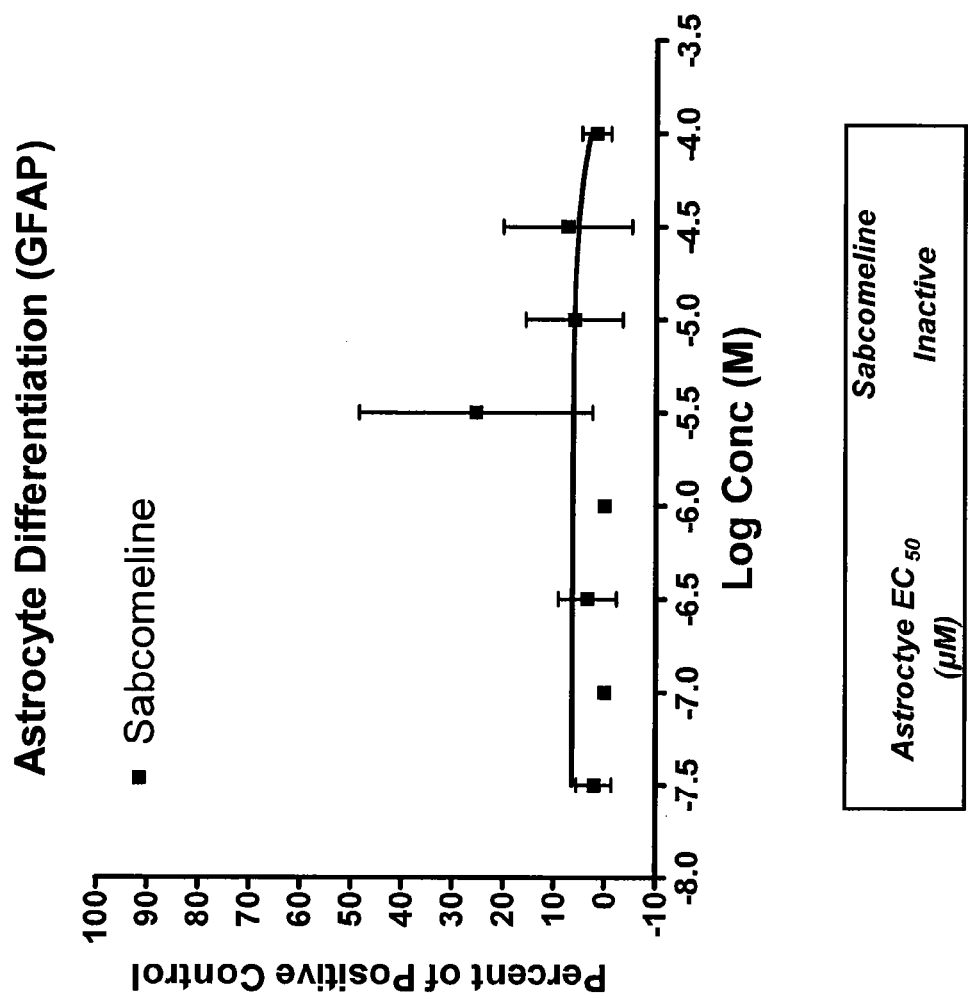
FIG. 2 is a dose-response curve showing effect of the muscarinic agent sabcomeline on astrocyte differentiation. Data is presented as the percentage of the astrocyte positive control, with basal media values subtracted. Sabcomeline was found to have no effect on astrocyte differentiation.

Experiments were carried out as described in Example 1, except the positive control for astrocyte differentiation contained mitogen-free test media with 50 ng/ml BMP-2, 50 ng/ml: LIF and 0.5% FBS, and cells were stained with GFAP antibody. Results are shown in FIG. 2.

Example 3

Toxic/trophic Effect on Human Neural Stem Cells

Figure 3:
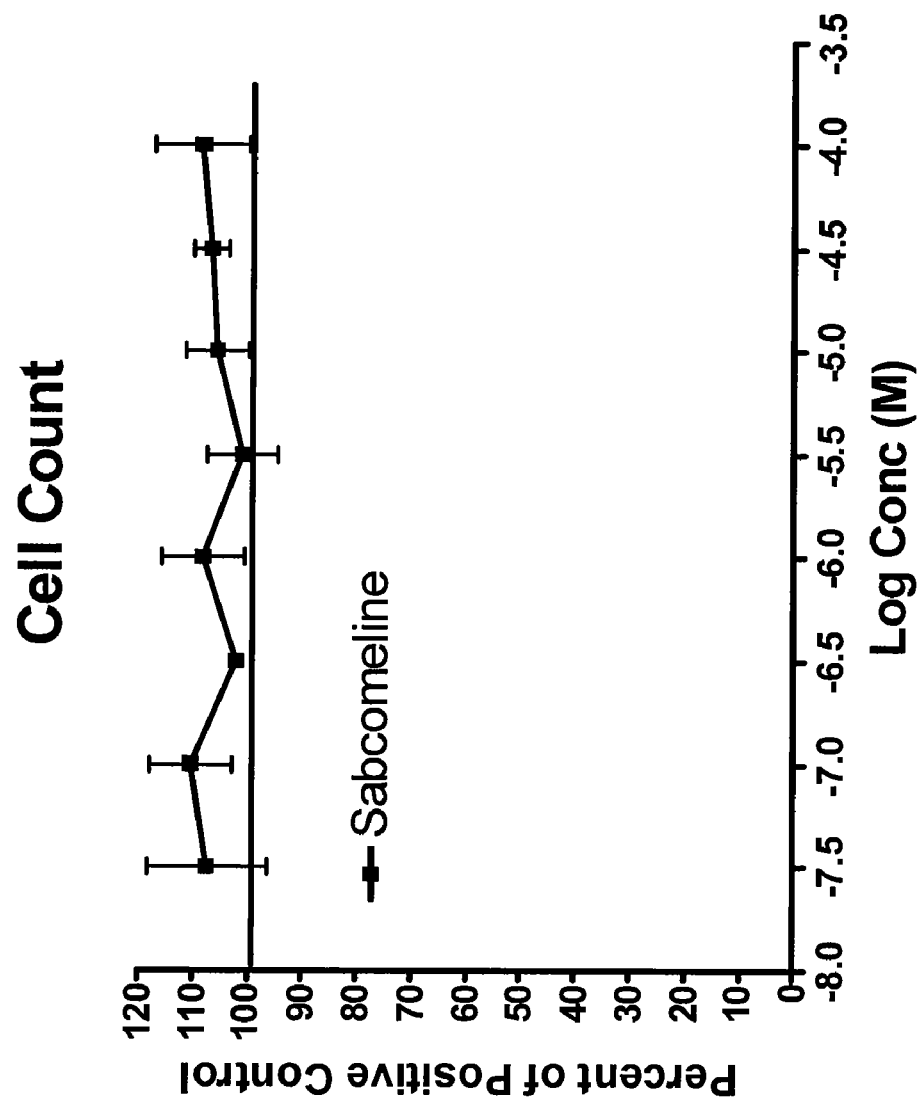
FIG. 3 is a dose-response curve measuring the toxicity/trophism effect of the muscarinic agent sabcomeline on a population of cultured neural stem cells. Data is presented as the percentage of the basal media cell count. Toxic doses produce viability values below 80% of the basal media control, while trophic compounds show a dose-dependent increase in cell count. Sabcomeline has no detectable toxicity, and shows a significant trophic effect.

Experiments were carried out as described in Example 1, except that the positive control contained basal media only, and cells were stained with nuclear dye (Hoechst 33342. Results are shown in FIG. 3.

Example 4

Proliferation of hNSCs in Neurosphere Culture

Figure 4:
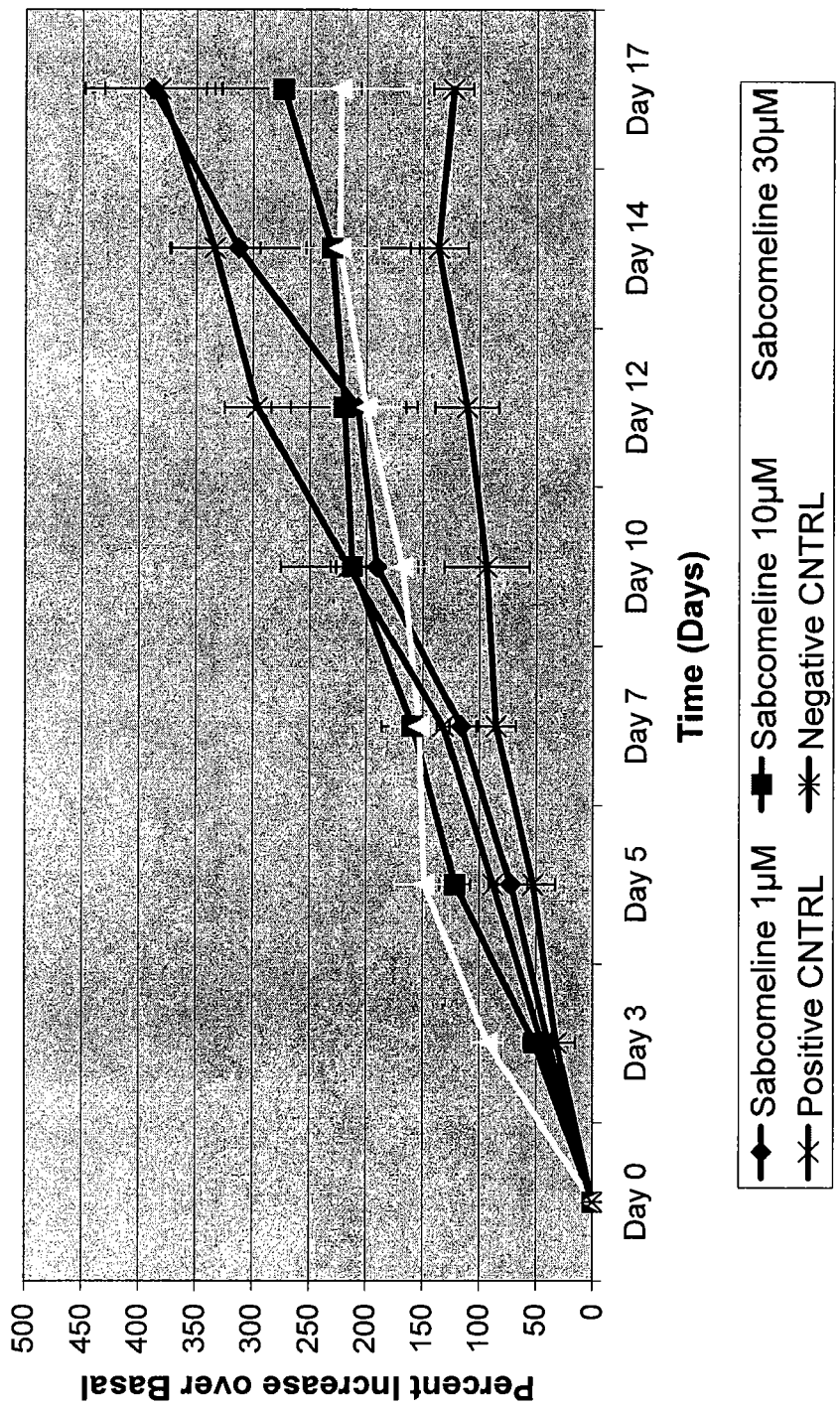
FIG. 4 shows the effect of various concentrations of the muscarinic agent sabcomeline on neurogenesis of human neural stem cells (hNSC) in neurosphere culture (diamonds: 1 µM sabcomeline; squares: 10 µM sabcomeline; triangles: 30 µM sabcomeline, X: positive control (basal media with known proliferative agent); asterisk: negative control (basal media). Neurogenesis is measured as the total area of a single neurosphere comprising human neural stem cells as a function of time. Results are presented as the percent increase in area over basal media. Sabcomeline enhanced proliferation and/or survival of hNSC compared to basal media at all time periods tested.
Figure 6:
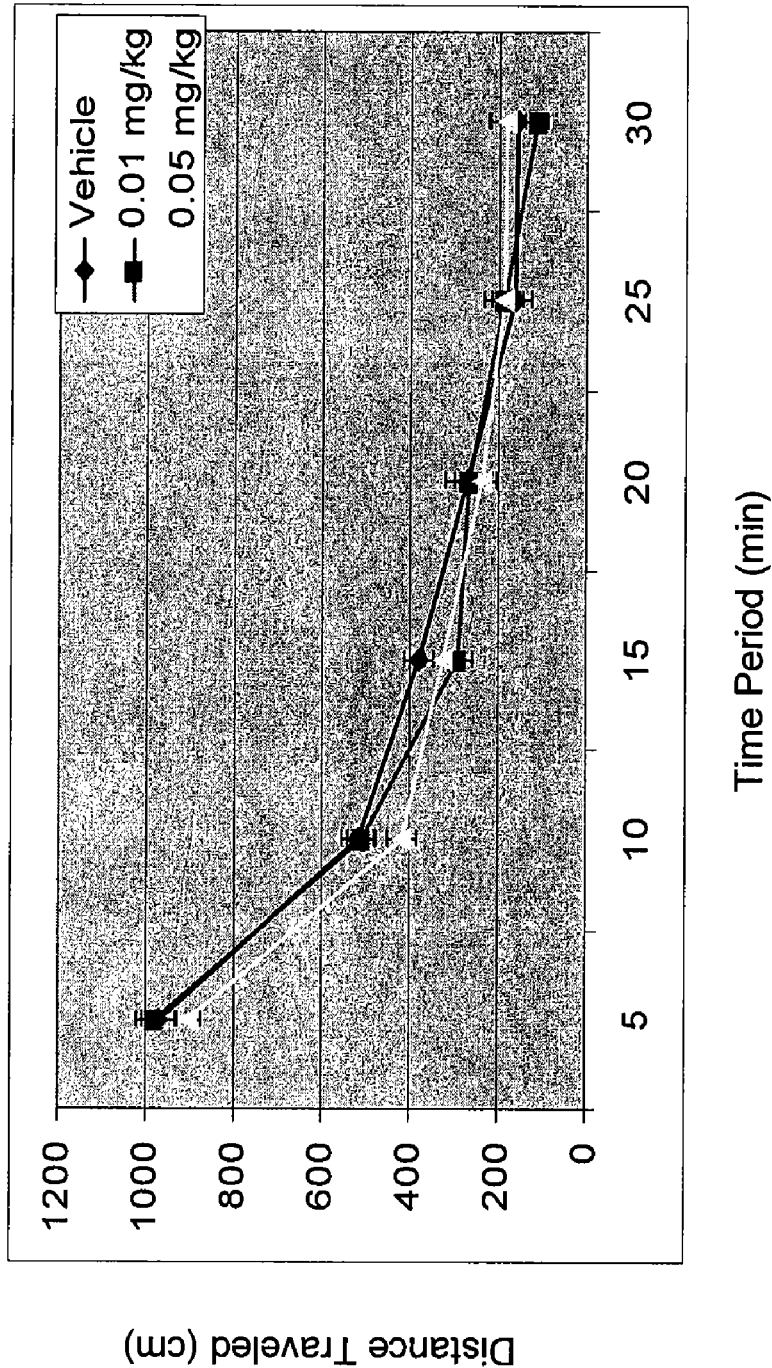
FIG. 6 shows the effect of chronic dosing with sabcomeline on the locomotor activity of rats (squares: 0.01 mg/kg; triangles: 0.05 mg/kg; diamonds: negative control (vehicle)). Sabcomeline had no significant effect on locomotor activity. "mpk" stands for mg/kg.
Figure 7:
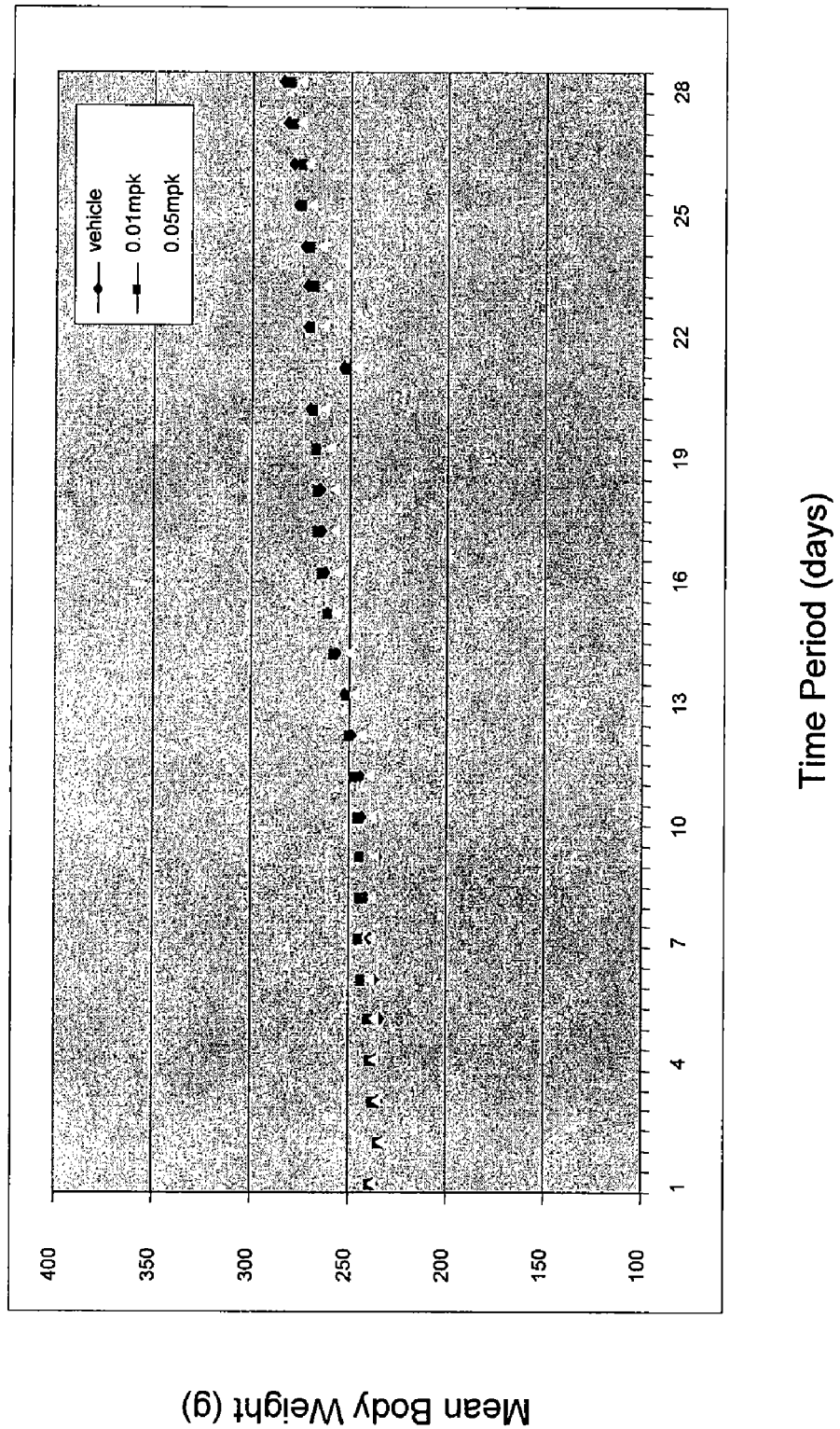
FIG. 7 shows the effect of chronic dosing with sabcomeline on the body weight of rats (squares: 0.01 mg/kg; triangles: 0.05 mg/kg; diamonds: negative control (vehicle)). Sabcomeline had no significant effect on body weight.
Figure 8:
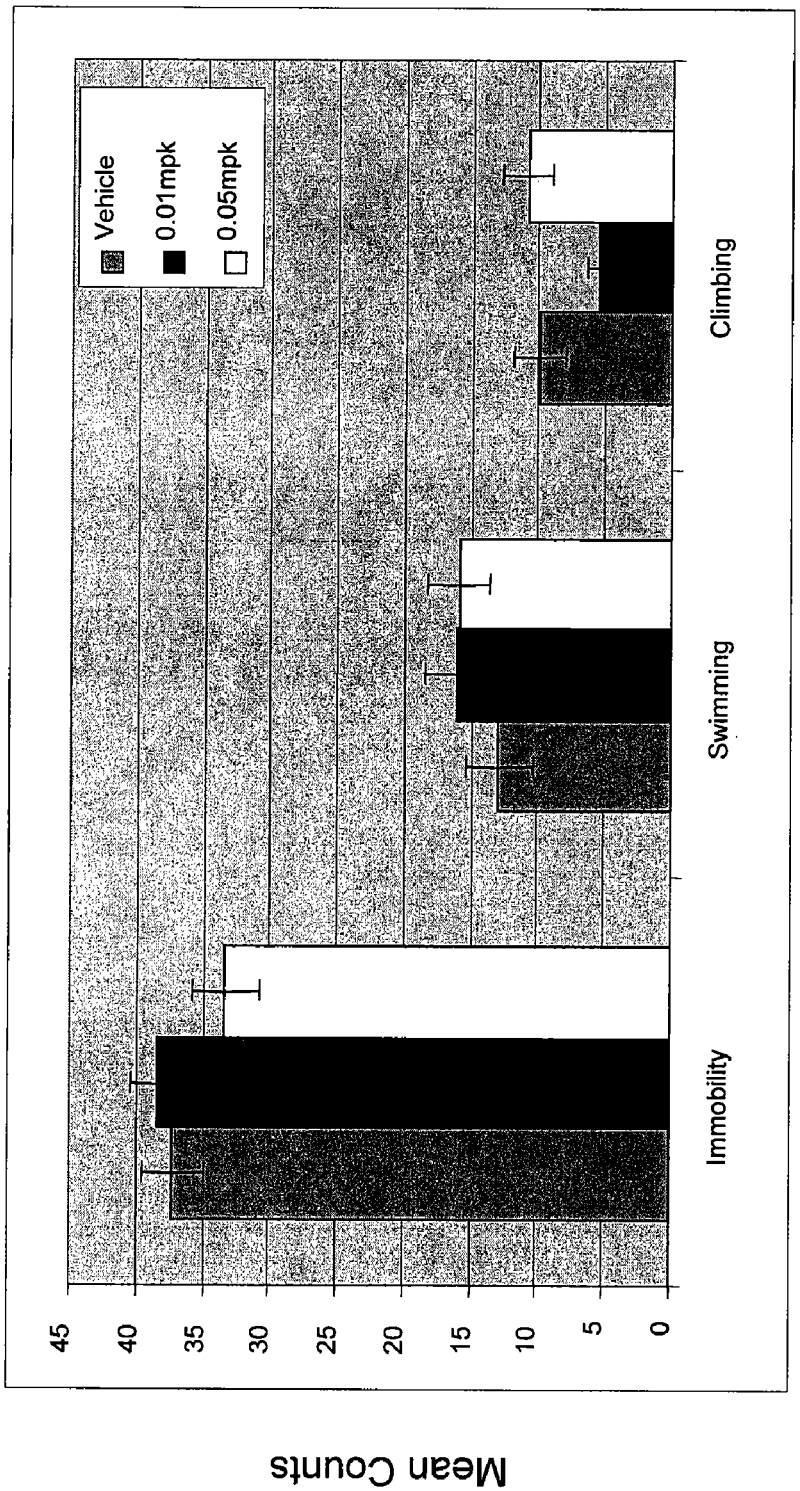
FIG. 8 shows the effect of acute dosing with sabcomeline on the performance of rats in the modified forced swim test (dark grey: 0.01 mg/kg; white: 0.05 mg/kg; light grey: negative control (vehicle). Sabcomeline had no significant effects on performance in the swim test.

The effect of sabcomeline on the growth rate of hNSCs in neurosphere culture was determined by measuring the area of individual neurospheres as a function of time, as described in U.S. Provisional Application No. 60/697,905 (incorporated by reference). Results are shown in FIG. 4.

Example 5

Immunohistochemistry with Neuronal and Astrocyte Markers

Immunohistochemistry was carried out as described in U.S. Provisional Application No. 60/697,905 (incorporated by reference).

Example 6

In Vivo Chronic Dosing Studies

Male Fischer F344 rats were treated with 0, 0.01 and 0.05 mg/kg sabcomeline for 28 days. FIG. 12 shows the effect of chronic dosing of rats with Sabcomeline on the differentiation of neural progenitor cells into mature neuron within the subgranular zone of the dentate gyrus. Various characteristics and behavioral responses in the treated rats were measured as described below.

Locomotor Activity

Open field activity during the light phase of the diurnal cycle is quantified via photoelectric cell monitoring in a Plexiglas cube open-field arena (45 cm×45 cm×50 cm high with infra-red (I/R) array, Hamilton-Kinder San Diego, Calif.). Measurements were collected for 30 mins (6 blocks of 5 min): ambulatory distance in center and periphery; ambulatory time in center and periphery; total time in center and periphery; rearing in center and periphery; the number of zone entries; and total distance. Testing began 30 minutes after Sabcomeline injection.

Body Weight

Rats were weighed daily.

Forced Swim Test

Active motor behavior is measured in a swim tank, this test being a modification of that described by Porsolt, R. D., Bertin, A., Jalfree, M. Arch. Int. Pharmacodyn Ther. 229 (1977) 327-336. The animal is placed into the swim tank (38 cm deep). The swim test consists of two phases; a 15 minute pretest and a 5 minute test 24-hours later. Activity is quantified by measuring three aspects of behavior: (1) immobility, defined as an absence of movement other than what is required to remain afloat, (2) swimming, defined as horizontal movement greater than what is required to remain afloat and (3) climbing, vertical movement greater than what is required to remain afloat. The predominant behavior is scored every 5 seconds by trained observers for a total of 5 minutes.

Novelty Suppressed Feeding Assay

Twenty-four hours prior to behavioral testing, all food is removed from the home cage. At the time of testing a single pellet is placed in the center of a novel arena. Animals are placed in the corner of the arena and latency to eat the pellet is recorded. Compounds are generally administered 30 minutes prior to testing. Animals receive compound daily for 21 days and testing is performed on day 21. A decreased latency to eat the food pellet is indicative of both neurogenesis and antidepressant activity.

Novel Object Recognition Assay

The apparatus consisted of an open field (45×45×50 cm high) made of polycarbonate. Triplicate copies were used of the objects to be discriminated. Care was taken to ensure that the pair of objects tested were made from the same material so that they could not be distinguished readily by olfactory cues although they had very different appearances. Each test session consisted of two phases. In the initial familiarization phase, two identical objects (A1 and A2) were placed in the far corners of the box arena. A rat was then placed in the middle of the arena and allowed 15 minutes to explore both objects. Exploration of an object was defined as directing the nose to the object at a distance of less than 2 cm and/or touching it with the nose. After a delay, the rat was re-introduced to the arena ("test phase"). The box now contained a third identical copy of the familiar object (A3) and a new object (B). These were placed in the same locations as the sample stimuli, whereby the position (left or right) of the novel object in the test phase was balanced between rats. For half the rats, object A was the sample and object B was the novel alternative. The test phase was 15 minutes in duration, with the first 30 seconds of object interaction used to determine preference scores. Any animal with less than 15 seconds of object exploration were excluded from analysis. FIG. 10 shows the effect of chronic dosing of rats with sabcomeline on cognitive performance in a novel object recognition assay.

Example 7

Effect of Acute Dosing on Proliferation of NSCs

Male Fischer F344 rats are injected with varying doses of test compound +vehicle or vehicle only (negative control) once daily for five days, followed by a single intraperitoneal injection with 100 mg/kg BrdU. Rats are then anesthetized and killed by transcardial perfusion of 4% paraformaldehyde at day 28. Brains were rapidly removed and stored in 4% paraformaldehyde for 24 hours and then equilibrated in phosphate buffered 30% sucrose. Free floating 40 micron sections were collected on a freezing microtome and stored in cryoprotectant. Antibodies against BrdU and cells types of interest (e.g., neurons, astrocytes, oligodendrocytes, endothelial cells) will also be used for detection of cell differentiation. In brief, tissues were washed (0.01 M PBS), endogenous per-oxidase blocked with 1% hydrogen peroxide, and incubated in PBS (0.01 M, pH 7.4, 10% normal goat serum, 0.5% Triton X-100) for 2 hours at room temperature. Tissues were then incubated with primary antibody at 4° C. overnight. The tissues were rinsed in PBS followed by incubation with biotinylated secondary antibody (1 hour at room temperature). Tissues were further washed with PBS and incubated in avidin-biotin complex kit solution at room temperature for 1 hour. Various fluorophores linked to streptavidin were used for visualization. Tissues were washed with PBS, briefly rinsed in dH$_2$O, serially dehydrated and coverslipped.

Cell counting and unbiased stereology was limited to the hippocampal granule cell layer proper and a 50 um border along the hilar margin that includes the neurogenic subgranular zone. The proportion of BrdU cells displaying a lineage-specific phenotype was determined by scoring the co-localization of cell phenotype markers with BrdU using confocal microscopy. Split panel and z-axis analysis were used for all counting. All counts were performed using multi-channel configuration with a 40× objective and electronic zoom of 2. When possible, 100 or more BrdU-positive cells were scored for each maker per animal. Each cell was manually examined in first full "z"-dimension and only those cells for which the nucleus is unambiguously associated with the lineage-specific marker were scored as positive. The total number of BrdU-labeled cells per hippocampal granule cell layer and subgranule zone were determined using diaminobenzadine stained tissues. Overestimation was corrected using the Abercrombie method for nuclei with empirically determined average diameter of 13 µm within a 40 µm section. The results, shown in FIG. 11, indicate that sabcomeline can produce neurogenic effects with a rapid onset of action.

Example 8

Effect of Combined Dosing of Sabcomeline and Fluoxetine on Antidepressant Activity Male Fischer F344 rats are chronically injected with test compound(s)+vehicle or vehicle only (negative control) once daily, and assayed in the novelty suppressed feeding assay as described above in example 6. The results, shown in FIG. 13A, indicate that the combination of sabcomeline and fluoxetine can produce antidepressant effects at extremely low doses that are significantly greater than either compound alone.

Example 9

Effect of Combined Dosing of Sabcomeline and Fluoxetine on Proliferation of NSCs Male Fischer F344 rats are injected with test compound(s)+vehicle or vehicle only (negative control) once daily for 28 days. Intraperitoneal injections with 100 mg/kg BrdU occur daily for 5 days after day 7. Rats are then anesthetized and killed by transcardial perfusion of 4% paraformaldehyde at day 28, and proliferating NCS's are measured as described above in Example 7. The results, shown in FIG. 13B, indicate that the combination of sabcomeline and fluoxetine results in significant neurogenic effects at very low doses of compound.

Example 10

Effect of Combining Donepezil and Captopril on Neuronal Differentiation of Human Neural Stem Cells Human neural stem cells (hNSCs) were isolated and grown in monolayer culture, plated, treated with varying concentrations of donepezil and/or captopril (test compounds), and stained with TUJ-1 antibody, as described in Example 1.

Figure 14:
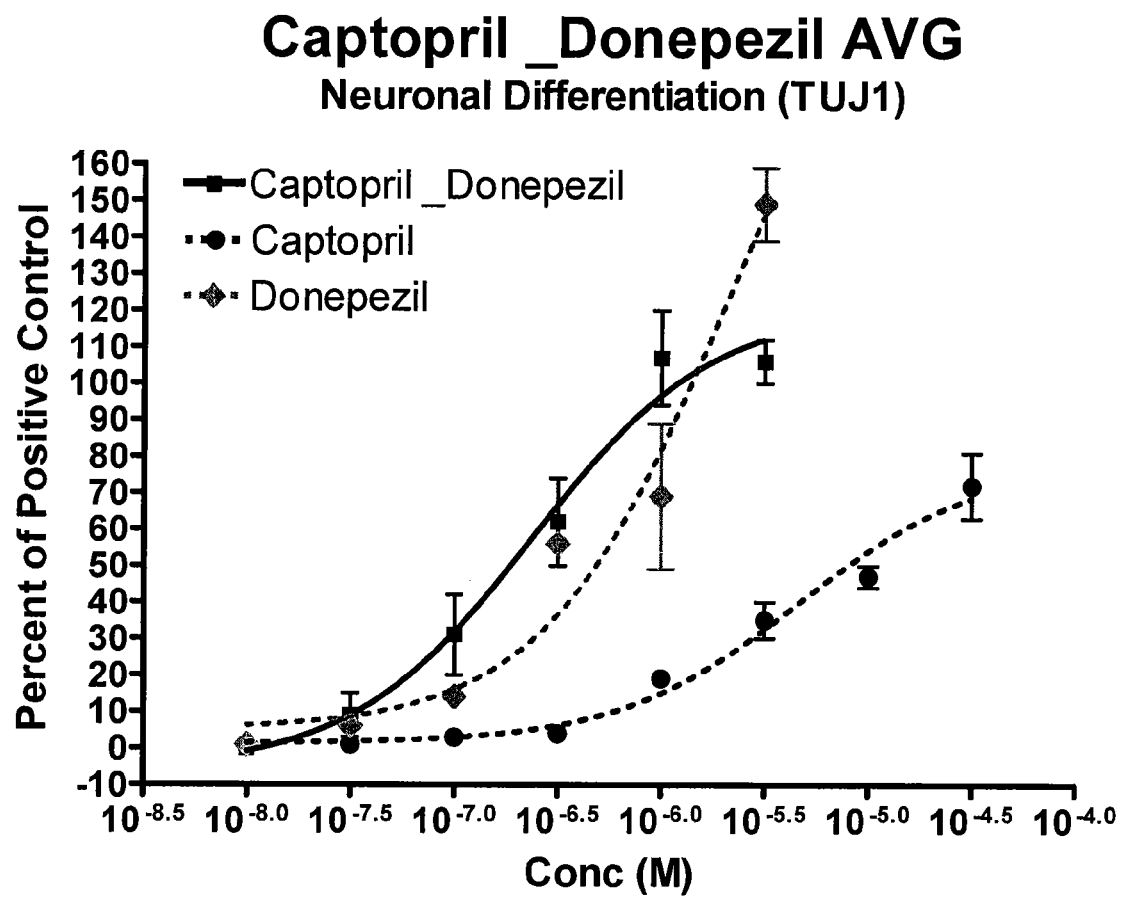
FIG. 14 is a dose-response curve showing effects of the neurogenic agents donepezil (acetylcholinesterase inhibitor) and captopril (angiotensin converting enzyme inhibitor) in combination on neuronal differentiation compared to the effect of either agent alone. When run independently, each compound was tested in a concentration response curve ranging from 0.01 µM to 31.6 µM. In combination, the compounds were combined at equal concentrations at each point (for example, the first point in the combined curve consisted of a test of 0.01 µM donepezil and 0.01 µM captopril). Data is presented as the percentage of the neuronal positive control, with basal media values subtracted. When used alone, $EC_{50}$ was observed at a donepezil concentration of 4.7 µM or a captopril concentration of 2.0 µM in test cells. When used in combination neurogenesis is greatly enhanced: $EC_{50}$ was observed at a combination of donepezil and captopril at concentrations of 0.24 µM each.

Results are shown in FIG. 14, which shows concentration dependent response curves of neuronal differentiation after subtraction of background media values. The concentration response curve of the combination of donepezil and captopril is shown with the concentration response curves of donepezil or captopril alone. The data is presented as a percent of neuronal positive control. The data indicate that the combination of donepezil and captopril resulted in superior promotion of neuronal differentiation than either agent alone.

Example 11

Reduction of Buspirone-induced Astrocyte Differentiation of Human Neural Stem Cells by Combination with Donepezil Human neural stem cells (hNSCs) were isolated and grown in monolayer culture, plated, treated with varying concentrations of donepezil and/or buspirone (test compounds), and stained with GFAP antibody, as described in U.S. Provisional Application No. 60/697,905 (incorporated by reference). Mitogen-free test media with a positive control for neuronal differentiation was used along with basal media without growth factors as a negative control.

Figure 15:
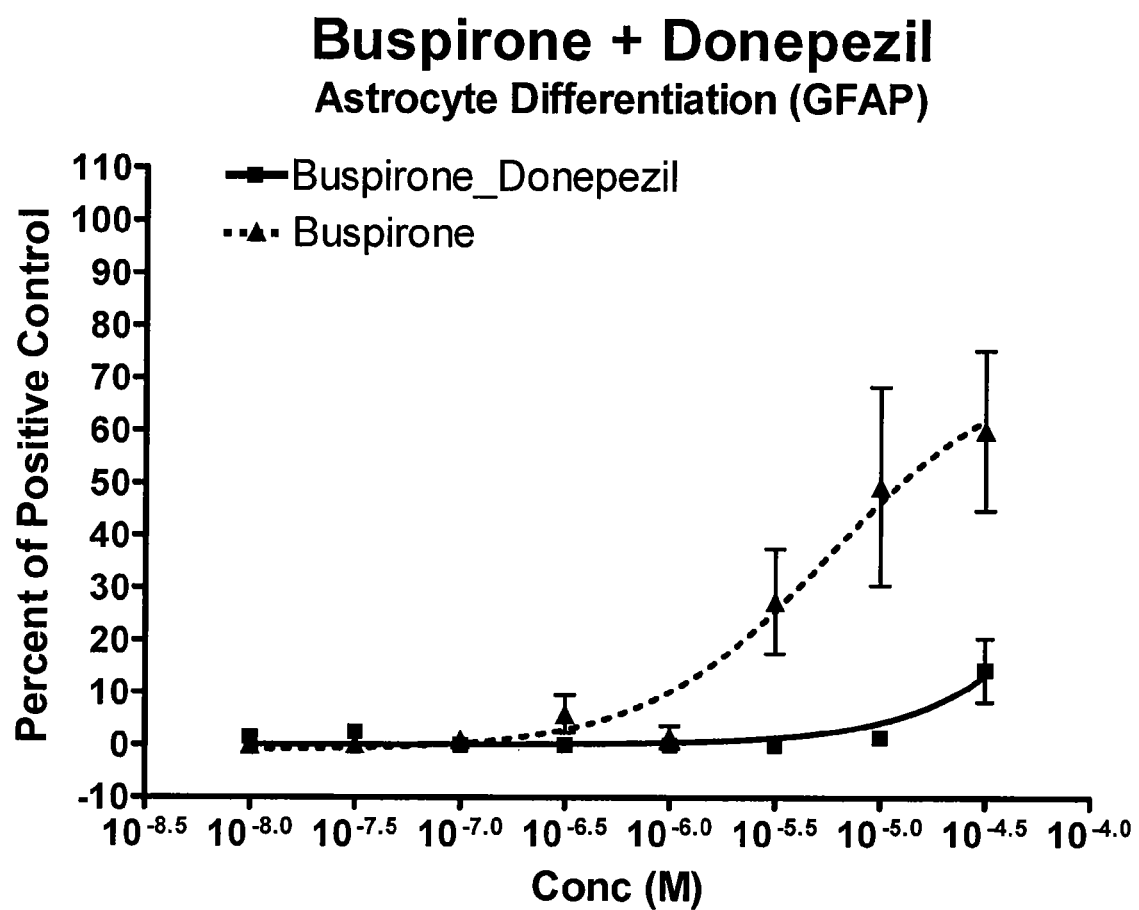
FIG. 15 is a dose-response curve showing the reduction of astrocyte differentiation by buspirone (a 5-HT1a agonist) in combination with donepezil (an acetylcholinesterase inhibitor). When run alone, buspirone potently induces astrocyte differentiation with an $EC_{50}$ of 5.7 µM at a maximum of 60% of the positive control. The addition of donepezil results in significant inhibition of astrocyte differentiation to a maximum of 14% positive control with an estimated $EC_{50}$ greater than 31.6 µM.

Results are shown in FIG. 15, which shows concentration dependent response curves of astrocyte differentiation after subtraction of background media values. The concentration response curve of the combination of donepezil and buspirone is shown with the concentration response curves of buspirone. The data are presented as a percent of neuronal positive control. The data indicate that the combination of donepezil with buspirone significantly reduced astrocyte differentiation.

Example 12

Determination of Synergy

The presence of synergy was determined by use of a combination index (CI). The CI based on the EC$_{50}$ as used to determine whether a pair of compound had an additive, synergistic (greater than additive), or antagonistic effect when run in combination. The CI is a quantitative measure of the nature of drug interactions, comparing the EC$_{50}$'s of two compounds, when each is assayed alone, to the EC$_{50}$ of each compound when assayed in combination. The combination index (CI) is equal to the following formula:

$$\frac{C1}{IC1} + \frac{C2}{IC2} + \frac{(C1 * C2)}{(IC1 * IC2)}$$

where C1 and C2 are the concentrations of a first and a second compound, respectively, resulting in 50% activity in neuronal differentiation when assayed in combination; and IC1 and IC2 are the concentrations of each compound resulting in 50% activity when assayed independently. A CI of less than 1 indicates the presence of synergy; a CI equal to 1 indicates an additive effect; and a CI greater than 1 indicates antagonism between the two compounds.

The combination of the muscarinic agent tacrine with the 5-HT1a receptor agonist buspirone resulted in synergistic activity. Tacrine alone has an $EC_{50}$ of 8.0 µM for neuronal differentiation. Buspirone alone has an $EC_{50}$ of 8.4 µM. The concentration of each agent in combination to reach 50% activity in neuronal differentiation is 0.122 µM, resulting in a CI of 0.03 by application of the above formula. As the CI is less than 1, the two compounds have a synergistic effect in neuronal differentiation.

The above is based on the selection of $EC_{50}$ as the point of comparison for the two compounds. The comparison is not limited by the point used, but rather the same comparison may be made at another point, such as $EC_{20}$, $EC_{30}$, $EC_{40}$, $EC_{60}$, $EC_{70}$, $EC_{80}$, or any other EC value above, below, or between any of those points.

All references cited herein, including patents, patent applications, and publications, are hereby incorporated by reference in their entireties, whether previously specifically incorporated or not.

Having now fully provided the instant disclosure, it will be appreciated by those skilled in the art that the same can be performed within a wide range of equivalent parameters, concentrations, and conditions without departing from the spirit and scope of the disclosure and without undue experimentation.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

What is claimed is:

1. A method of treating a nervous system disorder related to depression in a subject or patient in need thereof, comprising administering a composition consisting essentially of sabcomeline and an SSRI, wherein the composition is effective to treat the disorder.

2. The method of claim 1, wherein the SSRI is fluoxetine.

* * * * *